(12) United States Patent
Lee et al.

(10) Patent No.: US 7,550,574 B2
(45) Date of Patent: Jun. 23, 2009

(54) NUCLEIC ACIDS AND PROTEINS OF INSECT OR83B ODORANT RECEPTOR GENES AND USES THEREOF

(75) Inventors: Kevin J. Lee, New York, NY (US); Thuy-Ai T. Nguyen, Houston, TX (US); Brian Kloss, New York, NY (US)

(73) Assignee: SentiSearch, Inc., Santa Barbara, CA (US)

( * ) Notice: Subject to any disclaimer, the term of this patent is extended or adjusted under 35 U.S.C. 154(b) by 190 days.

(21) Appl. No.: 11/801,355

(22) Filed: May 9, 2007

(65) Prior Publication Data

US 2008/0176322 A1    Jul. 24, 2008

Related U.S. Application Data

(62) Division of application No. 10/486,781, filed on Aug. 6, 2004, now Pat. No. 7,238,798.

(51) Int. Cl.
*C12N 15/12* (2006.01)
*C07K 14/705* (2006.01)

(52) U.S. Cl. .................. 536/23.5; 435/69.1; 435/252.3; 435/320.1

(58) Field of Classification Search ........................ None
See application file for complete search history.

(56) References Cited

U.S. PATENT DOCUMENTS 6,703,491 B1 * 3/2004 Homburger et al. ........ 536/23.1

FOREIGN PATENT DOCUMENTS

WO    WO-00/50566    8/2000

OTHER PUBLICATIONS

Vosshall et al. A Spacial Map of Olfactory Receptor Expression in the *Drosophila* Antenna, Mar. 5, 1999, Cell 96:725-736.*
Jones et al. Functional Conservation of an Insect Odorant Receptor Gene Across 250 Million Years of Evolution. Feb. 22, 2005, Current Biology 15(4):R119-R121.*
Pitts et al. A Highly Conserved Candidate Chemoreceptor Expressed in Both Olfactory and Gustatory Tissues in the Malaria Vector Anopheles gambiae, Apr. 6, 2004, P.N.A.S. 101(14):5058-5063.*
L. B. Vosshall et al., "An olfactory sensory map in the fly brain," Cell, vol. 102, No. 2, 147-159 (Jul. 21, 2000).

* cited by examiner

*Primary Examiner*—John D Ulm
(74) *Attorney, Agent, or Firm*—Fulbright & Jaworski LLP

(57) ABSTRACT

The present invention relates to insect odorant receptor genes and methods for identifying odorant receptor genes. The invention provides nucleotide sequences of insect odorant receptor genes Or83b, amino acid sequences of their encoded proteins (including peptides or polypeptides), and related products and methods. The nucleic acids of the invention may be operatively linked to promoter sequences and transformed into host cells. Methods of production of an Or83b odorant receptor protein (e.g., by recombinant means), and derivatives and analogs thereof, are provided. Antibodies to an Or83b odorant receptor protein, and derivatives and analogs thereof, are provided. Methods for identifying molecules that bind or modulate the activity of these Or83b odorant receptor genes are provided. Molecules found to bind or modulate the activity of Or83b genes may be formulated into pest control agents by providing a carrier. In a preferred embodiment, molecules that bind or modulate the activity of an Or83b gene from one species but not others is desired. Methods to modify the insect behavior by modifying an insect Or83b odorant are also provided.

4 Claims, 20 Drawing Sheets

Figure 7A:
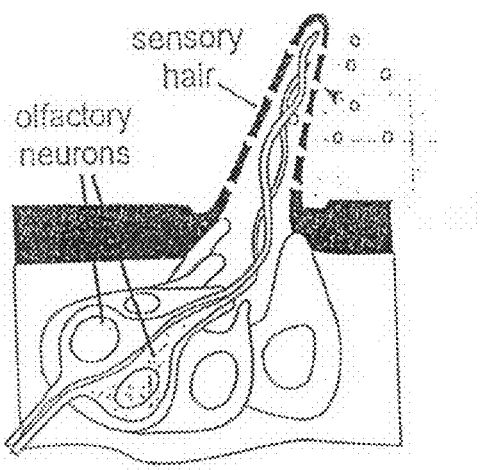

```
  1  GGCACGAGCT GGTTCCGGAA AGCCTCATAT CTCGTATCTT AAAGTATCCC
     CCGTGCTCGA CCAAGGCCTT TCGGAGTATA GAGCATAGAA TTTCATAGGG
 51  GGTTAAGCCT TAAAGAGTGA AATGATTGCC TAGACGATTG CTGCATTACT
     CCAATTCGGA ATTTCTCACT TTACTAACGG ATCTGCTAAC GACGTAATGA
101  GGCACTCAAT TAACCCAAGT GTACCAGACA ACAATTACAT TTGTATTTTT
     CCGTGAGTTA ATTGGGTTCA CATGGTCTGT TGTTAATGTA AACATAAAAA
 +3                       H  T  T  S  H  Q  P  S  K  Y  T
151  AAAGTTCAAT AGCAAGGATG ACAACCTCGA TGCAGCCGAG CAAGTACACG
     TTTCAAGTTA TCGTTCCTAC TGTTGGAGCT ACGTCGGCTC GTTCATGTGC
 +3     G  L  V  A  D  L  H  P  K  I  R  A  H  K  Y  S  G
201  GGCCTGGTCG CGGACCTGAT GCCCAACATC CGGGCGATGA AGTACTCCGG
     CCGGACCAGC GCCTGGACTA CGGGTTGTAG GCCCGCTACT TCATGAGGCC
 +3     G  L  F  H  N  F  T  G  G  S  A  F  H  K  K  V  Y
251  CCTGTTCATG CACAACTTCA CGGGCGGCAG TGCCTTCATG AAGAAGGTGT
     GGACAAGTAC GTGTTGAAGT GCCCGCCGTC ACGGAAGTAC TTCTTCCACA
 +3    ·Y  S  S  V  H  L  V  F  L  L  H  Q  F  T  F  I  L
301  ACTCCTCCGT GCACCTGGTG TTCCTCCTCA TGCAGTTCAC CTTCATCCTG
     TGAGGAGGCA CGTGGACCAC AAGGAGGAGT ACGTCAAGTG GAAGTAGGAC
 +3     V  N  H  A  L  N  A  E  E  V  N  E  L  S  G  H  T
351  GTCAACATGG CCCTGAACGC CGAGGAGGTC AACGAGCTGT CGGGCAACAC
     CAGTTGTACC GGGACTTGCG GCTCCTCCAG TTGCTCGACA GCCCGTTGTG
 +3     T  I  T  T  L  F  F  T  H  C  I  T  K  F  I  Y  L  A
401  GATCACGACC CTCTTCTTCA CCCACTGCAT CACGAAGTTT ATCTACCTGG
     CTAGTGCTGG GAGAAGAAGT GGGTGACGTA GTGCTTCAAA TAGATGGACC
 +3     A  V  N  Q  K  N  F  Y  R  T  L  N  I  W  H  Q  V
451  CTGTTAACCA GAAGAATTTC TACAGAACAT TGAATATATG GAACCAGGTG
     GACAATTGGT CTTCTTAAAG ATGTCTTGTA ACTTATATAC CTTGGTCCAC
 +3    ·N  T  H  P  L  F  A  E  S  D  A  R  Y  H  S  I  A
501  AACACGCATC CCTTGTTCGC CGAGTCGGAT GCTCGTTACC ATTCGATCGC
     TTGTGCGTAG GGAACAAGCG GCTCAGCCTA CGAGCAATGG TAAGCTAGCG
 -3    ·A  L  A  K  H  R  K  L  F  F  L  V  H  L  T  T  V  A
551  ACTGGCGAAG ATGAGGAAGC TGTTCTTTCT GGTGATGCTG ACCACAGTCG
     TGACCGCTTC TACTCCTTCG ACAAGAAAGA CCACTACGAC TGGTGTCAGC
 +3    ·A  S  A  T  A  W  T  T  I  T  F  F  G  D  S  V  K
601  CCTCGGCCAC CGCCTGGACC ACGATCACCT TCTTTGGCGA CAGCGTAAAA
     GGAGCCGGTG GCGGACCTGG TGCTAGTGGA AGAAACCGCT GTCGCATTTT
 +3     H  V  V  D  H  E  T  N  S  I  P  V  E  I  P  R
651  ATGGTGGTGG ACCATGAGAC GAACTCCAGC ATCCCGGTGG AGATACCCCG
     TACCACCACC TGGTACTCTG CTTGAGGTCG TAGGGCCACC TCTATGGGGC
 +3    ·R  L  P  I  K  S  F  Y  P  W  N  A  S  H  G  H  F  Y
701  GCTGCCGATT AAGTCCTTCT ACCCGTGGAA CGCCAGCCAC GGCATGTTCT
     CGACGGCTAA TTCAGGAAGA TGGGCACCTT GCGGTCGGTG CCGTACAAGA
 +3    ·Y  H  I  S  F  A  F  Q  I  Y  Y  V  L  F  S  M  I
751  ACATGATCAG CTTTGCCTTT CAGATCTACT ACGTGCTCTT CTCGATGATC
     TGTACTAGTC GAAACGGAAA GTCTAGATGA TGCACGAGAA GAGCTACTAG
 +3     H  S  N  L  C  D  V  M  F  C  S  W  L  I  F  A  C
801  CACTCCAATC TATGCGACGT GATGTTCTGC TCTTGGCTGA TATTCGCCTG
     GTGAGGTTAG ATACGCTGCA CTACAAGACG AGAACCGACT ATAAGCGGAC
```

FIG. 1A

SEQ ID NOs 9 + 10

```
     +3  ·C  E   Q   L   Q   H   L   K   G   I   H   K   P   L   H   E   L   S·
 851    CGAGCAGCTG CAGCACTTGA AGGGCATCAT GAAGCCGCTG ATGGAGCTGT
        GCTCGTCGAC GTCGTGAACT TCCCGTAGTA CTTCGGCGAC TACCTCGACA
     -1  ·S  A   S   L   D   T   Y   R   P   N   S   A   A   L   F   R   S
 901    CCGCCTCGCT GGACACCTAC AGGCCCAACT CGGCGGCCCT CTTCAGGTCC
        GGCGGAGCGA CCTGTGGATG TCCGGGTTGA GCCGCCGGGA GAAGTCCAGG
     +1   L   S   A   N   S   K   S   E   L   I   H   N   E   E   K   D   P·
 951    CTGTCGGCCA ACTCCAAGTC GGAGCTAATT CATAATGAAG AAAAGGATCC
        GACAGCCGGT TGAGGTTCAG CCTCGATTAA GTATTACTTC TTTTCCTAGG
     +3  ·P  G   T   D   M   D   H   S   G   I   Y   S   S   K   A   D   W   G·
1001    CGGCACCGAC ATGGACATGT CGGGCATCTA CAGCTCGAAA GCGGATTGGG
        GCCGTGGCTG TACCTGTACA GCCCGTAGAT GTCGAGCTTT CGCCTAACCC
     -1  ·G  A   Q   F   R   K   P   S   T   L   Q   S   F   G   G   N   G
1051    GCGCTCAGTT TCGAGCACCC TCGACACTGC AGTCCTTTGG CGGGAACGGG
        CGCGAGTCAA AGCTCGTGGG AGCTGTGACG TCAGGAAACC GCCCTTGCCC
     +3   G   G   N   G   L   V   N   G   A   N   P   N   G   L   T   K·
1101    GGCGGAGGCA ACGGGTTGGT GAACGGCGCT AATCCCAACG GGCTGACCAA
        CCGCCTCCGT TGCCCAACCA CTTGCCGCGA TTAGGGTTGC CCGACTGGTT
     +3  ·K  K   Q   E   M   M   V   R   S   A   I   K   Y   W   V   E   R   H·
1151    AAAGCAGGAG ATGATGGTGC GCAGTGCCAT CAAGTACTGG GTCGAGCGGC
        TTTCGTCCTC TACTACCACG CGTCACGGTA GTTCATGACC CAGCTCGCCG
     +3  ·H  K   H   V   V   R   L   V   A   A   I   G   D   T   Y   G   A
1201    ACAAGCACGT GGTGCGACTG GTGGCTGCCA TCGGCGATAC TTACGGAGCC
        TGTTCGTGCA CCACGCTGAC CACCGACGGT AGCCGCTATG AATGCCTCGG
     +3   A   L   L   L   H   H   L   T   S   T   I   K   L   T   L   L   A·
1251    GCCCTCCTCC TCCACATGCT GACCTCGACC ATCAAGCTGA CCCTGCTGGC
        CGGGAGGAGG AGGTGTACGA CTGGAGCTGG TAGTTCGACT GGGACGACCG
     -1  ·A  T   Q   A   T   K   I   N   G   V   N   V   Y   A   F   T   V   V·
1301    ATACCAGGCC ACCAAAAATCA ACGGAGTGAA TGTCTACGCC TTCACAGTCG
        TATGGTCCGG TGGTTTTAGT TGCCTCACTT ACAGATGCGG AAGTGTCAGC
     -3  ·V  G   Y   L   G   Y   A   L   A   Q   V   F   H   F   C   I   F
1351    TCGGATACCT AGGATACGCG CTGGCCCAGG TGTTCCACTT TTGCATCTTT
        AGCCTATGGA TCCTATGCGC GACCGGGTCC ACAAGGTGAA AACGTAGAAA
     -3    G   N   R   L   I   E   E   S   S   S   V   H   E   A   A   Y   S·
1401    GGCAATCGTC TGATTGAAGA GAGTTCATCC GTCATGGAGG CCGCCTACTC
        CCGTTAGCAG ACTAACTTCT CTCAAGTAGG CAGTACCTCC GGCGGATGAG
     +3  ·S  C   H   W   Y   D   G   S   E   E   A   K   T   F   V   Q   I   V
1451    GTGCCACTGG TACGATGGCT CCGAGGAGGC CAAGACCTTC GTCCAGATCG
        CACGGTGACC ATGCTACCGA GGCTCCTCCG GTTCTGGAAG CAGGTCTAGC
     +3  ·V  C   Q   Q   C   Q   K   A   M   S   I   G   A   K   F   F
1501    TGTGCCAGCA GTGCCAGAAG GCGATGAGCA TATCGGGAGC GAAATTCTTC
        ACACGGTCGT CACGGTCTTC CGCTACTCGT ATAGCCCTCG CTTTAAGAAG
     +3   T   V   S   L   D   L   F   A   S   V   L   G   A   V   V   T   Y·
1551    ACCGTCTCCC TGGATTTGTT TGCTTCGGTT CTGGGTGCCG TCGTCACCTA
        TGGCAGAGGG ACCTAAACAA ACGAAGCCAA GACCCACGGC AGCAGTGGAT
     +3  ·Y  F   H   V   L   V   Q   L   K
1601    CTTTATGGTG CTGGTGCAGC TCAAGTAAGT TGCTGCGAAG CTGATGGATT
        GAAATACCAC GACCACGTCG AGTTCATTCA ACGACGCTTC GACTACCTAA
```

FIG. 1B
SEQ ID NOS: 9 + 10

```
1651  TTTGTACCAG AAAAGCGAAT GCCAAGAAGC CACCTACCGC CCCTTGCCCC
      AAACATGGTC TTTTCGCTTA CGGTTCTTCG GTGGATGGCG GGGAACGGGG
1701  CTCCGCACTG TGCAACCAGC AATATCACAG AGCAATTATA ACGCAAATTA
      GAGGCGTGAC ACGTTGGTCG TTATAGTGTC TCGTTAATAT TGCGTTTAAT
1751  TATATTTTAT ACCTGCGACG AGCGAGCCTC GTGGGGCATA ATGGAGACAT
      ATATAAAATA TGGACGCTGC TCGCTCGGAG CACCCCGTAT TACCTCTGTA
1801  TCTGGGGCAC ATAGAAGCCT GCAAATACTT ATCGATTTTG TACACGCGTA
      AGACCCCGTG TATCTTCGGA CGTTTATGAA TAGCTAAAAC ATGTGCGCAT
1851  GAGCTTTTAA TGTAAACTCA AGATGCAAAC TAAATAAATG TGTAGTGAAA
      CTCGAAAATT ACATTTGAGT TCTACGTTTG ATTTATTTAC ACATCACTTT
1901  AAAAAAAAAA AAAAAAA
      TTTTTTTTTT TTTTTTT
```

FIG. 1C

SEQ ID NOS: 9 + 10

```
+1     M   Q   P   S   K   Y   V   G   L   V   A   D   L   M   P   N   I·
  1    ATGCAGCCGA GTAAATATGT TGGCCTCGTG GCCGATTTGA TGCCGAACAT
       TACGTCGGCT CATTTATACA ACCGGAGCAC CGGCTAAACT ACGGCTTGTA
+1    ·I   R   L   K   Y   S   G   L   F   M   H   N   F   T   G   G   S·
 51    ACGTCTGATG AAGTACTCGG GCTTGTTCAT GCACAACTTC ACTGGCGGTT
       TGCAGACTAC TTCATGAGCC CGAACAAGTA CGTGTTGAAG TGACCGCCAA
+1    ·S   G   L   F   K   K   I   Y   S   S   M   H   L   V   L   V   L
101    CCGGACTCTT TAAGAAAATT TACTCATCCA TGCATTTGGT TTTGGTTTTG
       GGCCTGAGAA ATTCTTTTAA ATGAGTAGGT ACGTAAACCA AAACCAAAAC
+1     V   Q   F   L   L   I   L   V   N   L   A   L   N   A   E   E   V·
151    GTGCAATTTC TATTGATACT GGTGAATTTG GCATTAAATG CGGAGGAGGT
       CACGTTAAAG ATAACTATGA CCACTTAAAC CGTAATTTAC GCCTCCTCCA
+1    ·V   N   E   L   S   G   N   T   I   T   V   L   F   F   T   H   C  I·
201    GAATGAGTTG TCCGGCAATA CAATAACCGT GCTCTTCTTT ACTCATTGCA
       CTTACTCAAC AGGCCGTTAT GTTATTGGCA CGAGAAGAAA TGAGTAACGT
+1    ·I   T   K   F   I   Y   L   A   V   T   Q   K   Q   F   Y   R   T
251    TAACGAAATT CATCTATTTG GCCGTTACAC AGAAGCAGTT CTACAGAACG
       ATTGCTTTAA GTAGATAAAC CGGCAATGTG TCTTCGTCAA GATGTCTTGC
+1     L   N   I   W   N   Q   V   N   S   H   P   L   F   A   E   S   D·
301    TTGAATATAT GGAATCAAGT GAATTCGCAT CCATTGTTCG CCGAGTCGGA
       AACTTATATA CCTTAGTTCA CTTAAGCGTA GGTAACAAGC GGCTCAGCCT
+1    ·D   A   R   Y   H   S   I   A   L   A   K   M   R   K   L   F   T  L·
351    TGCGCGCTAC CACTCGATTG CGCTCGCCAA AATGCGAAAG CTCTTCACAC
       ACGCGCGATG GTGAGCTAAC GCGAGCGGTT TTACGCTTTC GAGAAGTGTG
+1     L   V   H   L   T   T   V   V   S   A   V   A   W   T   T   I   T
401    TGGTTATGCT CACCACCGTC GTTTCAGCTG TGGCTTGGAC TACTATTACA
       ACCAATACGA GTGGTGGCAG CAAAGTCGAC ACCGAACCTG ATGATAATGT
+1     F   F   G   E   S   V   K   F   A   F   D   K   D   T   N   S   S·
451    TTCTTCGGTG AGAGCGTTAA ATTTGCCTTC GACAAGGATA CCAACTCTTC
       AAGAAGCCAC TCTCGCAATT TAAACGGAAG CTGTTCCTAT GGTTGAGAAG
+1    ·S   I   T   V   E   I   P   R   L   P   I   K   S   F   Y   P   W  N·
501    AATAACCGTT GAAATTCCAC GCTTGCCCAT TAAATCCTTT TACCCGTGGA
       TTATTGGCAA CTTTAAGGTG CGAACGGGTA ATTTAGGAAA ATGGGCACCT
+1    ·N   A   G   S   G   H   F   Y   I   I   S   F   A   F   Q   C   Y
551    ATGCCGGCTC GGGCATGTTT TACATAATCA GTTTCGCTTT TCAATGCTAC
       TACGGCCGAG CCCGTACAAA ATGTATTAGT CAAAGCGAAA AGTTACGATG
+1     Y   L   L   F   S   M   V   H   S   N   L   C   D   V   L   F   C·
601    TATCTGCTCT TCTCTATGGT TCACTCTAAT TTATGTGATG TGCTCTTCTG
       ATAGACGAGA AGAGATACCA AGTGAGATTA AATACACTAC ACGAGAAGAC
+1    ·C   S   W   L   I   F   A   C   E   Q   L   Q   H   L   K   G   I  H·
651    TTCGTGGTTG ATTTTCGCCT GCGAGCAGTT ACAACACCTG AAAGGTATCA
       AAGCACCAAC TAAAAGCGGA CGCTCGTCAA TGTTGTGGAC TTTCCATAGT
+1    ·M   K   P   L   H   E   L   S   A   S   L   D   T   Y   R   P   N
701    TGAAACCGTT GATGGAGCTG TCAGCCTCAT TGGACACCTA TCGGCCAAAT
       ACTTTGGCAA CTACCTCGAC AGTCGGAGTA ACCTGTGGAT AGCCGGTTTA
+1     S   A   L   F   R   S   L   S   A   N   S   K   S   E   L   I·
751    TCGGCTGCAC TATTTCGTTC GCTATCGGCC AATTCTAAAT CGGAATTGAT
       AGCCGACGTG ATAAAGCAAG CGATAGCCGG TTAAGATTTA GCCTTAACTA
```

FIG. 2A
(SEQ ID NOS: 1 + 2)

```
     +1  ·I  H   N   E   E   K   E   P   T   D   L   D   V   S   G   I   Y   S·
    801  AAATAATGAG GAGAAGGAAC CCACTGATCT GGACGTTAGT GGCATTTACA
         TTTATTACTC CTCTTCCTTG GGTGACTAGA CCTGCAATCA CCGTAAATGT
     +1  ·S   S   K   A   D   W   G   A   Q   F   R   A   P   S   T   L   Q
    851  GCTCCAAAGC AGATTGGGGC GCACAGTTTC GTGCACCATC AACGTTACAA
         CGAGGTTTCG TCTAACCCCG CGTGTCAAAG CACGTGGTAG TTGCAATGTT
     +1   T   F   N   G   M   N   G   T   N   P   N   G   L   T   R   K   Q·
    901  ACCTTCAATG GCATGAATGG TACCAATCCG AATGGTTTGA CCAGAAAGCA
         TGGAAGTTAC CGTACTTACC ATGGTTAGGC TTACCAAACT GGTCTTTCGT
     +1  ·Q   E   M   M   V   R   S   A   I   K   Y   W   V   E   R   H   K   H·
    951  GGAGATGATG GTGCGCAGTG CCATTAAATA TTGGGTTGAA CGACACAAGC
         CCTCTACTAC CACGCGTCAC GGTAATTTAT AACCCAACTT GCTGTGTTCG
     +1  ·H   V   V   R   L   V   A   A   I   G   D   T   Y   G   G   A   L
   1001  ACGTTGTAAG ATTAGTTGCA GCTATCGGCG ATACATATGG CGGCGCTTTG
         TGCAACATTC TAATCAACGT CGATAGCCGC TATGTATACC GCCGCGAAAC
     +1   L   L   M   L   T   S   T   I   M   L   T   L   L   A   Y   Q·
   1051  TTGTTGCACA TGTTGACATC CACCATTATG CTAACGTTGT TGGCTTATCA
         AACAACGTGT ACAACTGTAG GTGGTAATAC GATTGCAACA ACCGAATAGT
     +1  ·Q   A   T   K   I   T   G   V   N   V   Y   A   F   T   T   V   G   Y·
   1101  GGCCACGAAG ATCACCGGCG TCAATGTTTA CGCCTTCACC ACGGTCGGTT
         CCGGTGCTTC TAGTGGCCGC AGTTACAAAT GCGGAAGTGG TGCCAGCCAA
     +1  ·Y   L   C   Y   A   L   A   Q   V   F   H   F   C   I   F   G   M
   1151  ATTTGTGCTA TGCTTTGGCG CAGGTATTTC ATTTTTGCAT ATTTGGCAAT
         TAAACACGAT ACGAAACCGC GTCCATAAAG TAAAAACGTA TAAACCGTTA
     +1   R   L   I   E   E   S   S   S   V   M   E   A   A   Y   S   C   H·
   1201  CGGCTGATTG AGGAGAGCTC ATCCGTTATG GAGGCAGCCT ACTCCTGCCA
         GCCGACTAAC TCCTCTCGAG TAGGCAATAC CTCCGTCGGA TGAGGACGGT
     +1  ·H   W   Y   D   G   S   E   E   A   K   T   F   V   Q   I   V   C   Q·
   1251  TTGGTATGAT GGCTCCGAGG AGGCCAAGAC TTTTGTCCAG ATCGTTTGCC
         AACCATACTA CCGAGGCTCC TCCGGTTCTG AAAACAGGTC TAGCAAACGG
     +1  ·Q   Q   C   Q   K   A   M   S   I   S   G   A   K   F   F   T   V
   1301  AGCAGTGCCA AAAGGCGATG TCCATATCAG GAGCGAAGTT TTTCACCGTC
         TCGTCACGGT TTTCCGCTAC AGGTATAGTC CTCGCTTCAA AAAGTGGCAG
     -1   S   L   D   L   F   A   S   V   L   G   A   V   V   T   Y   F   M·
   1351  TCATTGGATT TGTTTGCATC GGTTCTTGGC GCTGTGGTCA CCTATTTCAT
         AGTAACCTAA ACAAACGTAG CCAAGAACCG CGACACCAGT GGATAAAGTA
     +1  ·H   V   L   V   Q   L   K
   1401  GGTGTTGGTA CAATTGAAGT GA
         CCACAACCAT GTTAACTTCA CT
```

FIG. 2B (SEQ ID NOS: 1+2)

```
  1  GGCACGAGGG CACGCGTCTG TCATACATTT TTGGAAAATG ATAACAAAAT
     CCGTGCTCCC GTGCGCAGAC AGTATGTAAA AACCTTTTAC TATTGTTTTA
 51  ATTGGCCATC TTAGTTGGAT GACTCTCTTT TGTTTCTGAA AAGGATTATT
     TAACCGGTAG AATCAACCTA CTGAGAGAAA ACAAAGACTT TCCTAATAA
+1                         M  M  T  K  V  K  A  Q  G  L  V
101  TTCGGAAAAC ATTCAAGATG ATGACCAAGG TGAAGGCCCA GGGCCTCGTG
     AAGCCTTTTG TAAGTTCTAC TACTGGTTCC ACTTCCGGGT CCCGGAGCAC
+1     S  D  L  M  P  N  I  K  L  M  Q  M  A  G  H  F  L
151  TCAGACTTGA TGCCCAACAT CAAGCTGATG CAGATGGCCG GGCATTTCCT
     AGTCTGAACT ACGGGTTGTA GTTCGACTAC GTCTACCGGC CCGTAAAGGA
+1    L  F  N  Y  H  S  E  N  A  G  M  S  H  L  L  R  K  I
201  CTTCAATTAC CATTCAGAAA ATGCTGGCAT GTCAAACCTT CTCCGTAAGA
     GAAGTTAATG GTAAGTCTTT TACGACCGTA CAGTTTGGAA GAGGCATTCT
+1    I  Y  A  S  T  H  A  I  L  I  F  I  H  Y  A  C  M
251  TCTACGCGAG TACTCATGCC ATCTTGATCT TTATCCACTA TGCTTGTATG
     AGATGCGCTC ATGAGTACGG TAGAACTAGA AATAGGTGAT ACGAACATAC
+1     G  I  N  M  A  K  Y  S  D  E  V  N  E  L  T  A  K
301  GGCATCAACA TGGCGAAATA CTCCGATGAA GTCAACGAGC TGACGGCGAA
     CCGTAGTTGT ACCGCTTTAT GAGGCTACTT CAGTTGCTCG ACTGCCGCTT
+1    N  T  I  T  V  L  F  F  A  H  T  I  I  K  L  A  F  F
351  TACCATCACT GTTCTATTCT TCGCTCATAC TATCATCAAG CTTGCTTTCT
     ATGGTAGTGA CAAGATAAGA AGCGAGTATG ATAGTAGTTC GAACGAAAGA
+1    F  A  L  N  K  S  F  Y  R  T  L  A  V  W  N  Q
401  TCGCCTTAAA TTCTAAGAGC TTCTATAGGA CCCTGGCAGT ATGGAACCAG
     AGCGGAATTT AAGATTCTCG AAGATATCCT GGGACCGTCA TACCTTGGTC
+1     S  N  S  H  P  L  F  T  E  S  D  A  R  Y  H  Q  I
451  TCGAACAGTC ACCCGCTGTT CACGGAGTCA GATGCCCGCT ACCACCAGAT
     AGCTTGTCAG TGGGCGACAA GTGCCTCAGT CTACGGGCGA TGGTGGTCTA
+1    I  A  L  T  K  M  R  R  L  L  Y  F  I  C  G  M  T  V
501  CGCGCTCACC AAGATGAGGA GGCTGCTGTA CTTCATCTGC GGGATGACTG
     GCGCGAGTGG TTCTACTCCT CCGACGACAT GAAGTAGACG CCCTACTGAC
+1    V  L  S  V  I  S  W  V  T  L  T  F  F  G  E  S  V
551  TCCTCTCTGT TATCAGCTGG GTAACCCTCA CATTCTTCGG CGAGTCAGTG
     AGGAGAGACA ATAGTCGACC CATTGGGAGT GTAAGAAGCC GCTCAGTCAC
+1     R  M  V  T  N  K  E  T  H  E  T  L  T  E  V  V  P
601  CGCATGGTGA CGAACAAGGA AACCCACGAG ACCCTGACGG AGGTGGTGCC
     GCGTACCACT GCTTGTTCCT TTGGGTGCTC TGGGACTGCC TCCACCACGG
+1    P  R  L  P  L  K  A  W  Y  P  F  N  A  M  S  G  T  M
651  CCGGCTACCT CTGAAGGCCT GGTACCCCTT CAATGCTATG AGCGGGACTA
     GGCCGATGGA GACTTCCGGA CCATGGGGAA GTTACGATAC TCGCCCTGAT
+1    M  Y  I  V  A  F  A  F  Q  V  Y  W  L  L  F  S  M
701  TGTATATTGT GGCGTTCGCT TTTCAGGTAT ACTGGCTCCT ATTCTCAATG
     ACATATAACA CCGCAAGCGA AAAGTCCATA TGACCGAGGA TAAGAGTTAC
+1     A  I  A  H  L  M  D  V  M  F  C  S  W  L  I  F  A
751  GCCATAGCGA ACCTCATGGA TGTCATGTTC TGTTCCTGGC TGATCTTCGC
     CGGTATCGCT TGGAGTACCT ACAGTACAAG ACAAGGACCG ACTAGAAGCG
+1    A  C  E  Q  L  Q  H  L  K  A  I  M  K  P  L  M  E  L
801  GTGTGAACAG CTGCAGCATC TGAAGGCTAT CATGAAACCT CTCATGGAGT
     CACACTTGTC GACGTCGTAG ACTTCCGATA GTACTTTGGA GAGTACCTCA
```

FIG. 3A
(SEQ ID NOS: 3 + 4)

```
      +1   L  S  A  S  L  D  T  Y  R  P  N  T  A  E  L  F  R
     851   TGAGCGCCTC CTTGGACACT TACCGGCCTA ATACTGCTGA GCTGTTCCGA
           ACTCGCGGAG GAACCTGTGA ATGGCCGGAT TATGACGACT CGACAAGGCT
      +1   A  S  S  I  E  K  S  E  K  I  P  D  T  V  D  M  D
     901   GCTTCTTCTA CTGAGAAATC CGAAAAGATC CCCGACACGG TAGACATGGA
           CGAAGAAGAT GACTCTTTAG GCTTTTCTAG GGGCTGTGCC ATCTGTACCT
      +1   D  I  R  G  I  Y  S  T  Q  Q  D  E  G  M  T  L  R  G
     951   CATCCGCGGC ATCTACTCCA CGCAGCAAGA CTTCGGCATG ACACTGCGAG
           GTAGGCGCCG TAGATGAGGT GCGTCGTTCT GAAGCCGTAC TGTGACGCTC
      +1   G  A  G  G  R  L  Q  N  F  G  Q  Q  N  P  N  P  N
    1001   GTGCTGGTGG AAGACTCCAG AACTTCGGCC AGCAGAACCC CAACCCTAAC
           CACGACCACC TTCTGAGGTC TTGAAGCCGG TCGTCTTGGG GTTGGGATTG
      +1   G  L  T  P  K  Q  E  H  L  A  R  S  A  I  K  Y  W
    1051   GGCTTGACCC CCAAGCAGGA GATGCTGGCC AGGTCTGCTA TCAAGTACTG
           CCGAACTGGG GGTTCGTCCT CTACGACCGG TCCAGACGAT AGTTCATGAC
      +1   W  V  E  R  H  K  H  V  V  R  L  V  A  S  I  G  D  T
    1101   GGTGGAGAGG CATAAGCATG TCGTCAGACT AGTGGCATCA ATTGGAGACA
           CCACCTCTCC GTATTCGTAC AGCAGTCTGA TCACCGTAGT TAACCTCTGT
      +1   T  Y  G  T  A  L  L  F  H  M  L  V  S  T  I  T  L
    1151   CGTATGGTAC CGCCCTGCTG TTCCACATGT TGGTGTCTAC CATCACGCTC
           GCATACCATG GCGGGACGAC AAGGTGTACA ACCACAGATG GTAGTGCGAG
      +1   T  L  L  A  Y  Q  A  T  K  I  N  G  I  N  V  Y  A
    1201   ACCCTGCTGG CCTACCAAGC TACTAAGATC AACGGAATCA ACGTGTATGC
           TGGGACGACC GGATGGTTCG ATGATTCTAG TTGCCTTAGT TGCACATACG
      +1   K  F  S  T  I  G  Y  L  S  Y  T  L  G  Q  V  F  H
    1251   TTTCAGTACA ATTGGATACT TGAGTTACAC TCTCGGTCAA GTGTTCCACT
           AAAGTCATGT TAACCTATGA ACTCAATGTG AGAGCCAGTT CACAAGGTGA
      +1   F  C  I  F  G  N  R  L  I  E  E  S  S  S  V  M  E
    1301   TCTGCATTTT CGGAAATAGG CTCATTGAAG AGAGCTCATC AGTAATGGAG
           AGACGTAAAA GCCTTTATCC GAGTAACTTC TCTCGAGTAG TCATTACCTC
      +1   A  A  Y  S  C  Q  W  I  G  S  E  E  A  K  T  F
    1351   GCAGCTTACT CCTGCCAGTG GTATGACGGC TCCGAGGAAG CGAAGACATT
           CGTCGAATGA GGACGGTCAC CATACTGCCG AGGCTCCTTC GCTTCTGTAA
      +1   F  V  Q  I  V  C  Q  Q  C  Q  K  A  H  S  I  S  G  A
    1401   CGTGCAGATC GTCTGCCAAC AGTGCCAGAA AGCTATGAGC ATCTCCGGAG
           GCACGTCTAG CAGACGGTTG TCACGGTCTT TCGATACTCG TAGAGGCCTC
      +1   A  K  F  F  T  V  S  L  D  L  F  A  S  V  L  G  A
    1451   CCAAGTTCTT CACGGTGTCC CTTGATTGT  TCGCTTCGGT TCTTGGAGCC
           GGTTCAAGAA GTGCCACAGG GAACTAAACA AGCGAAGCCA AGAACCTCGG
      +1   V  V  T  Y  F  H  V  L  V  Q  L  K
    1501   GTGGTTACCT ACTTCATGGT GTTGGTACAA CTCAAGTAAA CTGGACAAAC
           CACCAATGGA TGAAGTACCA CAACCATGTT GAGTTCATTT GACCTGTTTG
    1551   TACAAAATTG CTACTCTATT ACAAACTCTT ATTTTAATAA TTTGGTCTAT
           ATGTTTTAAC GATGAGATAA TGTTTGAGAA TAAAATTATT AAACCAGATA
    1601   CGTAAATACA TATGTATTTA AATCAACTTT TTTTCGCGAA CAATTTAATT
           GCATTTATGT ATACATAAAT TTAGTTGAAA AAAAGCGCTT GTTAAATTAA
    1651   TTAATCTCGT CATATGAGTT AATGGATACA GTTTAGTGGT TGAACAATAA
           AATTAGAGCA GTATACTCAA TTACCTATGT CAAATCACCA ACTTGTTATT
```

FIG. 3B
(SEQ ID NOS: 3 & 4)

```
1701  AGCTTATGCT CACCACTACA AATTATGCTG CGGTATATTG TAGCATCTGT
      TCGAATACGA GTGGTGATGT TTAATACGAC GCCATATAAC ATCGTAGACA
1751  TTACTAAAGT ACTTTACTGG AGTCTGTCGA GCTTAATTTA CATGACGCAT
      AATGATTTCA TGAAATGACC TCAGACAGCT CGAATTAAAT GTACTGCGTA
1801  TATGAAAAAT GAGCGCAGTT TTCAACCGAG CATGCATTTG ACGTCACATT
      ATACTTTTTA CTCGCGTCAA AAGTTGGCTC GTACGTAAAC TGCAGTGTAA
1851  TTGATGGAAA AAAACAGCGG TAGGAAATTA TATAGGTACT TATGTTGTAA
      AACTACCTTT TTTTGTCGCC ATCCTTTAAT ATATCCATGA ATACAACATT
1901  GTAGGAAAAA AAAAAAAAAA AAAA
      CATCCTTTTT TTTTTTTTTT TTTT
```

FIG. 3C (SEQ ID NOS: 3 + 4)

FIG. 4A
(SEQ ID NOS: 5+6)

```
      +1   ·E  L  I   I   N  E  E   K  D  P  D   V  K  D   F  D  L  S·
     801   GCTGATCATC AACGAAGAAA AGGATCCGGA CGTTAAGGAC TTTGATCTGA
           CGACTAGTAG TTGCTTCTTT TCCTAGGCCT GCAATTCCTG AAACTAGACT
      +1   ·S  G  I   Y  S  S   K  A  D  W   G  A  Q   F  R  A  P
     851   GCGGCATCTA CAGCTCGAAG GCGGACTGGG GCGCCCAGTT CCGTGCGCCG
           CGCCGTAGAT GTCGAGCTTC CGCCTGACCC CGCGGGTCAA GGCACGCGGC
      +1   ·S  T  L   Q  T  F   D  E  N   G  R  H  G   N  P  H  G·
     901   TCGACGCTGC AAACGTTCGA CGAGAATGGC AGGAACGGAA ATCCAACGG
           AGCTGCGACG TTTGCAAGCT GCTCTTACCG TCCTTGCCTT TAGGCTTGCC
      +1   ·G  L  T   R  K  Q   E  N  H  V   R  S  A  I   K  Y  W  V·
     951   GCTTACCCGG AAGCAGGAAA TGATGGTGCG CAGCGCCATC AAGTACTGGG
           CGAATGGGCC TTCGTCCTTT ACTACCACGC GTCGCGGTAG TTCATGACCC
      +1   ·V  E  R   H  K  H   V  V  R   L  V  S  A   I  G  D  T
    1001   TCGAGCGGCA CAAGCACGTT GTACGTCTCG TTTCAGCAAT CGGAGATACG
           AGCTCGCCGT GTTCGTGCAA CATGCAGAGC AAAGTCGTTA GCCTCTATGC
      +1     Y  G  P   A  L  L   L  H  H   L  T  S  T   I  K  L  T·
    1051   TACGGTCCTG CCCTGCTGCT GCACATGCTG ACTTCCACCA TCAAGCTGAC
           ATGCCAGGAC GGGACGACGA CGTGTACGAC TGAAGGTGGT AGTTCGACTG
      +1   ·T  L  L   A  Y  Q   K  T  K  I   D  G  V  N   V  Y  G  L·
    1101   GCTGCTCGCC TACCAGGCAA CGAAAATCGA CGGTGTCAAC GTGTACGGAT
           CGACGAGCGG ATGGTCCGTT GCTTTTAGCT GCCACAGTTG CACATGCCTA
      +1   ·L  T  V   I  G  Y   L  C  Y  A   L  A  Q   V  F  L  F
    1151   TGACCGTAAT CGGATATTTG TGCTACGCGT TGGCTCAGGT TTTCCTGTTT
           ACTGGCATTA GCCTATAAAC ACGATGCGCA ACCGAGTCCA AAAGGACAAA
      +1     C  I  F   G  N  R   L  I  E  E   S  S  S   V  M  E  A·
    1201   TGCATCTTTG GCAATCGGCT CATCGAGGAG AGCTCATCCG TGATGGAGGC
           ACGTAGAAAC CGTTAGCCGA GTAGCTCCTC TCGAGTAGGC ACTACCTCCG
      +1   ·A  A  Y   S  C  H  W   Y  D  G   S  E  E   A  K  T  F  V·
    1251   GGCCTATTCC TGCCACTGGT ACGACGGGTC CGAGGAGGCA AAAACCTTCG
           CCGGATAAGG ACGGTGACCA TGCTGCCCAG GCTCCTCCGT TTTTGGAAGC
      +1   ·V  Q  I   V  C  Q  Q   C  Q  K   A  M  T  I   S  G  A
    1301   TCCAGATCGT TTGTCAGCAG TGCCAGAAGG CGATGACTAT TTCCGGAGCC
           AGGTCTAGCA AACAGTCGTC ACGGTCTTCC GCTACTGATA AAGGCCTCGG
      +1     K  F  F   T  V  S   L  D  L  F   A  S  V   L  G  A  V·
    1351   AAGTTTTTCA CCGTTTCGCT CGATCTGTTT GCTTCGGTTC TTGGAGCCGT
           TTCAAAAAGT GGCAAAGCGA GCTAGACAAA CGAAGCCAAG AACCTCGGCA
      +1   ·V  V  T   Y  F  N  V   L  V  Q   L  K
    1401   TGTCACCTAC TTCATGGTGC TGGTACAGCT GAAGTAA
           ACAGTGGATG AAGTACCACG ACCATGTCGA CTTCATT
```

FIG. 4B (SEQ ID NOS: 5+6)

```
 +1    M   Q   K   P   H   G   L   V   A   D   L   W   P   L   I   R   M
   1  ATGCAGAAGC CGCATGGGCT GGTGGCGGAC CTGTGGCCGC TGATCCGCAT
      TACGTCTTCG GCGTACCCGA CCACCGCCTG GACACCGGCG ACTAGGCGTA
 +1    M   V   Q   Y   S   G   H   W   H   L   E   Y   S   G   G   L   T   A
  51  GGTGCAGTAC TCGGGCCACT GGATGCTCGA GTACAGCGGC GGCCTCACGG
      CCACGTCATG AGCCCGGTGA CCTACGAGCT CATGTCGCCG CCGGAGTGCC
 +1    A   L   R   A   I   Y   S   S   V   V   S   V   L   V   V   T   Q
 101  CCCTGCGCGC CATCTACAGC TCGGTCGTGT CCGTCCTGGT CGTGACGCAG
      GGGACGCGCG GTAGATGTCG AGCCAGCACA GGCAGGACCA GCACTGCGTC
 +1    F   A   L   H   A   V   H   L   I   Q   R   S   G   D   V   N   E
 151  TTCGCGCTCA TGGCCGTCAA CCTCATCCAG CGGTCCGGCG ACGTCAACGA
      AAGCGCGAGT ACCGGCAGTT GGAGTAGGTC GCCAGGCCGC TGCAGTTGCT
 +1    E   L   A   A   N   T   I   T   V   L   F   F   L   H   P   I   T   K
 201  GCTGGCGGCC AACACCATCA CGGTGCTCTT CTTCCTGCAC CCCATCACCA
      CGACCGCCGG TTGTGGTAGT GCCACGAGAA GAAGGACGTG GGGTAGTGGT
 +1    K   F   A   Y   F   A   V   R   S   K   A   F   Y   R   T   L   A
 251  AGTTCGCCTA CTTCGCGGTG CGCTCCAAGG CCTTCTACCG CACGCTCGCC
      TCAAGCGGAT GAAGCGCCAC GCGAGGTTCC GGAAGATGGC GTGCGAGCGG
 +1    T   W   N   Q   S   N   N   H   P   L   F   A   E   S   Q   A   R
 301  ACATGGAACC AGTCCAACAA CCACCCGCTG TTTGCAGAGT CACAGGCGCG
      TGTACCTTGG TCAGGTTGTT GGTGGGCGAC AAACGTCTCA GTGTCCGCGC
 +1    R   F   H   Q   L   S   V   V   R   H   R   R   L   V   H   Y   V   V
 351  CTTCCACCAG CTGTCCGTGG TGCGCATGCG CCGGCTCGTG ATGTACGTGG
      GAAGGTGGTC GACAGGCACC ACGCGTACGC GGCCGAGCAC TACATGCACC
 +1    V   S   V   T   A   L   S   V   V   S   W   T   S   I   T   F   M
 401  TGTCCGTGAC GGCGCTCAGC GTCGTGTCCT GGACCTCCAT CACCTTCATG
      ACAGGCACTG CCGCGAGTCG CAGCACAGGA CCTGGAGGTA GTGGAAGTAC
 +1    G   D   S   R   E   V   P   D   P   D   N   A   N   E   T   I
 451  GGCGACTCGA CGCGGGAGGT GCCCGACCCC GACAACGCCA ACGAGACCAT
      CCGCTGAGCT GCGCCCTCCA CGGGCTGGGG CTGTTGCGGT TGCTCTGGTA
 +1    I   T   E   E   V   P   R   L   M   I   S   T   W   Y   P   F   D   A
 501  CACCGAGGAG GTCCCCAGGC TCATGATCAG CACCTGGTAC CCGTTCGACG
      GTGGCTCCTC CAGGGGTCCG AGTACTAGTC GTGGACCATG GGCAAGCTGC
 +1    A   S   S   G   H   G   Y   M   L   A   F   I   Y   Q   L   Y   W
 551  CCTCTTCTGG TATGGGATAC ATGCTCGCCT TCATATACCA GCTGTACTGG
      GGAGAAGACC ATACCCTATG TACGAGCGGA AGTATATGGT CGACATGACC
 +1    L   T   A   T   L   M   H   S   N   L   H   D   V   M   F   C   C
 601  CTGACGGCGA CGCTGATGCA CTCCAACCTG ATGGACGTGA TGTTCTGCTG
      GACTGCCGCT GCGACTACGT GAGGTTGGAC TACCTGCACT ACAAGACGAC
 +1    C   W   L   I   T   A   C   E   Q   L   V   H   L   K   E   I   M   K
 651  CTGGCTCATC TACGCGTGTG AGCAGCTGGT GCACCTCAAG GAGATCATGA
      GACCGAGTAG ATGCGCACAC TCGTCGACCA CGTGGAGTTC CTCTAGTACT
 +1    K   P   L   H   E   L   S   A   T   L   D   T   V   V   P   H   T
 701  AGCCGCTCAT GGAGCTCAGC GCCACGCTGG ACACCGTGGT GCCGCACACC
      TCGGCGAGTA CCTCGAGTCG CGGTGCGACC TGTGGCACCA CGGCGTGTGG
 +1    S   E   L   F   R   A   A   S   T   L   P   T   N   E   P   L   Y
 751  AGCGAGCTCT TCCGAGCCGC CTCCACACTG CCCACCAACG AGCCACTCTA
      TCGCTCGAGA AGGCTCGGCG GAGGTGTGAC GGGTGGTTGC TCGGTGAGAT
```

FIG. 5A
(SEQ ID NOS. 7 + 8)

```
     +1   · Y  G  M  G  P  D  M  S  N  G  V  I  D  G  M  I  I  R·
     801  CGGGATGGGG CCAGACATGA GCAACGGCGT GACGGACGGC ATGACGATCC
          GCCCTACCCC GGTCTGTACT CGTTGCCGCA CTGCCTGCCG TACTGCTAGG
     +1   · R  G  I  Y  S  S  Q  R  D  F  S  G  F  N  R  R  S
     851  GCGGCATCTA CAGCAGCCAG CGCGACTTCT CGGGCTTCAA CCGGCGCTCG
          CGCCGTAGAT GTCGTCGGTC GCGCTGAAGA GCCCGAAGTT GGCCGCGAGC
     +1   · A  A  L  S  T  V  R  E  A  D  S  G  G  A  V  T  S·
     901  GCGGCGCTGT CGACGGTGCG CGAGGCCGAT TCGGGCGGCG CCGTCACCTC
          CGCCGCGACA GCTGCCACGC GCTCCGGCTA AGCCCGCCGC GGCAGTGGAG
     +1   · S  A  G  G  I  G  P  H  G  L  S  K  R  Q  E  M  L  V·
     951  CGCCGGCGGC ATCGGGCCCA ACGGGCTCAG CAAGCGCCAG GAGATGCTGG
          GCGGCCGCCG TAGCCCGGGT TGCCCGAGTC GTTCGCGGTC CTCTACGACC
     +1   · V  R  S  A  I  K  Y  W  V  E  R  H  K  H  V  V  R
    1001  TGCGCTCCGC CATCAAGTAC TGGGTCGAGC GACACAAGCA CGTGGTCAGG
          ACGCGAGGCG GTAGTTCATG ACCCAGCTCG CTGTGTTCGT GCACCAGTCC
     +1     F  V  G  N  I  G  D  A  Y  G  A  A  L  L  H  M·
    1051  TTCGTGGGCA ACATCGGGGA CGCATACGGC GCGGCGCTGC TGCTGCACAT
          AAGCACCCGT TGTAGCCCCT GCGTATGCCG CGCCGCGACG ACGACGTGTA
     +1   · M  L  T  T  T  V  T  L  T  L  L  A  Y  Q  A  T  K  I·
    1101  GTTGACCACC ACCGTGACGC TCACGCTGCT CGCCTACCAG GCCACCAAGA
          CAACTGGTGG TGGCACTGCG AGTGCGACGA GCGGATGGTC CGGTGGTTCT
     +1   · I  D  S  V  D  V  Y  A  A  S  V  L  G  Y  L  F  Y
    1151  TCGACTCGGT GGACGTGTAC GCGGCCTCTG TACTGGGCTA CCTGTTCTAC
          AGCTGAGCCA CCTGCACATG CGCCGGAGAC ATGACCCGAT GGACAAGATG
     +1     T  L  G  Q  V  F  L  F  C  V  F  G  N  S  L  I  E·
    1201  ACCCTGGGGC AGGTCTTCCT CTTCTGCGTC TTTGGAAACA GCCTCATTGA
          TGGGACCCCG TCCAGAAGGA GAAGACGCAG AAACCTTTGT CGGAGTAACT
     +1   · E  E  S  S  S  V  M  E  A  A  Y  S  C  H  W  Y  D  G·
    1251  AGAGAGCTCC TCGGTGATGG AGGCGGCGTA CAGCTGCCAC TGGTACGACG
          TCTCTCGAGG AGCCACTACC TCCGCCGCAT GTCGACGGTG ACCATGCTGC
     +1   · G  S  E  E  A  K  T  F  V  Q  I  V  C  Q  Q  C  Q
    1301  GCTCGGAGGA GGCCAAGACG TTCGTGCAGA TCGTGTGCCA GCAGTGTCAA
          CGAGCCTCCT CCGGTTCTGC AAGCACGTCT AGCACACGGT CGTCACAGTT
     +1     K  S  L  M  I  S  G  A  K  F  F  T  V  S  L  D  L·
    1351  AAGTCGCTCA TGATCTCCGG CGCCAAGTTC TTCACCGTCT CGCTCGATCT
          TTCAGCGAGT ACTAGAGGCC GCGGTTCAAG AAGTGGCAGA GCGAGCTAGA
     +1   · L  F  A  S  V  L  G  A  V  V  T  F  M  V  L  V  Q·
    1401  CTTCGCTTCG GTGCTGGGAG CCGTGGTGAC GTACTTCATG GTGCTGGTGC
          GAAGCGAAGC CACGACCCTC GGCACCACTG CATGAAGTAC CACGACCACG
     +1   · Q  L  K
    1451  AGCTCAAGTA G
          TCGAGTTCAT C
```

FIG. 5B (SEQ ID NOS: 7 + 8)

| SEQ ID NO: | | | Section 1 |
|---|---|---|---|
| | | (1) | 1        10        20        30        40        53 |
| 10 | Dmel. Or83b | (1) | MTTS‿‿ ‿‿TGLVADLMPN‿‿‿‿KYSGL‿H‿ ‿‿S ----F ‿‿‿ |
| 2 | Medfly Or83b | (1) | ----‿‿‿ K‿VGLVADLMPN‿‿‿MKYSGL‿H‿ ‿‿S ----‿F ‿‿‿ |
| 4 | Anopheles Or83b | (1) | --MQ ‿‿ K‿VGLVADLMPN‿‿‿‿‿‿‿G‿‿ FR‿VT‿PI---- ‿‿ ‿S‿WT |
| 6 | Helicoverpa Or83b | (1) | ----‿TKVK‿‿‿‿‿ DL‿PN‿‿ L‿M G‿F F‿‿HSEN GMSN‿ ‿‿‿ ST‿ |
| 8 | Locust Or83b | (1) | ------MQ‿PH‿L‿‿‿DLWPL ‿‿ ‿YS‿H MLE‿ ‿‿LT----A ‿‿‿‿‿ V |
| 12 | Consensus | (1) | MQPSKY GLVADLMPNIRLMQYSGHFM NYTGG A     LLRKIYSSVH |

| | | | Section 2 |
|---|---|---|---|
| | | (54) | 54       60        70        80        90        106 |
| 10 | Dmel. Or83b | (50) | ‿‿F ‿ ‿‿TF‿‿‿N A‿‿‿ ‿VNE‿ NTI‿T‿FF‿HC‿‿K‿‿YLA‿‿QK ‿‿ |
| 2 | Medfly Or83b | (46) | ‿‿‿‿ ‿‿‿LL ‿‿N‿AL‿‿ ‿VNE‿ NTI‿V‿FF‿HCL‿K‿‿YLA‿TQK ‿‿ |
| 4 | Anopheles Or83b | (48) | ‿A ‿‿ ‿‿FA‿‿GN‿AT‿‿ VNE‿ ‿NT‿‿‿‿FF‿‿‿‿‿S ‿K‿‿Y‿‿NSE‿ |
| 6 | Helicoverpa Or83b | (50) | A ‿ F H AC G N AKY ‿VNE‿ ‿NTI‿V‿‿F‿AH‿‿‿KLA ‿‿‿ ‿‿‿‿ |
| 8 | Locust Or83b | (44) | S‿‿‿ T‿‿AL A‿N‿IQR G VNE‿‿‿NTIT‿‿FL‿‿PL‿‿K‿A‿‿A‿R‿‿AF‿ |
| 12 | Consensus | (54) | LVLVLTQF  ILVNLA NADEVNELSANTITVLFFTH ITKFIYFAVNSKNFY |

| | | | Section 3 |
|---|---|---|---|
| | | (107) | 107       120       130       140       159 |
| 10 | Dmel. Or83b | (103) | RT‿N‿‿WN‿‿‿N HPL‿‿AESDARY‿‿‿‿IALAKMRK‿‿FF‿‿ML‿‿MA‿A‿A‿‿‿‿‿ |
| 2 | Medfly Or83b | (99) | RTLN‿‿WNG‿‿N HPL‿‿AESDAR‿ ‿‿IALAKMRK‿ ‿F‿‿ VML‿‿‿‿ SA‿A‿‿‿‿‿ |
| 4 | Anopheles Or83b | (101) | RT‿‿‿‿WN‿‿ N HPL‿‿AESDAR‿ ‿‿IALAKMRK‿ L‿‿‿ VL‿MA‿T‿‿ SA‿A‿‿‿‿‿ |
| 6 | Helicoverpa Or83b | (103) | RTLA‿‿WNQ‿ N HPL‿‿TESDARY ‿QEAL‿TKMR‿ YF‿CGM‿‿S‿‿ ‿‿M‿ ‿‿‿ |
| 8 | Locust Or83b | (97) | RT‿A‿TWN‿‿ NNHPL‿AE‿SQAR‿ ‿Q V MR‿ ‿ MYM‿ SV‿‿A‿S‿‿‿‿ ‿‿‿ |
| 12 | Consensus | (107) | RTLAIWNQSNSHPLFAESDARYHSIALAKMRKLL LVM TTVLSVVAWTTITF |

| | | | Section 4 |
|---|---|---|---|
| | | (160) | 160       170       180       190       200       212 |
| 10 | Dmel. Or83b | (156) | ‿G‿ S‿‿M‿V‿H -‿NS ‿P‿‿‿PRL‿‿‿ YP‿‿ASH‿GMF‿ ‿‿TA‿‿‿ Y‿ |
| 2 | Medfly Or83b | (152) | ‿G‿S‿‿FAF‿ -‿NS ‿‿TV‿‿PRL‿‿K‿ YP‿‿NAGS‿GMFY‿ ‿‿TA‿‿CY‿ L‿ |
| 4 | Anopheles Or83b | (154) | ‿G‿S‿ M‿TVL‿KA-‿N‿‿‿‿‿‿‿PRL‿‿‿‿ SWYP‿‿AMS‿PAY‿‿FS‿‿ I ‿Q‿‿ |
| 6 | Helicoverpa Or83b | (156) | ‿G‿S‿ M‿TNK -‿N‿‿‿‿EV ‿PRL‿‿‿ ‿YP‿‿AMSGTMY‿ ‿‿A‿‿‿‿‿ |
| 8 | Locust Or83b | (150) | M‿ ST E‿P‿P NA‿‿‿‿‿‿E‿‿ PRLM‿S ‿YP DASK‿GMGY ‿I Q ‿‿ |
| 12 | Consensus | (160) | FGESVK ‿ DKD TNETITVEIPRLPIKSWYPWNA SGM YIISFAFQIYWLL |

| | | | Section 5 |
|---|---|---|---|
| | | (213) | 213       220       230       240       250       265 |
| 10 | Dmel. Or83b | (208) | ‿‿‿H‿NE‿‿CDVM‿‿‿‿WL‿‿‿ACE‿QL‿‿‿LK‿‿M‿‿LMELSAS‿‿DTY‿‿PNS‿‿‿LFR |
| 2 | Medfly Or83b | (204) | ‿‿‿ H‿NE‿‿CDV ‿‿‿‿‿WL‿‿‿ACE‿QL‿‿‿LK‿‿M‿‿LMELSAS‿‿DTY‿‿P‿NS‿‿LFR |
| 4 | Anopheles Or83b | (206) | ‿‿‿ Q‿NL‿ADVMF‿CSWL‿‿LACE‿QL‿‿‿LK‿‿M‿ SLMELSAS‿‿ DTY‿‿P‿‿ QL‿ER |
| 6 | Helicoverpa Or83b | (208) | ‿‿MAI N‿ ‿MDV‿CSWL‿‿‿ACE‿QL‿‿‿LK IM‿‿LMELSA‿‿ ‿‿‿P‿ E‿‿ER |
| 8 | Locust Or83b | (203) | A ‿‿‿N‿MDV‿ E‿‿‿W‿L‿‿‿ACE‿QL‿‿KE‿M‿‿LMELSA L‿ DT‿‿VV‿H E‿‿‿R |
| 12 | Consensus | (213) | FSMVHSNL DVMFCSWLIFACEQLQHLKGIMKPLMELSASLDTYRPNSA LFR |

| | | | Section 6 |
|---|---|---|---|
| | | (266) | 266       280       290       300       318 |
| 10 | Dmel. Or83b | (261) | ‿‿N‿‿S‿‿‿‿‿‿‿E‿‿‿‿G----T‿‿‿ ‿G‿‿SS‿KA‿‿G‿Q‿R---‿A‿‿‿‿ |
| 2 | Medfly Or83b | (257) | ‿‿N‿‿‿‿‿‿N‿‿‿‿‿----T‿‿ ‿‿‿‿‿‿A‿W‿A‿FR---‿A‿‿‿ |
| 4 | Anopheles Or83b | (259) | ‿ S‿G‿‿SE‿‿ ‿N‿‿‿‿DV--- K‿F‿‿ ‿G‿‿SS‿KAD‿G‿Q‿R---‿A‿‿‿ |
| 6 | Helicoverpa Or83b | (261) | ‿SSTE-‿‿------‿‿I‿DT---V‿‿‿ RG‿‿S Q‿‿ ‿MTL‿RG--‿AGGR‿‿N |
| 8 | Locust Or83b | (256) | ‿A‿TLPTNEP YGMGP‿MSNGVTDG‿T RG‿‿S‿‿QR‿ S FN‿RSAA‿ ‿‿ RE |
| 12 | Consensus | (266) | ALSA SKSELI NEEKDP     DMDISGIYSSKADWGAQFR     APSTLQT |

FIG. 6A

```
SEQ ID NO:                                                                    Section 7
                     (319) 319       330       340       350       360       371
    10    Dmel. Or83b (307) GGN GGGNGLV    NGL  KQEMMVRSAIKYWVERHKHVVRLVAAIGDTY
     2    Medfly Or83b (302) NG--------M  T PNGL  KQEMMVRSAIKWVERHKHVVRLVAAIGDTY
     4  Anopheles Or83b (306) DEN -------RNG PNGL  KQEMMVRSAIKWVERHKHVVRL  IGDTY
     6 Helicoverpa Or83b (302) GQ---------  NP PNGL PKQEM ARSAIKWVERHKHVVRF  NIGDAY
     8    Locust Or83b (309) ADSG --AVTSAG  IGPNGL   QEM  VRSAIKWVERHKHVVRF  NIGDAY
    12      Consensus (319) F    G      NG NPNGLTKKQEMMVRSAIKYWVERHKHVVRLVAAIGDTY
                                                                              Section 8
                     (372) 372       380       390       400       410       424
    10    Dmel. Or83b (360) G  ALLLHMLTSTI  TLLAYQATKI  GVNV YAF   GYL YALAQVFHFCIFG
     2    Medfly Or83b (347) G  ALLLHMLTSTI TLLAYQATKI   NV YAF    GYL YALAQVFHFCIFG
     4  Anopheles Or83b (352) GPALLLHMLTSTI KTLLAYQATKID NV  L     GYL QV AQVFHFCIFG
     6 Helicoverpa Or83b (346) GTALLLHML    T TLLAYQATKIN  V  T    GYLCSY   QV  FCIFG
     8    Locust Or83b (360) G  ALLLHML    T TLLAYQATKIDSVDV YAA   GYL YT   QV  FCIFG
    12      Consensus (372) GAALLLHMLTSTI LTLLAYQATKI GVNVYAFTVIGYL YALAQVFHFCIFG
                                                                              Section 9
                     (425) 425       430       440       450       460       477
    10    Dmel. Or83b (413) NRLIEESSSVMEAAYSCHWYDGSEEAKTFVQIVCQQCQKAMSISGAKFFTVSL
     2    Medfly or83b (400) NRLIEESSSVMEAAYSCHWYDGSEEAKTFVQIVCQQCQKAMSISGAKFFTVSL
     4  Anopheles Or83b (405) NRLIEESSSVMEAAYSCHWYDGSEEAKTFVQIVCQQCQKAM ISGAKFFTVSL
     6 Helicoverpa Or83b (399) NRLIEESSSVMEAAYSCQWYDGSEEAKTFVQIVCQQCQKAMSISGAKFFTVSL
     8    Locust Or83b (413) NSLIEESSSVMEAAYSCHWYDGSEEAKTFVQIVCQQCQK  MISGAKFFTVSL
    12      Consensus (425) NRLIEESSSVMEAAYSCHWYDGSEEAKTFVQIVCQQCQKAMSISGAKFFTVSL
                                                                              Section 10
                     (478) 478       498
    10    Dmel. Or83b (466) DLFASVLGAVVTYFMVLVQLK
     2    Medfly Or83b (453) DLFASVLGAVVTYFMVLVQLK
     4  Anopheles Or83b (458) DLFASVLGAVVTYFMVLVQLK
     6 Helicoverpa Or83b (452) DLFASVLGAVVTYFMVLVQLK
     8    Locust Or83b (466) DLFASVLGAVVTYFMVLVQLK
    12      Consensus (478) DLFASVLGAVVTYFMVLVQLK
```

FIG. 6B

SEQUENCE LISTING

```
<160> NUMBER OF SEQ ID NOS: 20

<210> SEQ ID NO 1
<211> LENGTH: 1422
<212> TYPE: DNA
<213> ORGANISM: Ceratitis capitata

<400> SEQUENCE: 1
atgcagccga gtaaatatgt tggcctcgtg gccgatttga tgccgaacat acgtctgatg      60
aagtactcgg gcttgttcat gcacaacttc actggcggtt ccggactctt taagaaaatt     120
tactcatcca tgcatttggt tttggttttg gtgcaatttc tattgatact ggtgaatttg     180
gcattaaatg cggaggaggt gaatgagttg tccggcaata caataaccgt gctcttcttt     240
actcattgca taacgaaatt catctatttg gccgttacac agaagcagtt ctacagaacg     300
ttgaatatat ggaatcaagt gaattcgcat ccattgttcg ccgagtcgga tgcgcgctac     360
cactcgattg cgctcgccaa aatgcgaaag ctcttcacac tggttatgct caccaccgtc     420
gtttcagctg tggcttggac tactattaca ttcttcggtg agagcgttaa atttgccttc     480
gacaaggata ccaactcttc aataaccgtt gaaattccac gcttgcccat taaatccttt     540
tacccgtgga atgccggctc gggcatgttt tacataatca gtttcgcttt tcaatgctac     600
tatctgctct tctctatggt tcactctaat ttatgtgatg tgctcttctg ttcgtggttg     660
attttcgcct gcgagcagtt acaacacctg aaaggtatca tgaaaccgtt gatggagctg     720
tcagcctcat tggacaccta tcggccaaat tcggctgcac tatttcgttc gctatcggcc     780
aattctaaat cggaattgat aaataatgag gagaaggaac ccactgatct ggacgttagt     840
ggcatttaca gctccaaagc agattggggc gcacagtttc gtgcaccatc aacgttacaa     900
accttcaatg gcatgaatgg taccaatccg aatggtttga ccagaaagca ggagatgatg     960
gtgcgcagtg ccattaaata ttgggttgaa cgacacaagc acgttgtaag attagttgca    1020
```

```
gctatcggcg atacatatgg cggcgctttg ttgttgcaca tgttgacatc caccattatg    1080
ctaacgttgt tggcttatca ggccacgaag atcaccggcg tcaatgttta cgccttcacc    1140
acggtcggtt atttgtgcta tgctttggcg caggtatttc attttttgcat atttggcaat   1200 cggctgattg aggagagctc atccgttatg gaggcagcct actcctgcca ttggtatgat    1260
ggctccgagg aggccaagac ttttgtccag atcgtttgcc agcagtgcca aaaggcgatg    1320
tccatatcag gagcgaagtt tttcaccgtc tcattggatt tgtttgcatc ggttcttggc    1380
gctgtggtca cctatttcat ggtgttggta caattgaagt ga                       1422
```

<210> SEQ ID NO 2
<211> LENGTH: 473
<212> TYPE: PRT
<213> ORGANISM: Ceratitis capitata

<400> SEQUENCE: 2

```
Met Gln Pro Ser Lys Tyr Val Gly Leu Val Ala Asp Leu Met Pro Asn
1               5                   10                  15

Ile Arg Leu Met Lys Tyr Ser Gly Leu Phe Met His Asn Phe Thr Gly
        20                  25                  30

Gly Ser Gly Leu Phe Lys Lys Ile Tyr Ser Ser Met His Leu Val Leu
    35                  40                  45

Val Leu Val Gln Phe Leu Leu Ile Leu Val Asn Leu Ala Leu Asn Ala
50                  55                  60

Glu Glu Val Asn Glu Leu Ser Gly Asn Thr Ile Thr Val Leu Phe Phe
65                  70                  75                  80

Thr His Cys Ile Thr Lys Phe Ile Tyr Leu Ala Val Thr Gln Lys Gln
            85                  90                  95

Phe Tyr Arg Thr Leu Asn Ile Trp Asn Gln Val Asn Ser His Pro Leu
        100                 105                 110

Phe Ala Glu Ser Asp Ala Arg Tyr His Ser Ile Ala Leu Ala Lys Met
    115                 120                 125

Arg Lys Leu Phe Thr Leu Val Met Leu Thr Thr Val Val Ser Ala Val
130                 135                 140

Ala Trp Thr Thr Ile Thr Phe Phe Gly Glu Ser Val Lys Phe Ala Phe
145                 150                 155                 160

Asp Lys Asp Thr Asn Ser Ser Ile Thr Val Glu Ile Pro Arg Leu Pro
            165                 170                 175

Ile Lys Ser Phe Tyr Pro Trp Asn Ala Gly Ser Gly Met Phe Tyr Ile
        180                 185                 190

Ile Ser Phe Ala Phe Gln Cys Tyr Tyr Leu Leu Phe Ser Met Val His
    195                 200                 205

Ser Asn Leu Cys Asp Val Leu Phe Cys Ser Trp Leu Ile Phe Ala Cys
210                 215                 220

Glu Gln Leu Gln His Leu Lys Gly Ile Met Lys Pro Leu Met Glu Leu
225                 230                 235                 240

Ser Ala Ser Leu Asp Thr Tyr Arg Pro Asn Ser Ala Ala Leu Phe Arg
            245                 250                 255

Ser Leu Ser Ala Asn Ser Lys Ser Glu Leu Ile Asn Asn Glu Glu Lys
        260                 265                 270

Glu Pro Thr Asp Leu Asp Val Ser Gly Ile Tyr Ser Ser Lys Ala Asp
    275                 280                 285

Trp Gly Ala Gln Phe Arg Ala Pro Ser Thr Leu Gln Thr Phe Asn Gly
290                 295                 300
```

```
Met Asn Gly Thr Asn Pro Asn Gly Leu Thr Arg Lys Gln Glu Met Met
305                 310                 315                 320

Val Arg Ser Ala Ile Lys Tyr Trp Val Glu Arg His Lys His Val Val
            325                 330                 335

Arg Leu Val Ala Ala Ile Gly Asp Thr Tyr Gly Gly Ala Leu Leu Leu
340                 345                 350

His Met Leu Thr Ser Thr Ile Met Leu Thr Leu Ala Tyr Gln Ala
355                 360                 365

Thr Lys Ile Thr Gly Val Asn Val Tyr Ala Phe Thr Thr Val Gly Tyr
370                 375                 380

Leu Cys Tyr Ala Leu Ala Gln Val Phe His Phe Cys Ile Phe Gly Asn
385                 390                 395                 400

Arg Leu Ile Glu Glu Ser Ser Ser Val Met Glu Ala Ala Tyr Ser Cys
405                 410                 415

His Trp Tyr Asp Gly Ser Glu Glu Ala Lys Thr Phe Val Gln Ile Val
420                 425                 430

Cys Gln Gln Cys Gln Lys Ala Met Ser Ile Ser Gly Ala Lys Phe Phe
435                 440                 445

Thr Val Ser Leu Asp Leu Phe Ala Ser Val Leu Gly Ala Val Val Thr
450                 455                 460

Tyr Phe Met Val Leu Val Gln Leu Lys
465                 470

<210> SEQ ID NO 3
<211> LENGTH: 1419
<212> TYPE: DNA
<213> ORGANISM: Helicoverpa zea

<400> SEQUENCE: 3
atgaccaagg tgaaggccca gggcctcgtg tcagacttga tgcccaacat caagctgatg      60
cagatggccg ggcatttcct cttcaattac cattcagaaa atgctggcat gtcaaacctt     120
ctccgtaaga tctacgcgag tactcatgcc atcttgatct ttatccacta tgcttgtatg     180
ggcatcaaca tggcgaaata ctccgatgaa gtcaacgagc tgacggcgaa taccatcact     240
gttctattct cgctcatac tatcatcaag cttgctttct tcgccttaaa ttctaagagc     300
ttctatagga ccctggcagt atggaaccag tcgaacagtc acccgctgtt cacggagtca     360
gatgcccgct accaccagat cgcgctcacc aagatgagga ggctgctgta cttcatctgc     420
gggatgactg tcctctctgt tatcagctgg gtaaccctca cattcttcgg cgagtcagtg     480
cgcatggtga cgaacaagga accaacgag accctgacgg aggtggtgcc ccggctacct     540
ctgaaggcct ggtaccccct caatgctatg agcgggacta tgtatattgt ggcgttcgct     600
tttcaggtat actggctcct attctcaatg ccatagcga acctcatgga tgtcatgttc     660
tgttcctggc tgatcttcgc gtgtgaacag ctgcagcatc tgaaggctat catgaaacct     720
ctcatggagt tgagcgcctc cttggacact taccggccta atactgctga gctgttccga     780
gcttcttcta ctgagaaatc cgaaaagatc cccgacacgg tagacatgga catccgcggc     840
atctactcca cgcagcaaga cttcggcatg acactgcgag gtgctggtgg aagactccag     900
aacttcggcc agcagaaccc caaccctaac ggcttgaccc caagcagga gatgctggcc      960 aggtctgcta tcaagtactg ggtggagagg cataagcatg tcgtcagact agtggcatca    1020
attggagaca cgtatggtac cgccctgctg ttccacatgt tggtgtctac catcacgctc    1080
accctgctgg cctaccaagc tactaagatc aacggaatca acgtgtatgc tttcagtaca    1140
```

```
attggatact tgagttacac tctcggtcaa gtgttccact tctgcatttt cggaaatagg    1200
ctcattgaag agagctcatc agtaatggag gcagcttact cctgccagtg gtatgacggc    1260
tccgaggaag cgaagacatt cgtgcagatc gtctgccaac agtgccagaa agctatgagc    1320
atctccggag ccaagttctt cacggtgtcc cttgatttgt tcgcttcggt tcttggagcc    1380
gtggttacct acttcatggt gttggtacaa ctcaagtaa                           1419
```

<210> SEQ ID NO 4
<211> LENGTH: 472
<212> TYPE: PRT
<213> ORGANISM: Helicoverpa zea

<400> SEQUENCE: 4

```
Met Thr Lys Val Lys Ala Gln Gly Leu Val Ser Asp Leu Met Pro Asn
1               5                   10                  15

Ile Lys Leu Met Gln Met Ala Gly His Phe Leu Phe Asn Tyr His Ser
            20                  25                  30

Glu Asn Ala Gly Met Ser Asn Leu Leu Arg Lys Ile Tyr Ala Ser Thr
        35                  40                  45

His Ala Ile Leu Ile Phe Ile His Tyr Ala Cys Met Gly Ile Asn Met
    50                  55                  60

Ala Lys Tyr Ser Asp Glu Val Asn Glu Leu Thr Ala Asn Thr Ile Thr
65                  70                  75                  80

Val Leu Phe Phe Ala His Thr Ile Ile Lys Leu Ala Phe Phe Ala Leu
                85                  90                  95

Asn Ser Lys Ser Phe Tyr Arg Thr Leu Ala Val Trp Asn Gln Ser Asn
            100                 105                 110

Ser His Pro Leu Phe Thr Glu Ser Asp Ala Arg Tyr His Gln Ile Ala
        115                 120                 125

Leu Thr Lys Met Arg Arg Leu Leu Tyr Phe Ile Cys Gly Met Thr Val
    130                 135                 140

Leu Ser Val Ile Ser Trp Val Thr Leu Thr Phe Phe Gly Glu Ser Val
145                 150                 155                 160

Arg Met Val Thr Asn Lys Glu Thr Asn Glu Thr Leu Thr Glu Val Val
                165                 170                 175

Pro Arg Leu Pro Leu Lys Ala Trp Tyr Pro Phe Asn Ala Met Ser Gly
            180                 185                 190

Thr Met Tyr Ile Val Ala Phe Ala Phe Gln Val Tyr Trp Leu Leu Phe
        195                 200                 205

Ser Met Ala Ile Ala Asn Leu Met Asp Val Met Phe Cys Ser Trp Leu
    210                 215                 220

Ile Phe Ala Cys Glu Gln Leu Gln His Leu Lys Ala Ile Met Lys Pro
225                 230                 235                 240

Leu Met Glu Leu Ser Ala Ser Leu Asp Thr Tyr Arg Pro Asn Thr Ala
                245                 250                 255

Glu Leu Phe Arg Ala Ser Ser Thr Glu Lys Ser Glu Lys Ile Pro Asp
            260                 265                 270

Thr Val Asp Met Asp Ile Arg Gly Ile Tyr Ser Thr Gln Gln Asp Phe
        275                 280                 285

Gly Met Thr Leu Arg Gly Ala Gly Gly Arg Leu Gln Asn Phe Gly Gln
    290                 295                 300

Gln Asn Pro Asn Pro Asn Gly Leu Thr Pro Lys Gln Glu Met Leu Ala
305                 310                 315                 320

Arg Ser Ala Ile Lys Tyr Trp Val Glu Arg His Lys His Val Val Arg
```

```
                325                 330                 335
Leu Val Ala Ser Ile Gly Asp Thr Tyr Gly Thr Ala Leu Leu Phe His
340                 345                 350

Met Leu Val Ser Thr Ile Thr Leu Thr Leu Leu Ala Tyr Gln Ala Thr
355                 360                 365

Lys Ile Asn Gly Ile Asn Val Tyr Ala Phe Ser Thr Ile Gly Tyr Leu
370                 375                 380

Ser Tyr Thr Leu Gly Gln Val Phe His Phe Cys Ile Phe Gly Asn Arg
385                 390                 395                 400

Leu Ile Glu Glu Ser Ser Val Met Glu Ala Ala Tyr Ser Cys Gln
405                 410                 415

Trp Tyr Asp Gly Ser Glu Glu Ala Lys Thr Phe Val Gln Ile Val Cys
420                 425                 430

Gln Gln Cys Gln Lys Ala Met Ser Ile Ser Gly Ala Lys Phe Phe Thr
435                 440                 445

Val Ser Leu Asp Leu Phe Ala Ser Val Leu Gly Ala Val Val Thr Tyr
450                 455                 460

Phe Met Val Leu Val Gln Leu Lys
465                 470

<210> SEQ ID NO 5
<211> LENGTH: 1437
<212> TYPE: DNA
<213> ORGANISM: Anopheles gambiae

<400> SEQUENCE: 5
atgcaagtcc agccgaccaa gtacgtcggc ctcgtcgccg acctgatgcc gaacattcgg    60
ctgatgcagg ccagcggtca ctttctgttc cgctacgtca ccggcccgat actgatccgc   120
aaggtgtact cctggtggac gctcgccatg gtgctgatcc agttcttcgc catcctcggc   180
aacctggcga cgaacgcgga cgacgtgaac gagctgaccg ccaacacgat cacgaccctg   240
ttcttcacgc actcggtcac caagttcatc tactttgcgg tcaactcgga gaacttctac   300
cggacgctcg ccatctggaa ccagaccaac acgcaccccg tgtttgccga atcggacgcc   360
cggtaccatt cgattgcgct cgccaagatg cggaagctgc tggtgctggt gatggccacc   420
accgtcctgt cggttgtcgc ctgggttacg ataacatttt cggcgagag cgtcaagacc   480 gtgctcgata aggcaaccaa cgagacgtac acggtggata ccccggct gcccatcaag   540 tcctggtatc cgtggaatgc aatgagcgga ccggcgtaca ttttctcttt catctaccag   600
atttacttcc tgctgttttc gatggtccag agcaacctcg cggatgtcat gttctgctcc   660
tggttgctgc tagcctgcga gcagctgcaa catttgaagg gtattatgcg atcgctgatg   720
gagctttcgg cctcgctgga cacctaccgg cccaactctt cgcaactgtt ccgagcaatt   780
tcagccggtt ccaaatcgga gctgatcatc aacgaagaaa aggatccgga cgttaaggac   840
tttgatctga gcggcatcta cagctcgaag gcggactggg gcgcccagtt ccgtgcgccg   900
tcgacgctgc aaacgttcga cgagaatggc aggaacggaa atccgaacgg gcttacccgg   960
aagcaggaaa tgatggtgcg cagcgccatc aagtactggg tcgagcggca caagcacgtt  1020
gtacgtctcg tttcagcaat cggagatacg tacggtcctg ccctgctgct gcacatgctg  1080
acttccacca tcaagctgac gctgctcgcc taccaggcaa cgaaaatcga cggtgtcaac  1140
gtgtacggat tgaccgtaat cggatatttg tgctacgcgt tggctcaggt tttcctgttt  1200
tgcatctttg gcaatcggct catcgaggag agctcatccg tgatggaggc ggcctattcc  1260
```

```
tgccactggt acgacgggtc cgaggaggca aaaaccttcg tccagatcgt ttgtcagcag    1320
tgccagaagg cgatgactat ttccggagcc aagtttttca ccgtttcgct cgatctgttt    1380
gcttcggttc ttggagccgt tgtcacctac ttcatggtgc tggtrcagct gaagtaa       1437
```

<210> SEQ ID NO 6
<211> LENGTH: 478
<212> TYPE: PRT
<213> ORGANISM: Anopheles gambiae

<400> SEQUENCE: 6

```
Met Gln Val Gln Pro Thr Lys Tyr Val Gly Leu Val Ala Asp Leu Met
1               5                   10                  15

Pro Asn Ile Arg Leu Met Gln Ala Ser Gly His Phe Leu Phe Arg Tyr
            20                  25                  30

Val Thr Gly Pro Ile Leu Ile Arg Lys Val Tyr Ser Trp Trp Thr Leu
        35                  40                  45

Ala Met Val Leu Ile Gln Phe Phe Ala Ile Leu Gly Asn Leu Ala Thr
    50                  55                  60

Asn Ala Asp Asp Val Asn Glu Leu Thr Ala Asn Thr Ile Thr Thr Leu
65                  70                  75                  80

Phe Phe Thr His Ser Val Thr Lys Phe Ile Tyr Phe Ala Val Asn Ser
                85                  90                  95

Glu Asn Phe Tyr Arg Thr Leu Ala Ile Trp Asn Gln Thr Asn Thr His
            100                 105                 110

Pro Leu Phe Ala Glu Ser Asp Ala Arg Tyr His Ser Ile Ala Leu Ala
        115                 120                 125

Lys Met Arg Lys Leu Leu Val Leu Val Met Ala Thr Thr Val Leu Ser
    130                 135                 140

Val Val Ala Trp Val Thr Ile Thr Phe Phe Gly Glu Ser Val Lys Thr
145                 150                 155                 160

Val Leu Asp Lys Ala Thr Asn Glu Thr Tyr Thr Val Asp Ile Pro Arg
                165                 170                 175

Leu Pro Ile Lys Ser Trp Tyr Pro Trp Asn Ala Met Ser Gly Pro Ala
            180                 185                 190

Tyr Ile Phe Ser Phe Ile Tyr Gln Ile Tyr Phe Leu Leu Phe Ser Met
        195                 200                 205

Val Gln Ser Asn Leu Ala Asp Val Met Phe Cys Ser Trp Leu Leu Leu
    210                 215                 220

Ala Cys Glu Gln Leu Gln His Leu Lys Gly Ile Met Arg Ser Leu Met
225                 230                 235                 240

Glu Leu Ser Ala Ser Leu Asp Thr Tyr Arg Pro Asn Ser Ser Gln Leu
                245                 250                 255

Phe Arg Ala Ile Ser Ala Gly Ser Lys Ser Glu Leu Ile Ile Asn Glu
            260                 265                 270

Glu Lys Asp Pro Asp Val Lys Asp Phe Asp Leu Ser Gly Ile Tyr Ser
        275                 280                 285

Ser Lys Ala Asp Trp Gly Ala Gln Phe Arg Ala Pro Ser Thr Leu Gln
    290                 295                 300

Thr Phe Asp Glu Asn Gly Arg Asn Gly Asn Pro Asn Gly Leu Thr Arg
305                 310                 315                 320

Lys Gln Glu Met Met Val Arg Ser Ala Ile Lys Tyr Trp Val Glu Arg
                325                 330                 335

His Lys His Val Val Arg Leu Val Ser Ala Ile Gly Asp Thr Tyr Gly
            340                 345                 350
```

```
Pro Ala Leu Leu Leu His Met Leu Thr Ser Thr Ile Lys Leu Thr Leu
355                 360                 365

Leu Ala Tyr Gln Ala Thr Lys Ile Asp Gly Val Asn Val Tyr Gly Leu
370                 375                 380

Thr Val Ile Gly Tyr Leu Cys Tyr Ala Leu Ala Gln Val Phe Leu Phe
385                 390                 395                 400

Cys Ile Phe Gly Asn Arg Leu Ile Glu Glu Ser Ser Ser Val Met Glu
405                 410                 415

Ala Ala Tyr Ser Cys His Trp Tyr Asp Gly Ser Glu Glu Ala Lys Thr
420                 425                 430

Phe Val Gln Ile Val Cys Gln Gln Cys Gln Lys Ala Met Thr Ile Ser
435                 440                 445

Gly Ala Lys Phe Phe Thr Val Ser Leu Asp Leu Phe Ala Ser Val Leu
450                 455                 460

Gly Ala Val Val Thr Tyr Phe Met Val Leu Val Gln Leu Lys
465                 470                 475

<210> SEQ ID NO 7
<211> LENGTH: 1461
<212> TYPE: DNA
<213> ORGANISM: Schistocerca americana

<400> SEQUENCE: 7
atgcagaagc cgcatgggct ggtggcggac ctgtggccgc tgatccgcat ggtgcagtac      60
tcgggccact ggatgctcga gtacagcggc ggcctcacgg ccctgcgcgc catctacagc     120
tcggtcgtgt ccgtcctggt cgtgacgcag ttcgcgctca tggccgtcaa cctcatccag     180
cggtccggcg acgtcaacga gctggcggcc aacaccatca cggtgctctt cttcctgcac     240
cccatcacca gttcgcccta cttcgcggtg cgctccaagg ccttctaccg cacgctcgcc     300
acatggaacc agtccaacaa ccacccgctg tttgcagagt cacaggcgcg cttccaccag     360
ctgtccgtgg tgcgcatgcg ccggctcgtg atgtacgtgg tgtccgtgac ggcgctcagc     420
gtcgtgtcct ggacctccat caccttcatg ggcgactcga gcgggaggt gcccgacccc     480
gacaacgcca acgagaccat caccgaggag gtccccaggc tcatgatcag cacctggtac     540
ccgttcgacg cctcttctgg tatgggatac atgctcgcct tcatataccca gctgtactgg     600
ctgacggcga cgctgatgca ctccaacctg atggacgtga tgttctgctg ctggctcatc     660
tacgcgtgtg agcagctggt gcacctcaag gagatcatga agccgctcat ggagctcagc     720
gccacgctgg acaccgtggt gccgcacacc agcgagctct ccgagccgc ctccacactg     780
cccaccaacg agccactcta cgggatgggg ccagacatga gcaacggcgt gacggacggc     840
atgacgatcc gcggcatcta cagcagccag cgcgacttct cgggcttcaa ccggcgctcg     900
gcggcgctgt cgacggtgcg cgaggccgat tcgggcggcg ccgtcacctc cgccggcggc     960
atcgggccca acgggctcag caagcgccag agatgctgg tgcgctccgc catcaagtac    1020
tgggtcgagc gacacaagca cgtggtcagg ttcgtgggca acatcgggga cgcatacggc    1080
gcggcgctgc tgctgcacat gttgaccacc accgtgacgc tcacgctgct cgcctaccag    1140
gccaccaaga tcgactcggt ggacgtgtac gcggcctctg tactgggcta cctgttctac    1200
accctggggc aggtcttcct cttctgcgtc tttggaaaca gcctcattga agagagctcc    1260
tcggtgatgg aggcggcgta cagctgccca tggtacgacg gctcggagga ggccaagacg    1320
ttcgtgcaga tcgtgtgcca gcagtgtcaa aagtcgctca tgatctccgg cgccaagttc    1380
```

```
ttcaccgtct cgctcgatct cttcgcttcg gtgctgggag ccgtggtgac gtacttcatg   1440
gtgctggtgc agctcaagta g                                             1461
```

<210> SEQ ID NO 8
<211> LENGTH: 486
<212> TYPE: PRT
<213> ORGANISM: Schistocerca americana

<400> SEQUENCE: 8

```
Met Gln Lys Pro His Gly Leu Val Ala Asp Leu Trp Pro Leu Ile Arg
1               5                   10                  15

Met Val Gln Tyr Ser Gly His Trp Met Leu Glu Tyr Ser Gly Gly Leu
            20                  25                  30

Thr Ala Leu Arg Ala Ile Tyr Ser Ser Val Val Ser Val Leu Val Val
        35                  40                  45

Thr Gln Phe Ala Leu Met Ala Val Asn Leu Ile Gln Arg Ser Gly Asp
    50                  55                  60

Val Asn Glu Leu Ala Ala Asn Thr Ile Thr Val Leu Phe Phe Leu His
65                  70                  75                  80

Pro Ile Thr Lys Phe Ala Tyr Phe Ala Val Arg Ser Lys Ala Phe Tyr
                85                  90                  95

Arg Thr Leu Ala Thr Trp Asn Gln Ser Asn Asn His Pro Leu Phe Ala
            100                 105                 110

Glu Ser Gln Ala Arg Phe His Gln Leu Ser Val Val Arg Met Arg Arg
        115                 120                 125

Leu Val Met Tyr Val Val Ser Val Thr Ala Leu Ser Val Val Ser Trp
    130                 135                 140

Thr Ser Ile Thr Phe Met Gly Asp Ser Thr Arg Glu Val Pro Asp Pro
145                 150                 155                 160

Asp Asn Ala Asn Glu Thr Ile Thr Glu Glu Val Pro Arg Leu Met Ile
                165                 170                 175

Ser Thr Trp Tyr Pro Phe Asp Ala Ser Ser Gly Met Gly Tyr Met Leu
            180                 185                 190

Ala Phe Ile Tyr Gln Leu Tyr Trp Leu Thr Ala Thr Leu Met His Ser
        195                 200                 205

Asn Leu Met Asp Val Met Phe Cys Cys Trp Leu Ile Tyr Ala Cys Glu
    210                 215                 220

Gln Leu Val His Leu Lys Glu Ile Met Lys Pro Leu Met Glu Leu Ser
225                 230                 235                 240

Ala Thr Leu Asp Thr Val Val Pro His Thr Ser Glu Leu Phe Arg Ala
                245                 250                 255

Ala Ser Thr Leu Pro Thr Asn Glu Pro Leu Tyr Gly Met Gly Pro Asp
            260                 265                 270

Met Ser Asn Gly Val Thr Asp Gly Met Thr Ile Arg Gly Ile Tyr Ser
        275                 280                 285

Ser Gln Arg Asp Phe Ser Gly Phe Asn Arg Arg Ser Ala Ala Leu Ser
    290                 295                 300

Thr Val Arg Glu Ala Asp Ser Gly Gly Ala Val Thr Ser Ala Gly Gly
305                 310                 315                 320

Ile Gly Pro Asn Gly Leu Ser Lys Arg Gln Glu Met Leu Val Arg Ser
                325                 330                 335

Ala Ile Lys Tyr Trp Val Glu Arg His Lys His Val Val Arg Phe Val
            340                 345                 350

Gly Asn Ile Gly Asp Ala Tyr Gly Ala Ala Leu Leu Leu His Met Leu
```

```
                355              360               365
Thr Thr Thr Val Thr Leu Thr Leu Leu Ala Tyr Gln Ala Thr Lys Ile
370                 375                 380

Asp Ser Val Asp Val Tyr Ala Ala Ser Val Leu Gly Tyr Leu Phe Tyr
385                 390                 395                 400

Thr Leu Gly Gln Val Phe Leu Phe Cys Val Phe Gly Asn Ser Leu Ile
405                 410                 415

Glu Glu Ser Ser Ser Val Met Glu Ala Ala Tyr Ser Cys His Trp Tyr
420                 425                 430

Asp Gly Ser Glu Glu Ala Lys Thr Phe Val Gln Ile Val Cys Gln Gln
435                 440                 445

Cys Gln Lys Ser Leu Met Ile Ser Gly Ala Lys Phe Phe Thr Val Ser
450                 455                 460

Leu Asp Leu Phe Ala Ser Val Leu Gly Ala Val Val Thr Tyr Phe Met
465                 470                 475                 480

Val Leu Val Gln Leu Lys
485

<210> SEQ ID NO 9
<211> LENGTH: 1917
<212> TYPE: DNA
<213> ORGANISM: Drosophila melanogaster

<400> SEQUENCE: 9
ggcacgagct ggttccggaa agcctcatat ctcgtatctt aaagtatccc ggttaagcct      60
taaagagtga atgattgcc tagacgattg ctgcattact ggcactcaat taacccaagt     120
gtaccagaca caattacat ttgtattttt aaagttcaat agcaaggatg acaacctcga     180
tgcagccgag caagtacacg ggcctggtcg ccgacctgat gcccaacatc cgggcgatga     240
agtactccgg cctgttcatg cacaacttca cgggcggcag tgccttcatg aagaaggtgt     300
actcctccgt gcacctggtg ttcctcctca tgcagttcac cttcatcctg gtcaacatgg     360
ccctgaacgc cgaggaggtc aacgagctgt cgggcaacac gatcacgacc ctcttcttca     420
cccactgcat cacgaagttt atctacctgg ctgttaacca aagaatttc tacagaacat     480
tgaatatatg gaaccaggtg aacacgcatc cctgttcgc cgagtcggat gctcgttacc     540
attcgatcgc actggcgaag atgaggaagc tgttctttct ggtgatgctg accacagtcg     600
cctcggccac cgcctggacc acgatcacct tctttggcga cagcgtaaaa atggtggtgg     660
accatgagac gaactccagc atcccggtgg agataccccg gctgccgatt aagtccttct     720
acccgtggaa cgccagccac ggcatgttct acatgatcag cttttgccttt cagatctact     780
acgtgctctt ctcgatgatc cactccaatc tatgcgacgt gatgttctgc tcttggctga     840
tattcgcctg cgagcagctg cagcacttga agggcatcat gaagccgctg atggagctgt     900
ccgcctcgct ggacacctac aggcccaact cggcggccct cttcaggtcc ctgtcggcca     960
actccaagtc ggagctaatt cataatgaag aaaaggatcc cggcaccgac atggacatgt    1020
cgggcatcta cagctcgaaa gcggattggg gcgctcagtt cgagcaccc tcgacactgc    1080
agtcctttgg cggaacgggg gcggaggca acgggttggt gaacggcgct aatcccaacg    1140
ggctgaccaa aaagcaggag atgatggtgc gcagtgccat caagtactgg gtcgagcggc    1200
acaagcacgt ggtgcgactg gtggctgcca tcggcgatac ttacggagcc gccctcctcc    1260
tccacatgct gacctcgacc atcaagctga ccctgctggc ataccaggcc accaaaatca    1320
acggagtgaa tgtctacgcc ttcacagtcg tcggatacct aggatacgcg ctggcccagg    1380
```

-continued

```
tgttccactt tgcatctttt ggcaatcgtc tgattgaaga gagttcatcc gtcatggagg    1440
ccgcctactc gtgccactgg tacgatggct ccgaggaggc caagaccttc gtccagatcg    1500
tgtgccagca gtgccagaag gcgatgagca tatcgggagc gaaattcttc accgtctccc    1560
tggatttgtt tgcttcggtt ctgggtgccg tcgtcaccta ctttatggtg ctggtgcagc    1620
tcaagtaagt tgctgcgaag ctgatggatt tttgtaccag aaaagcgaat gccaagaagc    1680
cacctaccgc cccttgcccc ctccgcactg tgcaaccagc aatatcacag agcaattata    1740
acgcaaatta tatattttat acctgcgacg agcgagcctc gtggggcata atggagacat    1800 tctgggcac atagaagcct gcaaatactt atcgattttg tacacgcgta gagcttttaa    1860
tgtaaactca agatgcaaac taaataaatg tgtagtgaaa aaaaaaaaaa aaaaaaa      1917
```

<210> SEQ ID NO 10
<211> LENGTH: 486
<212> TYPE: PRT
<213> ORGANISM: Drosophila melanogaster

<400> SEQUENCE: 10

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
    130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
            260                 265                 270

Asn Glu Glu Lys Asp Pro Gly Thr Asp Met Asp Met Ser Gly Ile Tyr
```

-continued

```
                275                 280                 285
Ser Ser Lys Ala Asp Trp Gly Ala Gln Phe Arg Ala Pro Ser Thr Leu
290                 295                 300

Gln Ser Phe Gly Gly Asn Gly Gly Gly Asn Gly Leu Val Asn Gly
305                 310                 315                 320

Ala Asn Pro Asn Gly Leu Thr Lys Lys Gln Glu Met Met Val Arg Ser
325                 330                 335

Ala Ile Lys Tyr Trp Val Glu Arg His Lys His Val Val Arg Leu Val
340                 345                 350

Ala Ala Ile Gly Asp Thr Tyr Gly Ala Ala Leu Leu Leu His Met Leu
355                 360                 365

Thr Ser Thr Ile Lys Leu Thr Leu Leu Ala Tyr Gln Ala Thr Lys Ile
370                 375                 380

Asn Gly Val Asn Val Tyr Ala Phe Thr Val Val Gly Tyr Leu Gly Tyr
385                 390                 395                 400

Ala Leu Ala Gln Val Phe His Phe Cys Ile Phe Gly Asn Arg Leu Ile
405                 410                 415

Glu Glu Ser Ser Ser Val Met Glu Ala Ala Tyr Ser Cys His Trp Tyr
420                 425                 430

Asp Gly Ser Glu Glu Ala Lys Thr Phe Val Gln Ile Val Cys Gln Gln
435                 440                 445

Cys Gln Lys Ala Met Ser Ile Ser Gly Ala Lys Phe Phe Thr Val Ser
450                 455                 460

Leu Asp Leu Phe Ala Ser Val Leu Gly Ala Val Val Thr Tyr Phe Met
465                 470                 475                 480

Val Leu Val Gln Leu Lys
485

<210> SEQ ID NO 11
<211> LENGTH: 498
<212> TYPE: PRT
<213> ORGANISM: Unknown
<220> FEATURE:
<223> OTHER INFORMATION: CONSENSUS SEQUENCE
<220> FEATURE:
<221> NAME/KEY: misc_feature
<222> LOCATION: 1 ..4, 11, 32, 38, 40 .. 43, 62, 63, 70, 91, 141, 145,
      166, 168, 172, 195, 199, 221, 262, 270, 277, 284 .. 289, 309 ..
      311, 320...322, 324...330, 333, 385, 397, 411
<223> OTHER INFORMATION: Xaa = ANY  AMINO ACID, OR NO AMINO ACID

<400> SEQUENCE: 11

Xaa Xaa Xaa Xaa Met Gln Pro Ser Lys Tyr Xaa Gly Leu Val Ala Asp
1               5                   10                  15

Leu Met Pro Asn Ile Arg Leu Met Gln Tyr Ser Gly His Phe Met Xaa
20                  25                  30

Asn Tyr Thr Gly Gly Xaa Ala Xaa Xaa Xaa Xaa Leu Leu Arg Lys Ile
35                  40                  45

Tyr Ser Ser Val His Leu Val Leu Val Leu Ile Gln Phe Xaa Xaa Ile
50                  55                  60

Leu Val Asn Leu Ala Xaa Asn Ala Asp Glu Val Asn Glu Leu Ser Ala
65                  70                  75                  80

Asn Thr Ile Thr Val Leu Phe Phe Thr His Xaa Ile Thr Lys Phe Ile
85                  90                  95

Tyr Phe Ala Val Asn Ser Lys Asn Phe Tyr Arg Thr Leu Ala Ile Trp
100                 105                 110

Asn Gln Ser Asn Ser His Pro Leu Phe Ala Glu Ser Asp Ala Arg Tyr
```

```
            115                 120                 125
His Ser Ile Ala Leu Ala Lys Met Arg Lys Leu Leu Xaa Leu Val Met
130                 135                 140

Xaa Thr Thr Val Leu Ser Val Val Ala Trp Thr Thr Ile Thr Phe Phe
145                 150                 155                 160

Gly Glu Ser Val Lys Xaa Val Xaa Asp Lys Asp Xaa Thr Asn Glu Thr
165                 170                 175

Ile Thr Val Glu Ile Pro Arg Leu Pro Ile Lys Ser Trp Tyr Pro Trp
180                 185                 190

Asn Ala Xaa Ser Gly Met Xaa Tyr Ile Ile Ser Phe Ala Phe Gln Ile
195                 200                 205

Tyr Trp Leu Leu Phe Ser Met Val His Ser Asn Leu Xaa Asp Val Met
210                 215                 220

Phe Cys Ser Trp Leu Ile Phe Ala Cys Glu Gln Leu Gln His Leu Lys
225                 230                 235                 240

Gly Ile Met Lys Pro Leu Met Glu Leu Ser Ala Ser Leu Asp Thr Tyr
245                 250                 255

Arg Pro Asn Ser Ala Xaa Leu Phe Arg Ala Leu Ser Ala Xaa Ser Lys
260                 265                 270

Ser Glu Leu Ile Xaa Asn Glu Lys Asp Pro Xaa Xaa Xaa Xaa Xaa
275                 280                 285

Xaa Asp Met Asp Ile Ser Gly Ile Tyr Ser Ser Lys Ala Asp Trp Gly
290                 295                 300

Ala Gln Phe Arg Xaa Xaa Xaa Ala Pro Ser Thr Leu Gln Thr Phe Xaa
305                 310                 315                 320

Xaa Xaa Gly Xaa Xaa Xaa Xaa Xaa Xaa Asn Gly Xaa Asn Pro Asn
325                 330                 335

Gly Leu Thr Lys Lys Gln Glu Met Met Val Arg Ser Ala Ile Lys Tyr
340                 345                 350

Trp Val Glu Arg His Lys His Val Val Arg Leu Val Ala Ala Ile Gly
355                 360                 365

Asp Thr Tyr Gly Ala Ala Leu Leu Leu His Met Leu Thr Ser Thr Ile
370                 375                 380

Xaa Leu Thr Leu Leu Ala Tyr Gln Ala Thr Lys Ile Xaa Gly Val Asn
385                 390                 395                 400

Val Tyr Ala Phe Thr Val Ile Gly Tyr Leu Xaa Tyr Ala Leu Ala Gln
405                 410                 415

Val Phe His Phe Cys Ile Phe Gly Asn Arg Leu Ile Glu Glu Ser
420                 425                 430

Ser Val Met Glu Ala Ala Tyr Ser Cys His Trp Tyr Asp Gly Ser Glu
435                 440                 445

Glu Ala Lys Thr Phe Val Gln Ile Val Cys Gln Gln Cys Gln Lys Ala
450                 455                 460

Met Ser Ile Ser Gly Ala Lys Phe Phe Thr Val Ser Leu Asp Leu Phe
465                 470                 475                 480

Ala Ser Val Leu Gly Ala Val Val Thr Tyr Phe Met Val Leu Val Gln
485                 490                 495

Leu Lys

<210> SEQ ID NO 12
<211> LENGTH: 16
<212> TYPE: PRT
<213> ORGANISM: Unknown
<220> FEATURE:
```

```
<223> OTHER INFORMATION: CONSENSUS SEQUENCE

<400> SEQUENCE: 12

Arg Ser Ala Ile Lys Tyr Trp Val Glu Arg His Lys His Val Val Arg
1               5                   10                  15

<210> SEQ ID NO 13
<211> LENGTH: 11
<212> TYPE: PRT
<213> ORGANISM: Unknown
<220> FEATURE:
<223> OTHER INFORMATION: CONSENSUS SEQUENCE

<400> SEQUENCE: 13

Leu Thr Leu Leu Ala Tyr Gln Ala Thr Lys Ile
1               5                   10

<210> SEQ ID NO 14
<211> LENGTH: 43
<212> TYPE: PRT
<213> ORGANISM: Unknown
<220> FEATURE:
<223> OTHER INFORMATION: CONSENSUS SEQUENCE
<220> FEATURE:
<221> NAME/KEY: SITE
<222> LOCATION: (7)..(7)
<223> OTHER INFORMATION: Xaa = arg or ser
<220> FEATURE:
<221> NAME/KEY: SITE
<222> LOCATION: (23)..(23)
<223> OTHER INFORMATION: Xaa = his or gln

<400> SEQUENCE: 14

Phe Cys Ile Phe Gly Asn Xaa Leu Ile Glu Glu Ser Ser Ser Val Met
1               5                   10                  15

Glu Ala Ala Tyr Ser Cys Xaa Trp Tyr Asp Gly Ser Glu Glu Ala Lys
                20                  25                  30

Thr Phe Val Gln Ile Val Cys Gln Gln Cys Gln
            35                  40

<210> SEQ ID NO 15
<211> LENGTH: 43
<212> TYPE: PRT
<213> ORGANISM: Ceratitis capitata

<400> SEQUENCE: 15

Phe Cys Ile Phe Gly Asn Arg Leu Ile Glu Glu Ser Ser Ser Val Met
1               5                   10                  15

Glu Ala Ala Tyr Ser Cys His Trp Tyr Asp Gly Ser Glu Glu Ala Lys
                20                  25                  30

Thr Phe Val Gln Ile Val Cys Gln Gln Cys Gln
            35                  40

<210> SEQ ID NO 16
<211> LENGTH: 43
<212> TYPE: PRT
<213> ORGANISM: Helicoverpa zea

<400> SEQUENCE: 16

Phe Cys Ile Phe Gly Asn Arg Leu Ile Glu Glu Ser Ser Ser Val Met
1               5                   10                  15

Glu Ala Ala Tyr Ser Cys Gln Trp Tyr Asp Gly Ser Glu Glu Ala Lys
                20                  25                  30

Thr Phe Val Gln Ile Val Cys Gln Gln Cys Gln
```

<210> SEQ ID NO 17
<211> LENGTH: 43
<212> TYPE: PRT
<213> ORGANISM: Schistocerca americana

<400> SEQUENCE: 17

Phe Cys Ile Phe Gly Asn Ser Leu Ile Glu Glu Ser Ser Ser Val Met
1               5                   10                  15

Glu Ala Ala Tyr Ser Cys His Trp Tyr Asp Gly Ser Glu Glu Ala Lys
            20                  25                  30

Thr Phe Val Gln Ile Val Cys Gln Gln Cys Gln
        35                  40

<210> SEQ ID NO 18
<211> LENGTH: 33
<212> TYPE: PRT
<213> ORGANISM: Schistocerca americana

<400> SEQUENCE: 18

Ser Ile Ser Gly Ala Lys Phe Phe Thr Val Ser Leu Asp Leu Phe Ala
1               5                   10                  15

Ser Val Leu Gly Ala Val Val Thr Tyr Phe Met Val Leu Val Gln Leu
            20                  25                  30

Lys

<210> SEQ ID NO 19
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n = inosine
<220> FEATURE:
<221> NAME/KEY: misc_feature
<222> LOCATION: (18)..(18)
<223> OTHER INFORMATION: n = inosine

<400> SEQUENCE: 19
aartaytggg tngarmgnca                                           20

<210> SEQ ID NO 20
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (2)..(2)
<223> OTHER INFORMATION: n = pseudouridine
<220> FEATURE:
<221> NAME/KEY: misc_feature
<222> LOCATION: (3)..(3)
<223> OTHER INFORMATION: n = inosine

<400> SEQUENCE: 20
annckrttcc raadatrca                                            19

NUCLEIC ACIDS AND PROTEINS OF INSECT OR83B ODORANT RECEPTOR GENES AND USES THEREOF

CROSS-REFERENCE TO RELATED APPLICATIONS

This application is a divisional of application Ser. No. 10/486,781, filed Aug. 6, 2004 now U.S. Pat. No. 7,238,798, which claims priority to U.S. provisional application No. 60/312,319 filed Aug. 14, 2001, which are incorporated by reference herein in their entireties.

1. INTRODUCTION

The present invention relates to insect Or83b odorant receptor genes and methods for identifying Or83b odorant receptor genes. The invention provides nucleotide sequences of insect Or83b odorant receptor genes, amino acid sequences of their encoded proteins (including peptide or polypeptide), and derivatives (e.g., fragments) and analogs thereof. The invention further relates to fragments (and derivatives and analogs thereof) of Or83b odorant receptor proteins which comprise one or more highly conserved motifs of an Or83b odorant receptor protein. In a specific embodiment, the Or83b odorant receptor gene is not the *Drosophila melanogaster* Or83b gene. The nucleic acids of the invention may be operatively linked to promoter sequences and transformed into host cells. Methods of production of an Or83b odorant receptor protein (e.g., by recombinant means), and derivatives and analogs thereof, are provided. Antibodies to an Or83b odorant receptor protein, and derivatives and analogs thereof, are provided. Methods for identifying molecules that bind or modulate the activity of these Or83b odorant receptor genes are provided. Molecules found to bind or modulate the activity of Or83b genes may be formulated into pest control agents by providing a carrier. In a preferred embodiment, molecules that bind or modulate the activity of an Or83b gene from one species but not others is desired. Methods of modifying insect behavior by modifying an insect Or83b receptor are also provided.

2. BACKGROUND OF THE INVENTION

Insects have a profound impact upon agriculture and human health throughout the world. Damage and destruction due to insect activity represents, on average, a loss of 10-20% of agricultural crops, stored agricultural products, timber and livestock worldwide. In addition, quarantines imposed to control the spread of insect pests severely impinge on world trade and the import and export of agricultural products. Many of the most significant and devastating infectious diseases are transmitted to man by blood-feeding insects such as mosquitoes, flies and ticks. Fatalities associated with insect-borne disease far exceed one million annually, with associated illnesses surpassing 300 million (see, e.g., WHO Weekly Epidemiological Record, 1999, 74:265-270).

Presently, the spread and activity of agricultural product pests is chiefly controlled by the widespread application of potent, broad-spectrum chemical pesticides over agricultural fields, greenhouses, and storage facilities. Pests posing a danger to human health are targeted with the widespread spraying of insecticides in or near residential areas.

The use of conventional pesticides, however, is associated with significant hazards to the environment, human health, and non-renewable natural resources. As a result, governments throughout the world are placing increasingly severe restrictions and bans on the use of chemical pesticides. Moreover, insects develop resistance to pesticides after prolonged use, necessitating the spraying of increased levels of pesticide, or the development of new, more potent, pesticide formulations.

Thus while chemical insecticides are designed to kill insects, their non-selective effects on human health, the environment and other animal species make them damaging and controversial. As a result, there is a critical need to develop safe and effective tools to manage populations of insects that are a threat to food, resources and human health. One potential approach is to exploit knowledge of insect behavior and recent exciting advances in the molecular neurobiology of insect olfaction to develop novel strategies for insect control.

2.1. Insect Olfactory Behavior

The behavior of all animals, including humans, involves the perception of events in the environment by visual, auditory and other sensory systems and the translation of these sensory stimuli into appropriate muscle responses. In simpler organisms such as insects, the recognition of sensory stimuli results in very stereotyped or "hard-wired" behaviors. Thus, by modifying or blocking the perception of environmental cues, it is possible to alter the behavior of such animals in a predictable way. Such alterations afford a powerful means to interfere with or divert innate behaviors that have a destructive effect on human health and welfare, such as the host-finding behavior of biting insects and agricultural pests.

Many insect behaviors, such as the location and selection of mating partners, food sources and suitable places for egg laying, are driven by the recognition of specific odors in the environment. For example, the male hawkworm moth, *Manduca sexta*, can detect extremely low concentrations of an attractive odor, called a pheromone, produced by females of the same species, and uses this sense to pursue females over large distances (Hildebrand, 1995, Proc. Nat'l Acad. Sci. U.S.A. 92:67-74). Female navel orangeworm moths, *Amyelois transitella*, a pest of almonds in California, are attracted to and lay eggs on their preferred host plant in response to volatile odors emitted by almond fruits and by larvae feeding on the almonds (Curtis and Clark, 1979, Environ. Entomol. 8:330-333; Phelan et al., 1991, J. Chem. Ecol. 17:599-614). Social insects, such as ants, make extensive use of chemical cues in communication, for example in the recognition and attack of intruder ants from other colonies (Hölldobler and Wilson, 1990, *The Ants*, Belknap Press of Harvard University Press, Cambridge, Mass.). Finally, female mosquitoes of many species, including *Anopheles gambiae*, the principal malaria carrier, orient toward and locate human hosts by detecting human-specific scents (Takken and Knols, 1999, Annu. Rev. Entomol. 44:131-157; Bock and Cardew, eds., 1996, *Olfaction in Mosquito-Host Interactions* (Ciba Foundation Symposium 200), Wiley, Chichester). Recent progress in the understanding of the molecular basis of the sense of smell provides important new insight into the mechanisms by which these odor cues elicit specific behaviors. These advances provide an exciting opportunity to develop new tools for the behavior-based control of destructive insect species.

2.2. The Molecular Biology of Insect Olfaction

Insects recognize odors in the environment using specialized olfactory organs, namely the antenna and the maxillary palps. The antenna is a highly evolved structure that extends from the head and can attain a size equivalent to the length of the organism. The maxillary palps are a pair of club-shaped structures adjacent to the proboscis. The antenna and maxillary palps are covered with tiny sensory hairs that contain nerve cells with specialized machinery that can detect odorants often at vanishingly low concentrations. The initial step in the detection of odors requires the binding of odorants to specific receptor molecules that reside on the surface of these nerve cells.

Recently, a family of roughly 60 genes encoding odorant receptors has been identified in the genome of the model insect, the fruit fly *Drosophila melanogaster* (Vosshall et al., 1999, Cell, 96:725-736; Clyne et al., 1999, Neuron 22:327-338; Gao and Chess, 1999, Genomics 60:31-39; Vosshall et al., 2000, Cell, 102:147-159). These odorant receptors have seven predicted transmembrane domains and belong to the large superfamily of proteins termed G-protein coupled receptors (GPCRs). The expression of 42 of these receptor genes has been detected in small, non-overlapping subsets of olfactory neurons in the antenna or maxillary palp (Vosshall et al., 2000, Cell 102:147-159). The large size of this gene family, their predicted identity as seven transmembrane domain-containing GPCRs, and their selective expression in olfactory neurons strongly implicate them in the process of olfactory recognition in the fly. More recently, functional studies (Wetzel et al., 2001, Proc. Natl. Acad. Sci. USA 98:9377-9380; Störtkuhl and Kettler, 2001, Proc. Natl. Acad. Sci. USA 98:9381-9385) have identified a candidate ligand for one of these *Drosophila* odorant receptor gene products, confirming their identity as receptors for behaviorally relevant odorants.

One striking exception to the rule that an individual olfactory neuron expresses a single odorant receptor gene is the odorant receptor Or83b (previously known as A45; Vosshall et al., 1999, Cell, 96:725-736), which is expressed by most, if not all, olfactory neurons in the antenna and maxillary palp. Thus, it appears that olfactory neurons actually express two odorant receptor genes: the "ubiquitous" odorant receptor gene Or83b, and one of the other "classical" odorant receptor genes.

Further molecular genetic studies in *Drosophila* have provided additional insight into the logic of olfactory processing in insects. How does the insect brain know what the antenna is smelling? Expression studies have revealed that individual olfactory neurons are functionally distinct in that each nerve cell expresses only one of the odorant receptor genes (Vosshall et al., 1999, Cell, 96:725-736). Olfactory neurons expressing the same receptor and therefore responsive to the same odor extend axons that converge on a fixed point in the brain (Vosshall et al., 2000, Cell, 102:147-159). Different neurons converge on different points. It immediately follows that a given odor will activate a small group of neurons in the antenna that in turn will activate distinct spatial patterns in the insect brain. The quality of a perceived odor is therefore determined by spatial patterns of activation in the brain. These patterns are then interpreted to elicit appropriate behavioral responses such as attraction, repulsion, flight, mating and feeding. Odorants that modulate such behaviors in harmful or destructive insect species will be of great value in managing populations of these harmful and destructive insects.

Citation of a reference herein shall not be construed as an admission that such reference is prior art to the present invention.

3. SUMMARY OF THE INVENTION

The present inventor has identified homologs of the "ubiquitous" *Drosophila* odorant receptor gene Or83b in several dipteran, lepidopteran and orthopteran species, including species that have a significant impact on agricultural production and human health. Or83b is highly conserved among insect species, suggesting an essential role for this gene in insect olfactory function. Widespread expression of Or83b was detected in olfactory neurons in the agricultural pest *Helicoverpa zea*, in the malaria mosquito *Anopheles gambiae*, in the locust *Schistocerca americana*, and in the medfly *Ceratitis capitata*. These data therefore lend support to the notion that compounds targeting Or83b activity will have utility in the control of numerous insect species injurious to human health and welfare. Natural or synthetic compounds that stimulate or block Or83b activity will disrupt olfactory-driven behaviors and will be useful as novel tools for the control and management of pest insect species.

The identification of Or83b homologs in pest insect species by the present inventor permits the following strategy for the development of safe and effective insect control products: First, functional odorant receptor molecules are produced in cultured cells or in *Xenopus laevis* oocytes, or overexpressed in transgenic insects. Cells expressing Or83b receptors can be used as a screening tool for the rapid, efficient discovery of novel compounds that interact with pest insect odorant receptors. This screening methodology can be used to identify compounds act as "super-agonists", that is, compounds that bind to receptors with higher affinity than the natural agonists. In addition, similar screening techniques can be used to isolate compounds that inactivate or antagonize receptor function, providing potent and selective chemicals to interfere with olfactory-driven behaviors.

The compounds identified in such screens may be used for attracting insects to traps or to localized toxins, for monitoring pests, for repelling insects from individuals or from residential areas, or for interfering with the function of the olfactory system such that insects are unable to locate food and hosts. Since different species of insects have highly specialized food and host preferences and the odorant receptors that mediate these behaviors are extremely variable between species, control strategies that target olfaction offer powerful and selective approaches to combat pest insects. In contrast to non-selective pesticides, such products have broad applicability as pest control agents. Whether used for pesticides, repellants or attractants, these agents selectively target disease vectors and can be expected to be harmless to beneficial species of insects, insect predators and other animals. Moreover, as behaviorally-based strategies present less selective pressure than chemical pesticides and genetically engineered crops, these strategies are expected to help reduce the appearance of pesticide-resistant insect vectors. Thus, the compounds identified using this methodology will offer novel approaches to control insect damage and the spread of disease, and will significantly reduce dependence on toxic pesticides, having a direct and immediate impact on coordinated insect management programs.

In one aspect, the present invention provides nucleic acids encoding insect Or83b receptors or fragments or motifs of insect Or83b receptors.

In certain embodiments, the present invention provides an isolated nucleic acid comprising a nucleotide sequence which encodes a polypeptide molecule comprising a first motif comprising the amino acid sequence of SEQ ID NO:12, or a fragment thereof of at least 10, 15 or 20 amino acids, wherein said polypeptide molecule is an insect Or83b polypeptide or a fragment thereof. In one embodiment, the sequence of said polypeptide molecule is not found in SEQ ID NO:10. In another embodiment, the sequence of said polypeptide molecule is not SEQ ID NO:10.

The present invention further provides an isolated nucleic acid comprising a nucleotide sequence which encodes a polypeptide molecule comprising a first insect Or 83b motif comprising the amino acid sequence of SEQ ID NO:12, or a fragment thereof of at least 10, 15 or 20 amino acids, wherein said polypeptide molecule is an insect Or83b polypeptide or a fragment thereof, said polypeptide molecule further comprising a second motif comprising the amino acid sequence of SEQ ID NO:13, or fragment of SEQ ID NO:13 of 10 amino acids.

The present invention further provides an isolated nucleic acid comprising a nucleotide sequence which encodes a polypeptide molecule comprising a first insect Or 83b motif comprising the amino acid sequence of SEQ ID NO:12, or a fragment thereof of at least 10, 15 or 20 amino acids, wherein said polypeptide molecule is an insect Or83b polypeptide or a fragment thereof, said polypeptide molecule further comprising a second motif comprising the amino acid sequence of SEQ ID NO:14, or a fragment of SEQ ID NO:14 of at least 10 amino acids. In certain specific embodiments, the fragment of SEQ ID NO:14 is at least 15 or 20 amino acids. In other specific embodiments, the motif of SEQ ID NO:14 comprises SEQ ID NO:15, 16 or 17.

The present invention further provides an isolated nucleic acid comprising a nucleotide sequence which encodes a polypeptide molecule comprising a first insect Or 83b motif comprising the amino acid sequence of SEQ ID NO:12, or a fragment thereof of at least 10, 15 or 20 amino acids, wherein said polypeptide molecule is an insect Or83b polypeptide or a fragment thereof, said polypeptide molecule further comprising a second motif comprising the amino acid sequence of SEQ ID NO:18, or fragment of SEQ ID NO:18 of at least 10 amino acids. In certain specific embodiments, the fragment of SEQ ID NO:18 is at least 15 or 20 amino acids.

The present invention yet further provides an isolated nucleic acid comprising a nucleotide sequence which encodes a polypeptide molecule comprising a first motif comprising the amino acid sequence of SEQ ID NO:13, or a fragment thereof of 10 amino acids, wherein said polypeptide molecule is an insect Or83b polypeptide or a fragment thereof. In one embodiment, the sequence of said polypeptide molecule is not found in SEQ ID NO:10. In another embodiment, the sequence of said polypeptide molecule is not SEQ ID NO:10.

The present invention further provides an isolated nucleic acid comprising a nucleotide sequence which encodes a polypeptide molecule comprising a first insect Or 83b motif comprising the amino acid sequence of SEQ ID NO:13, or a fragment thereof of 10 amino acids, wherein said polypeptide molecule is an insect Or83b polypeptide or a fragment thereof, said polypeptide molecule further comprising a second motif comprising the amino acid sequence of SEQ ID NO:14, or fragment of SEQ ID NO:14 of at least 10 amino acids. In certain specific embodiments, the fragment of SEQ ID NO:14 is at least 15 or 20 amino acids. In other specific embodiments, the motif of SEQ ID NO:14 comprises SEQ ID NO: 15, 16 or 17.

The present invention further provides an isolated nucleic acid comprising a nucleotide sequence which encodes a polypeptide molecule comprising a first insect Or 83b motif comprising the amino acid sequence of SEQ ID NO:13, or a fragment thereof of 10 amino acids, wherein said polypeptide molecule is an insect Or83b polypeptide or a fragment thereof, said polypeptide molecule further comprising a second motif comprising the amino acid sequence of SEQ ID NO:18 or fragment of SEQ ID NO:18 of at least 10 amino acids. In certain specific embodiments, the fragment of SEQ ID NO:18 is at least 15 or 20 amino acids.

Thus, the present invention provides an isolated nucleic acid comprising a nucleotide sequence which encodes a polypeptide molecule comprising a first insect Or 83b motif comprising the amino acid sequence of SEQ ID NO:14, or a fragment thereof of at least 10, 15 or 20 amino acids, wherein said polypeptide molecule is an insect Or83b polypeptide or a fragment thereof. In one embodiment, the sequence of said polypeptide molecule is not found in SEQ ID NO:10. In another embodiment, the sequence of said polypeptide molecule is not SEQ ID NO:10. In certain specific embodiments, the motif of SEQ ID NO:14 comprises SEQ ID NOs:15, 16, or 17.

The present invention further provides an isolated nucleic acid comprising a nucleotide sequence which encodes a polypeptide molecule comprising a first insect Or 83b motif comprising the amino acid sequence of SEQ ID NO:14, or a fragment thereof of at least 10, 15 or 20 amino acids, wherein said polypeptide molecule is an insect Or83b polypeptide or a fragment thereof, said polypeptide molecule further comprising a second motif comprising the amino acid sequence of SEQ ID NO:18, or a fragment of SEQ ID NO:18 of at least 10 amino acids. In certain specific embodiments, the fragment of SEQ ID NO:18 is at least 15 or 20 amino acids.

The present invention yet further provides isolated nucleic acid comprising a nucleotide sequence which encodes a polypeptide molecule comprising the amino acid sequence of three or more of SEQ ID NOs:12, 13, 14, or 18, or a fragment of at least 10 amino acids of SEQ ID NOs:12, 13, 14, or 18, wherein said polypeptide molecule is an insect Or83b polypeptide or a fragment thereof. Alternatively, the present invention provides an isolated nucleic acid comprising a nucleotide sequence which encodes a polypeptide molecule comprising the amino acid sequence of SEQ ID NOs:12, 13, 14, and 18, or a fragment of at least 10 amino acids of SEQ ID NOs:12, 13, 14, and 18, wherein said polypeptide molecule is an insect Or83b polypeptide or a fragment thereof. In one embodiment, the sequence of said polypeptide molecule is not found in SEQ ID NO:10. In another embodiment, the sequence of said polypeptide molecule is not SEQ ID NO:10. In certain specific embodiments, SEQ ID NO:14 comprises SEQ ID NOs:15, 16, or 17.

In another aspect of the present invention, methods of identifying a nucleic acid encoding an insect Or83b polypeptide are provided. In one embodiment, a method of identifying a nucleic acid encoded an insect Or83 polypeptide comprises PCR amplification of insect genomic DNA or cDNA with a forward primer comprising a degenerate oligonucleotide encoding at least six amino acids of SEQ ID NOs:12, 13 or 14, or its complement, and a reverse primer comprising a degenerate oligonucleotide encoding at least six amino acids of SEQ ID NOs:13, 14 or 18, or its complement; then detection of a PCR amplification product, thereby identifying a nucleic acid encoding an insect Or83b polypeptide. The reverse primer corresponds to a nucleic acid sequence downstream of the forward primer. In a preferred mode of the embodiment, PCR amplification results in a product of at least 150 nucleotides.

In yet other aspects of the present invention, insect Or83b polypeptides and insect Or83b polypeptide fragments are provided.

In certain embodiments, the invention provides a purified polypeptide comprising an amino acid sequence having at least 80%, 90%, or 95% identity to at least 20 contiguous amino acids of the sequence set forth in SEQ ID NO:11. In one embodiment, amino acid sequence is not found in SEQ ID NO:10. In another embodiment, the amino acid sequence does not comprise SEQ ID NO:10. In a preferred embodiment, the polypeptide is capable of being bound by an antibody that also binds to a polypeptide defined by an amino acid sequence selected from the group consisting of SEQ ID NO:2, SEQ ID NO:4, SEQ ID NO:6, and SEQ ID NO:8.

In a specific embodiment, the present invention provides a purified polypeptide comprising the amino acid sequence set forth in SEQ ID NO:11, or a fragment thereof of at least 20 contiguous amino acids. In one embodiment, amino acid sequence is not found in SEQ ID NO:10. In another embodiment, the amino acid sequence does not comprise SEQ ID NO:10.

In other specific embodiments, the present invention provides a purified polypeptide comprising an amino acid sequence having at least 80%, 90%, or 95% identity to at least 20 contiguous amino acids of the sequence set forth in SEQ ID NO:11, wherein said polypeptide comprises at least 20, 30 or 50 contiguous amino acids of the sequence as set forth in SEQ ID NO:2, or encoded by the insert of the plasmid deposited at the ATCC and assigned ATCC Accession No. PTA-3573. In a certain specific embodiment, the present invention provides a purified polypeptide comprising an amino acid sequence as set forth in SEQ ID NO:2, or encoded by the insert of the plasmid deposited at the ATCC and assigned ATCC Accession No. PTA-3573.

In other specific embodiments, the present invention provides a purified polypeptide comprising an amino acid sequence having at least 80%, 90%, or 95% identity to at least 20 contiguous amino acids of the sequence set forth in SEQ ID NO:11, wherein said polypeptide comprises at least 20, 30 or 50 contiguous amino acids of the sequence as set forth in SEQ ID NO:4, or encoded by the insert of the plasmid deposited at the ATCC and assigned ATCC Accession No. PTA-3574. In a certain specific embodiment, the present invention provides a purified polypeptide comprising an amino acid sequence as set forth in SEQ ID NO:4, or encoded by the insert of the plasmid deposited at the ATCC and assigned ATCC Accession No. PTA-3574.

In yet other specific embodiments, the present invention provides a purified polypeptide comprising an amino acid sequence having at least 80%, 90%, or 95% identity to at least 20 contiguous amino acids of the sequence set forth in SEQ ID NO:11, wherein said polypeptide comprises at least 20, 30 or 50 contiguous amino acids of the sequence as set forth in SEQ ID NO:6, or encoded by the insert of the plasmid deposited at the ATCC and assigned ATCC Accession No. PTA-3575. In a certain specific embodiment, the present invention provides a purified polypeptide comprising an amino acid sequence as set forth in SEQ ID NO:6, or encoded by the insert of the plasmid deposited at the ATCC and assigned ATCC Accession No. PTA-3575.

In yet other specific embodiments, the present invention provides a purified polypeptide comprising an amino acid sequence having at least 80%, 90%, or 95% identity to at least 20 contiguous amino acids of the sequence set forth in SEQ ID NO:11, wherein said polypeptide comprises at least 20, 30 or 50 contiguous amino acids of the sequence as set forth in SEQ ID NO:8, or encoded by the insert of the plasmid deposited at the ATCC and assigned ATCC Accession No. PTA-3576. In a certain specific embodiment, the present invention provides a purified polypeptide comprising an amino acid sequence as set forth in SEQ ID NO:8, or encoded by the insert of the plasmid deposited at the ATCC and assigned ATCC Accession No. PTA-3576.

The present invention yet further provides an isolated nucleic acid comprising a nucleotide sequence encoding any of the foregoing polypeptides. In certain embodiments, the nucleotide sequence is operatively linked to a promoter. The present invention yet further provides vectors comprising a nucleotide sequence encoding any of the foregoing polypeptides. The present invention yet further provides a host cell transformed with a nucleic acid comprising a nucleotide sequence encoding any of the foregoing polypeptides.

A table indicating to which Or83b-related sequence each SEQ ID NO corresponds is presented below:

| MOLECULE | NUCLEOTIDE OR AMINO ACID | SEQ ID NO |
|---|---|---|
| *Ceratitis capitata* Or83b | Nucleotide | 1 |
| *Ceratitis capitata* Or83b | Amino Acid | 2 |
| *Helicoverpa zea* Or83b | Nucleotide | 3 |
| *Helicoverpa zea* Or83b | Amino Acid | 4 |
| *Anopheles gambiae* Or83b | Nucleotide | 5 |
| *Anopheles gambiae* Or83b | Amino Acid | 6 |
| *Schistocerca americana* Or83b | Nucleotide | 7 |
| *Schistocerca americana* Or83b | Amino Acid | 8 |
| *Drosophila melanogaster* Or83b | Nucleotide | 9 |
| *Drosophila melanogaster* Or83b | Amino Acid | 10 |
| Consensus Or83b | Amino Acid | 11 |
| Or83b Motif I (AAs 347-362 of SEQ ID NO: 11) | Amino Acid | 12 |
| Or83b Motif II (AAs 386-396 of SEQ ID NO: 11) | Amino Acid | 13 |
| Or83b Motif III (AAs 420-462 of SEQ ID NO: 11, with partial degeneracy where the corresponding residue is not identical in SEQ ID NO. 2, 4, 6 and 8) | Amino Acid | 14 |
| Motif III (from *Ceratitis* and *Anopheles*) | Amino Acid | 15 |
| Motif III (from *Helicoverpa*) | Amino Acid | 16 |
| Motif III (from Locust) | Amino Acid | 17 |
| Or83b Motif IV (AAs 466-498 of SEQ ID NO: 11) | Amino Acid | 18 |
| Or83b Forward Primer I | Nucleotide | 19 |
| Or83b Reverse Primer II | Nucleotide | 20 |

In yet other aspects of the present invention, screening methods for identifying molecules, e.g., odorants, that bind to and/or modulate (i.e., agonize or antagonize) the activity of insect Or83b receptors are provided. Generally, an Or83b receptor comprises an amino acid sequence having at least 80% identity to at least 20 contiguous amino acids of the sequence set forth in SEQ ID NO:11. Most preferably, the insect Or83b receptor employed in the screening methods is not or does not comprise the *Drosophila melanogaster* Or83b receptor, as encoded by SEQ ID NO:10. In other preferred embodiments, the insect Or83b receptor employed in the screening methods comprises an amino acid sequence that is not present in the *Drosophila melanogaster* Or83b receptor, as encoded by SEQ ID NO:10.

In one embodiment, the invention provides a method of identifying a molecule that binds to an Or83b receptor, said method comprising: (a) contacting a first cell and a second cell with a test molecule under conditions conducive to binding between the Or83b receptor and the test molecule, wherein the first cell expresses the Or83b receptor, preferably on the cell surface, and the second cell does not express the Or83b receptor, and wherein the first cell and the second cell are of the same cell type; and (b) determining whether the test molecule binds to the first cell or the second cell; wherein a molecule that binds to the first cell but not the second cell is a molecule that binds to the Or83b receptor.

The present invention further provides a method for identifying a modulator of an Or83b receptor, said method comprising: (a) contacting a first cell and a second cell with a test molecule under conditions conducive to binding between the Or83b receptor and the test molecule, wherein the first cell expresses the Or83b receptor, preferably on the cell surface, and the second cell does not express the Or83b receptor, and wherein the first cell and the second cell are of the same cell type; and (b) determining whether the test molecule modulates G-protein activity in said first cell or second cell, wherein a molecule that modulates G-protein activity in the first cell but not in the second cell is an Or83b modulator. In certain preferred embodiments, G-protein activity is determined by measuring calcium ion or cyclic AMP concentration in the cell.

The present invention further provides a method for identifying a molecule that binds to an Or83b receptor from a first species but not from a second species, said method comprising: (a) contacting a first cell that expresses a first Or83b receptor, preferably on the cell surface, from said first species with a test molecule under conditions conducive to binding between said first receptor and the test molecule; (b) determining whether the test molecule binds to said first cell; (c) contacting a second cell that expresses a second Or83b receptor from said second species with the test molecule under conditions conducive to binding between said second receptor and the test molecule, wherein said second cell is of the same cell type as the first cell; and (d) determining whether said test molecule binds to said second cell, wherein a test molecule that binds to the first cell but not to the second cell binds to the Or83b receptor from the first species but not from the second species.

The present invention yet further provides a method of identifying a modulator of an Or83b receptor from a first species but not from a second species, said method comprising: (a) contacting a first cell that expresses a first Or83b receptor, preferably on the cell surface, from said first species with a test molecule under conditions conducive to binding between said first receptor and the test molecule; (b) determining whether the test molecule modulates G-protein activity in said first cell; (c) contacting a second cell that expresses a second Or83b receptor from said second species with the test molecule under conditions conducive to binding between said second receptor and the test molecule, wherein said second cell is of the same cell type as the first cell; and (d) determining whether the test molecule modulates G-protein activity in said second cell, wherein a test molecule that modulates G-protein activity in the first cell but not in the second cell modulates the Or83b receptor from the first species but not from the second species.

The present invention yet further provides a method of identifying an odorant that binds to an insect olfactory receptor, said method comprising: (a) contacting a first cell and a second cell with a test molecule under conditions conducive to binding between the insect olfactory receptor and the test molecule, wherein the first cell expresses an the insect olfactory receptor and the Or83b receptor, preferably on the cell surface, and the second cell does not express either receptor, or expresses only the odorant receptor, or expresses only the Or83b receptor, wherein the first cell and the second cell are of the same cell type; and (b) determining whether the test molecule binds to the first or the second cell; wherein a molecule that binds to the first cell but not the second cell is an odorant that binds to the insect olfactory receptor, The present invention yet further provides a method of identifying an odorant that modulates the activity of an insect olfactory receptor, said method comprising: (a) contacting a first cell and a second cell with a test molecule under conditions conducive to binding between the insect olfactory receptor and the test molecule, wherein the first cell expresses an the insect olfactory receptor and the Or83b receptor, preferably on the cell surface, and the second cell does not express either receptor, or expresses only the odorant receptor, or expresses only the Or83b receptor, wherein the first cell and the second cell are of the same cell type; and (b) determining whether the test molecule modulates G-protein activity in said first cell or second cell, wherein a molecule that modulates G-protein activity in the first cell but not the second cell is an odorant that modulates the activity of the insect olfactory receptor. In certain preferred embodiments, the G-protein activity is determined by measuring calcium ion or cyclic AMP concentration in the cell.

The present invention yet further provides a method of identifying an odorant that binds to a first insect olfactory receptor but not a second insect olfactory receptor, said method comprising: (a) contacting a first cell that expresses an Or83b receptor, preferably on the cell surface, and the first insect olfactory receptor, preferably on the cell surface, with a test molecule under conditions conducive to binding between the first receptor and the test molecule; (b) determining whether the test molecule binds to said first cell; (c) contacting a second cell that expresses the Or83b receptor and the second insect olfactory receptor under conditions conducive to binding between the second receptor and the test molecule, wherein said second cell is of the same cell type as the first cell; and (d) determining whether the test molecule binds to said second cell, wherein a test molecule that binds to the first cell but not to the second cell is an odorant that binds to the first insect olfactory receptor but not to the second insect olfactory receptor.

The present invention yet further provides a method of identifying an odorant that modulates the activity of a first insect olfactory receptor but not the activity of a second insect olfactory receptor, said method comprising: (a) contacting a first cell that expresses an Or83b receptor, preferably on the cell surface, and the first insect olfactory receptor, preferably on the cell surface, with a test molecule under conditions conducive to binding between the receptors and the test molecule; (b) determining whether the test molecule binds to said first cell; (c) contacting a second cell that expresses the Or83b receptor and the second insect olfactory receptor under conditions conducive to binding between the receptors and the test molecule, wherein said second cell is of the same cell type as the first cell; and (d) determining whether said test molecule binds to said second cell, wherein a test molecule that binds to the first cell but not the second cell is an odorant that binds to the first insect olfactory receptor but not the second insect olfactory receptor.

The present invention yet further provides a method of identifying a molecule that binds to an insect Or83b receptor but not an insect gustatory receptor, said method comprising: (a) contacting a first cell that expresses the Or83b receptor, preferably on the cell surface, with a test molecule under conditions conducive to binding between the receptor and the test molecule; (b) determining whether the test molecule binds to said first cell; (c) contacting a second cell that expresses the insect gustatory receptor, preferably on the cell surface, under conditions conducive to binding between the receptor and the test molecule, wherein said second cell is of the same cell type as the first cell; and (d) determining whether the test molecule binds to said second cell, wherein a test molecule that binds to the first cell but not to the second cell is a molecule that binds to the insect Or83b receptor but not to the insect gustatory receptor.

The present invention yet further provides a method of identifying a molecule that modulates an insect Or83b receptor but not an insect gustatory receptor, said method comprising: (a) contacting a first cell that expresses the Or83b receptor, preferably on the cell surface, with a test molecule under conditions conducive to binding between the receptor and the test molecule; (b) determining whether the test molecule modulates G-protein activity in said first cell; (c) contacting a second cell that expresses the insect gustatory receptor, preferably on the cell surface, under conditions conducive to binding between the receptor and the test molecule, wherein said second cell is of the same cell type as the first cell; and (d) determining whether the test molecule modulates G-protein activity in said second cell, wherein a test molecule that modulates G-protein activity in the first cell but not in the second cell is a molecule that modulates the activity the insect Or83b receptor but not the activity of the insect gustatory receptor.

In yet other aspects of the present invention, insect control agent formulations, comprising one or more of the foregoing Or83b binding molecules or modulators and a suitable carrier are provided. In one embodiment, the insect control agent is an insect repellent. In another embodiment, the insect control agent is an insect attractant. The carrier can be a solid carrier or a liquid carrier. Examples of suitable carriers are described in Section 5.9, infra.

4. BRIEF DESCRIPTION OF THE DRAWINGS

FIGS. 1A-1C. The *Drosophila melanogaster* Or83b nucleotide sequence (SEQ ID NO: 9), and amino acid sequence (SEQ ID NO: 10) are depicted. Amino acids are depicted in single letter code.

FIGS. 2A and 2B. The nucleotide sequence *Ceratitis capitata* Or83b open reading frame (SEQ ID NO: 1) obtained by PCR amplification and its encoded protein (SEQ ID NO: 2) are shown.

FIGS. 3A-3C. The complete sequence of the *Helicoverpa zea* (Corn Earworm) Or83b cDNA (SEQ ID NO: 3) and its predicted encoded protein (SEQ ID NO: 4) are shown.

Figure 4A:
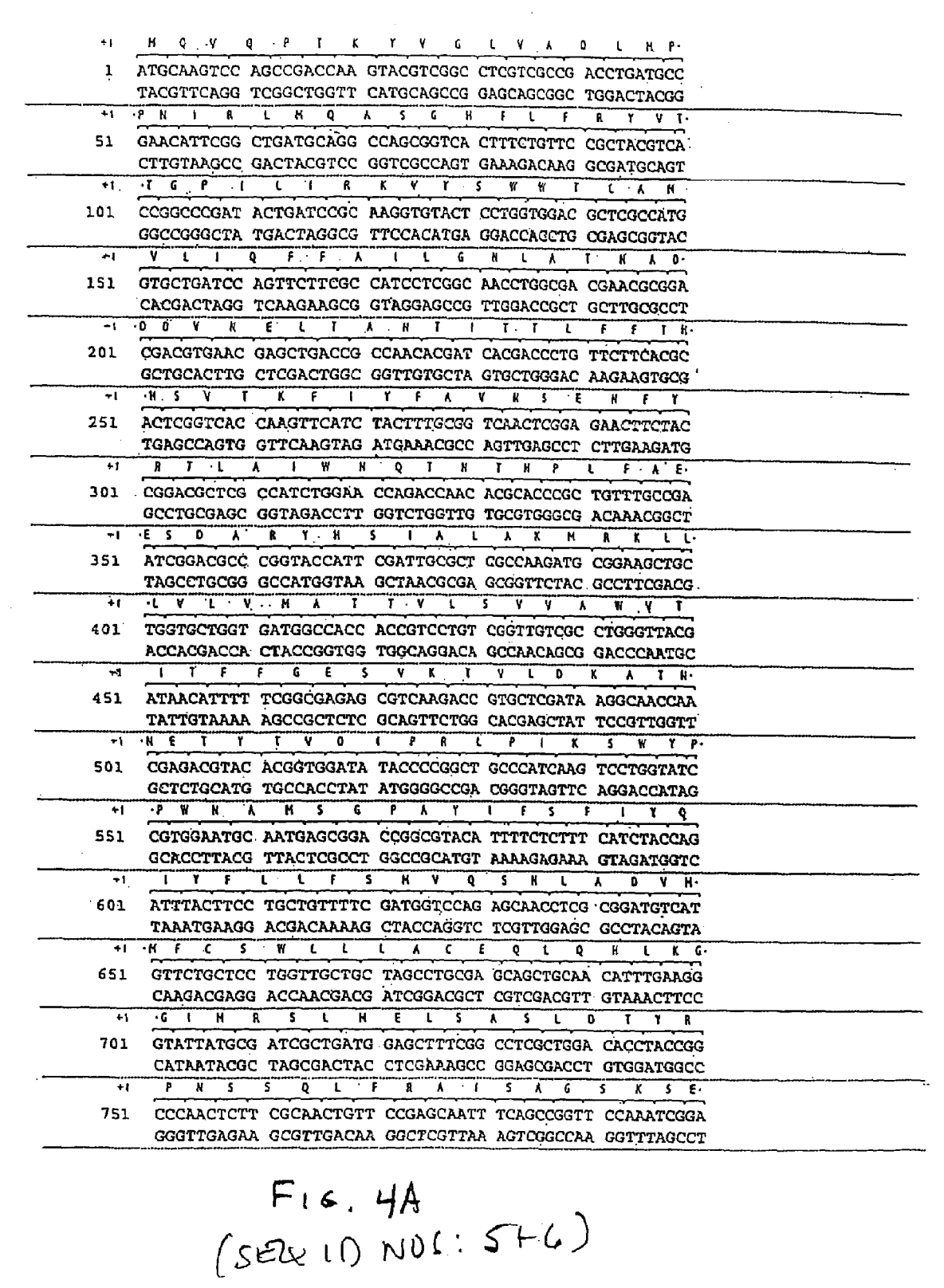

FIGS. 4A and 4B. The nucleotide sequence of the *Anopheles gambiae* Or83b open reading from (SEQ ID NO: 5) obtained by PCR amplification of *Anopheles* cDNA and its predicted encoded protein (SEQ ID NO: 6) are shown.

FIGS. 5A and 5B. The coding region of the *Schistocera Americana* Or83b cDNA (SEQ ID NO: 7) and its predicted encoded protein (SEQ ID NO: 8) are shown.

FIGS. 6A and 6B. Sequence alignment of the Or83b proteins. Protein sequences predicted by GENSCAN or from cDNA sequences were aligned using ClustalW (Vector NTI Suite, AlignX program, Informax, Inc.) Identical amino acids are shown in black; similar amino acids are shaded in gray. A consensus Or83b amino acid sequence (SEQ ID NO: 11) derived from the ClustalW alignment is also depicted.

FIGS. 7A-E. Expression of the Or83b genes in olfactory tissues.

FIG. 7A) Schematic diagram showing a cross-section through a representative insect olfactory sensory hair. The sensory hair is a hollow, fluid-filled structure with pores that allow the diffusion of odorants (red spheres) into the central cavity. Clusters of olfactory neurons (blue) situated beneath each sensory hair extend dendrites into the lumen of the sensory hair. Interactions between odorants and odorant receptors localized on these dendrites result in the production of an electrical signal that is propagated to the brain.

Figure 7B:
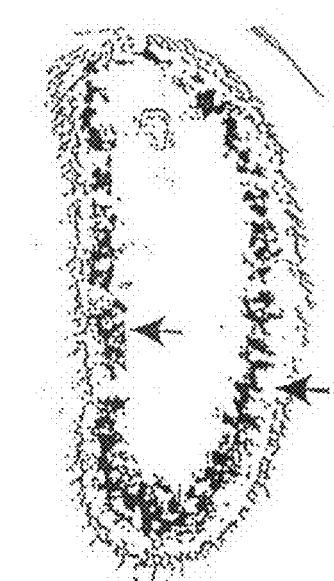

FIG. 7B) A *Ceratitis capitata* Or83b antisense probe was hybridized to longitudinal sections of adult antenna. Numerous Or83b-expressing cells are detected (arrows).

Figure 7C:
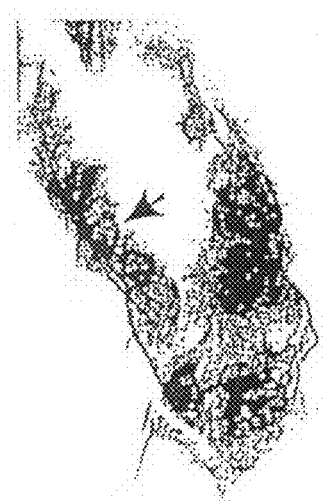

FIG. 7C) A longitudinal section of an adult female *Anopheles gambiae* antenna was hybridized with an Or83b antisense probe and visualized with alkaline phosphatase. Exemplary Or83b-expressing cells are indicated with arrows.

Figure 7D:

FIG. 7D) A *Helicoverpa zea* Or83b antisense probe was hybridized to longitudinal sections of adult female antenna. Multiple Or83b-expressing cells are detected in each antenna segment clustered beneath olfactory sensory hairs.

Figure 7E:
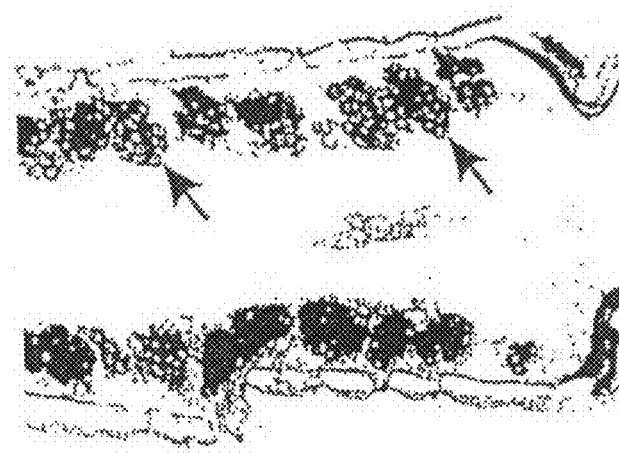
Figure 8A:
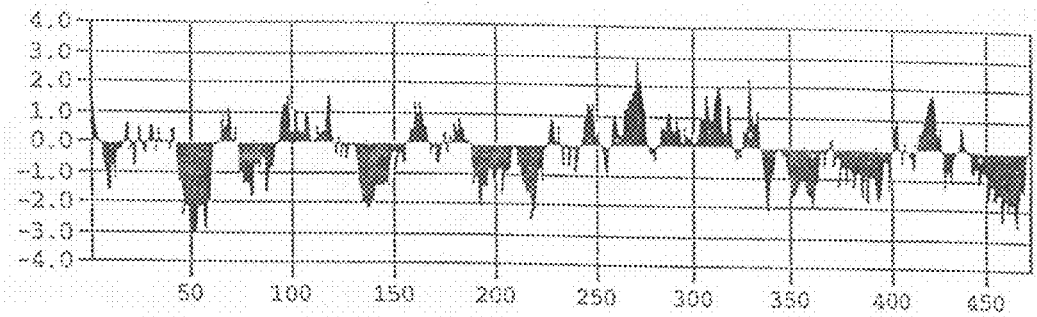
Figure 8B:
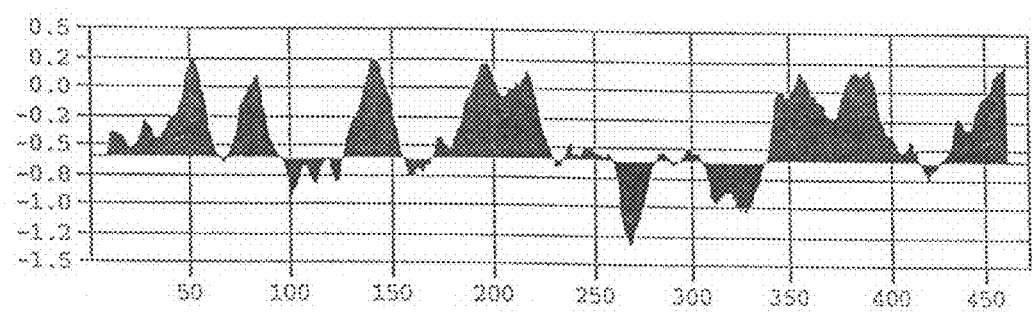
Figure 8C:
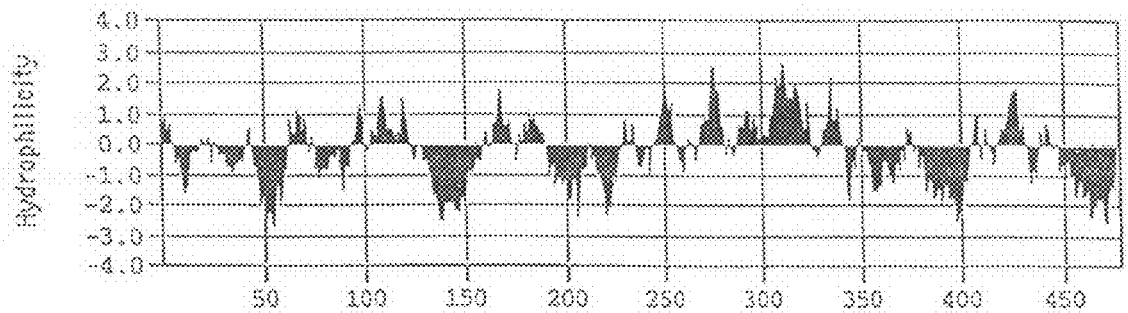
Figure 8D:
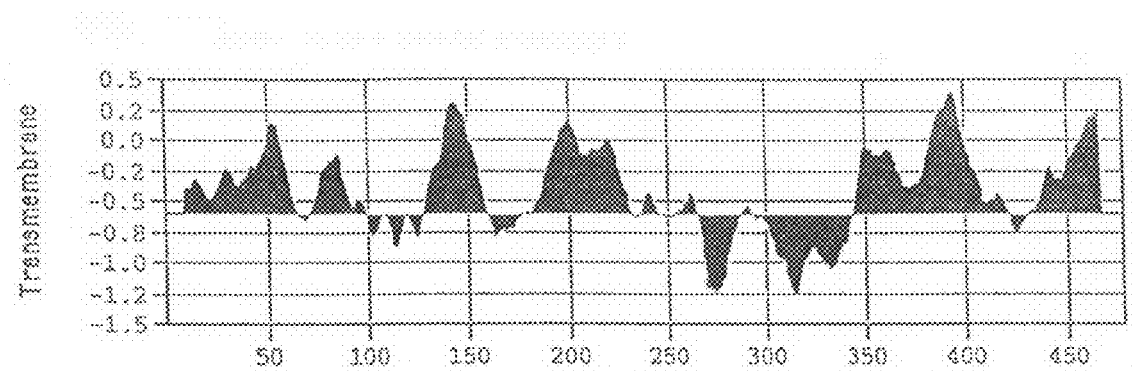
Figure 8E:
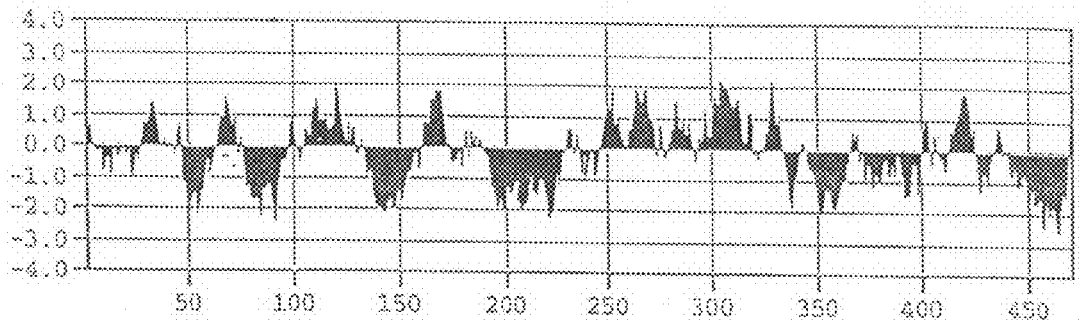
Figure 8F:
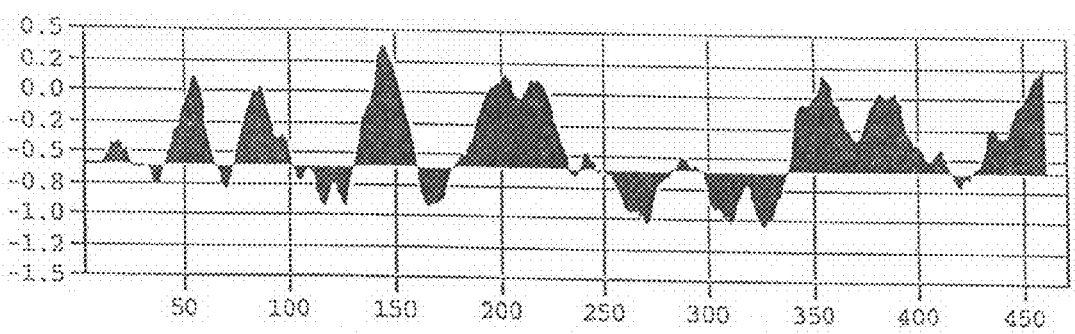
Figure 8G:
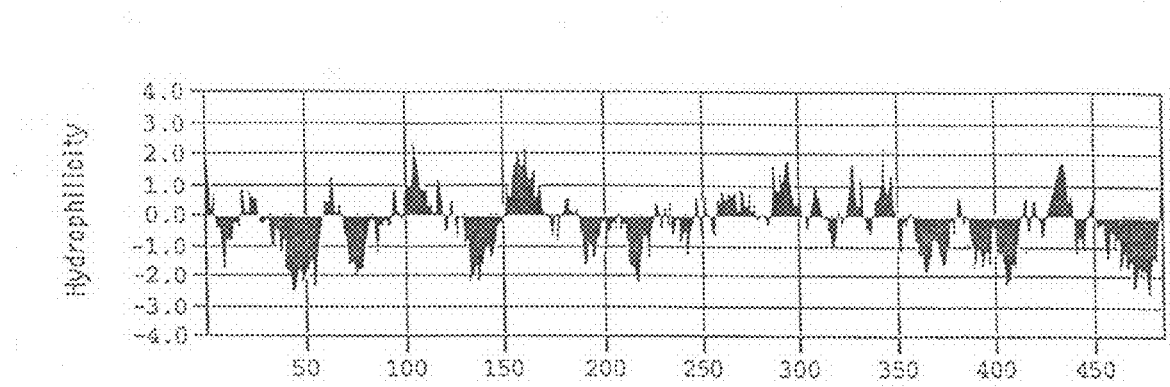
Figure 8H:
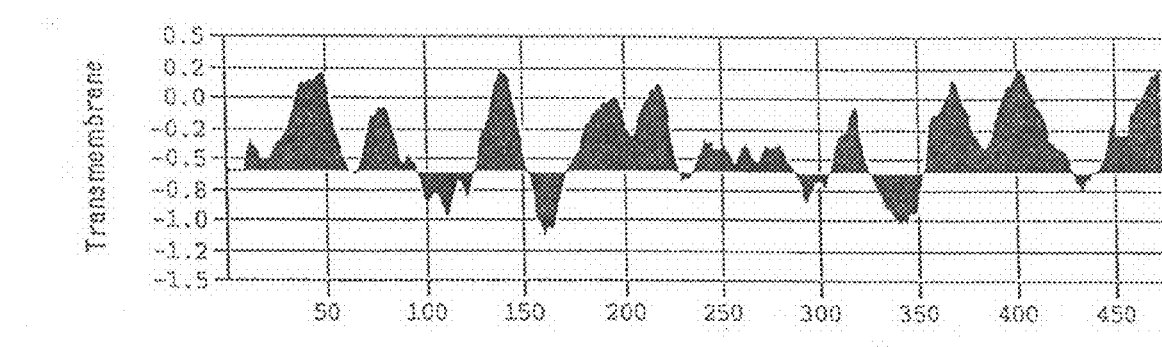

FIG. 7E) A *Schistocerca americana* Or83b antisense probe was hybridized to longitudinal sections of adult female antenna. Multiple Or83b-expressing cells are detected in each antenna segment clustered beneath olfactory sensory hairs.

FIG. 8A-8H. FIGS. 8A, 8C, 8E, and 8G are hydrophilicity plots of the *Ceratitis capitata, Anopheles gambiae, Helicoverpa zea*, and *Schistocerca americana* Or83b receptors, respectively (as described in Kyte and Doolittle, 1982, J. Mol. Biol., 157:105-132). FIGS. 8B, 8D, 8F and 8H are transmembrane domain predictions of the *Ceratitis capitata*, Anopheles gambiae, *Helicoverpa zea*, and *Schistocerca americana* Or83b receptors, respectively (as described in von Heijne, 1992, J, Mol. Biol. 225:487-494).

5. DETAILED DESCRIPTION OF THE INVENTION

Described herein is a strategy to search for novel Or83b odorant receptor genes in insect genomes. This strategy has been successful in identifying novel insect odorant receptor genes encoding Or83b odorant receptor proteins related to the Or83b receptor of *Drosophila melanogaster*. These new odorant receptor genes, which encode highly conserved proteins among various insect species, constitute very useful targets for pest control agents.

The present invention thus provides proteins encoded by and nucleotide sequences of insect Or83b odorant receptor genes. In a specific embodiment, the invention relates to the proteins encoded by and the nucleic acid sequence of an Or83b odorant receptor gene from *C. capitata, H. zea, A. gambiae*, or *S. americana*. The invention further relates to fragments and other derivatives and analogs of such Or83b odorant receptor proteins. In a preferred embodiment, these proteins, fragments and other derivatives and analogs are not the *D. melanogaster* sequence. In a preferred embodiment, these proteins, fragments and other derivatives and analogs are not found in the *D. melanogaster* sequence. In a more preferred embodiment, these proteins, fragments and other derivatives and analogs do not comprise the *D. melanogaster* sequence. In a preferred embodiment, these proteins, fragments and other derivatives and analogs do not comprise a subsequence found in the *D. melanogaster* sequence, wherein the *D. melanogaster* subsequence is 10, 20, 30, 50, 75, 100 or 200 consecutive amino acids of the *D. melanogaster* amino acid sequence. Nucleic acids encoding such fragments or derivatives are also within the scope of the invention. Production of the foregoing proteins, e.g., by recombinant methods, is provided.

The invention further provides a consensus Or83b sequence derived from the alignment of multiple Or83b species.

The invention further relates to fragments (and derivatives and analogs thereof) of an Or83b protein which comprise one or more motifs of an insect Or83b odorant receptor.

Antibodies to an Or83b protein, its derivatives and analogs, are additionally provided.

The invention is illustrated by way of examples set forth in Section 6 below which disclose, inter alia, the cloning and characterization of the insect Or83b odorant receptor genes.

The nucleic acids and polypeptides of the invention may be isolated or purified.

"Isolated" or "purified" when used herein to describe a nucleic acid molecule or nucleotide sequence, refers to a nucleic acid molecule or nucleotide sequence which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, an isolated nucleic acid does not encompass a nucleic acid present in a library, such as a cDNA, genomic, or expression library. In a particular embodiment, the isolated nucleic acid of the invention does not contain introns. In another embodiment, the isolated nucleic acid of the invention does not have the sequence set forth in Genbank Accession No. AL152626 or the sequence set forth in Genbank Accession No. AL141712. In another embodiment, the isolated nucleic acid of the invention is not the cloning vector and insert identified as clone 24M01 of NotreDame1 library from strain PEST of *Anopheles gambiae* (African malaria mosquito) in Genbank Accession No. AL152626, or clone 04E15 of NotreDame1 library from strain PEST of *Anopheles gambiae* (African malaria mosquito) in Genbank Accession No. AL141712. In another embodiment, the nucleic acid of the invention has sequences from the *Anopheles* nucleic acid sequences set forth in both Genbank Accession No. AL152626 and Genbank Accession No. AL141712.

"Isolated" or "purified" when used herein to describe a protein or biologically active portion thereof (i.e., a polypeptide or peptide fragment), refers to a protein or biologically active portion thereof substantially free of cellular material or other contaminating proteins from the cell or tissue source from which the protein is derived, or substantially free of chemical precursors or other chemicals when chemically synthesized. A protein or biologically active portion thereof (i.e., a polypeptide or peptide fragment) that is substantially free of cellular material includes preparations of protein having less than about 30%, 20%, 10%, or 5% (by dry weight) of heterologous, or contaminating, protein.

The term "olfactory receptor" or "odorant receptor" refers to a polypeptide involved in olfactory sensation. An "olfactory receptor nucleic acid" is a nucleic acid encoding a polypeptide involved in olfactory sensation. Insects have two classes of odorant receptor genes: the Or83b class of receptors expressed by most, if not all, olfactory neurons in the antenna and maxillary palp, and the "classical" odorant receptor genes which are expressed in small, non-overlapping subsets of olfactory neurons. The term "Or83b receptor" or "Or83b polypeptide" as used herein refers to a member of the Or83b class of olfactory receptors, which are characterized by the following features:

(a) has a hydrophilicity profile substantially as shown in FIG. 8A, FIG. 8C, FIG. 8E or FIG. 8G, e.g., has the same or a similar distribution of hydrophobic peaks as shown in FIG. 8A, FIG. 8C, FIG. 8E or FIG. 8G, or a transmembrane domain distribution substantially as shown in FIG. 8B, FIG. 8D, FIG. 8F, or FIG. 8H, i.e., has the same or a similar distribution of transmembrane domains as shown in FIG. 8A, FIG. 8C, FIG. 8E or FIG. 8G;

(b) is expressed in the majority of olfactory neurons in the insect antenna and maxillary palp;

(c) comprises a protein sequence that is at least 65% identical overall to the consensus Or83b sequence (SEQ ID NO:11); and (d) has least 80% sequence identity to the carboxy terminal 150 amino acids of SEQ ID NO:11 in the corresponding region of the protein.

A fragment of a Or83 polypeptide or Or83-related polypeptide is at least a 10 amino acid fragment. In preferred embodiments, the fragment is 20, 30 or 50 amino acids. In other preferred embodiments, the fragment is not found in *D. melanogaster* or is not or does not comprise the Or83b polypeptide of *D. melanogaster*.

The polypeptides of this invention have a variety of uses. They can be used, for example, as species-specific pest control agents. The polypeptides can also be used for screening for odorant molecules useful for controlling the behavior of pest control agents, as described in Section 5.8, infra.

For clarity of disclosure, and not by way of limitation, the detailed description of the invention is divided into the subsections which follow.

5.1. Insect Or83b Nucleic Acids

Insect Or83b nucleic acids, including Or83b genes, are described herein. As used herein, an Or83b gene or gene sequence refers to: (a) at least one of the nucleotide sequences and/or fragments thereof that are depicted herein in any one of FIGS. 1-5 (SEQ ID NOS:1, 3, 5, 7, and 9); (b) any nucleotide sequence or fragment thereof that encodes the amino acid sequences that are depicted in any one of FIGS. 1-6 (SEQ ID NOS:2, 4, 6, 8, 10 and 11); (c) any nucleotide sequence that hybridizes to the complement of one of the coding nucleotide sequences depicted herein in any one of FIGS. 1-5 (SEQ ID NOS:1, 3, 5, 7, and 9) under stringent conditions, e.g., hybridization to filter-bound DNA in 6× sodium chloride/sodium citrate (SSC) at about 45° C. followed by one or more washes in 0.2×SSC/0.1% SDS at about 50-65° C., or hybridization to filter-bound DNA in 0.5 M sodium pyrophosphate/7% SDS at about 65° C. followed by one or more washes in 0.2×SSC/1% SDS at about 42-55° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3); (d) any nucleotide sequence that hybridizes to the complement of one of the coding nucleotide sequences depicted herein in any one of FIGS. 1-5 (SEQ ID NOS:1, 3, 5, 7, and 9) under highly stringent conditions, e.g., hybridization to filter-bound nucleic acid in 6×SSC at about 45° C. followed by one or more washes in 0.1×SSC/0.2% SDS at about 68° C., or hybridization to filter-bound DNA in 0.5 M sodium pyrophosphate/7% SDS at about 65° C. followed by one or more washes in 0.2×SSC/1% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3), including such other hybridization conditions as those described herein; (e) any nucleic acid sequence that encodes an Or83b polypeptide, defined as a polypeptide (i) with a hydrophilicity profile substantially as shown in FIG. 8A, FIG. 8C, FIG. 8E or FIG. 8G, or a transmembrane domain distribution substantially as shown in FIG. 8B, FIG. 8D, FIG. 8F, or FIG. 8H, (ii) that is expressed in the majority of olfactory neurons in the insect antenna and maxillary palp, (iii) that comprises a protein sequence that is at least 65% identical overall to the consensus Or83b sequence (SEQ ID NO:11), and (iv) that has least 80% sequence identity to the carboxy terminal 150 amino acids of SEQ ED NO:11 in the corresponding region of the protein, or a nucleic acid encoding a fragment an Or83b protein; and (f) the complement of any of the Or83b genes or gene sequences recited in (a)-(e) above.

Preferably, the nucleic acid molecules of the invention do not have the entire sequence set forth in SEQ ID NO. 9. In other embodiments, the nucleic acid molecules of the invention do not comprise the entire sequence set forth in SEQ ID NO. 9. In another embodiment, the nucleic acid molecules of the invention do not comprise a fragment of the nucleic acid sequence set forth in SEQ ID NO. 9, provided that the fragment of SEQ ID NO. 9 is 20, 30, 40, 50, 75, 100, 150, 200, 300, 400 or 500 consecutive nucleic acids of SEQ ID NO. 9.

Preferably, the nucleic acid molecules that hybridize to the complements of the Or83b gene sequences disclosed herein are the same length or about the same length as the Or83b gene sequences disclosed herein (e.g., having an open reading frame of about 1350-1500 nucleotides in length, more preferably about 1410-1470 nucleotides in length, and most preferably about 1416-1458) and/or also encode gene products, e.g., gene products that are the same length or about the same length as an Or83b gene product encoded by a nucleotide sequence of (a) above (i.e., approximately 450-500 amino acid residues in length, more preferably about 470-490 amino acid residues in length, and most preferably about 472-486 amino acid residues in length) and/or are functionally equivalent to an Or83b gene product encoded by a nucleotide sequence of (a), above. "Functionally equivalent," as the term is used herein, can refer to, in certain embodiments, a gene product (e.g., a polypeptide) capable of exhibiting a substantially similar in vivo activity as an endogenous Or83b gene product encoded by one or more of the above-recited Or83b gene sequences. Alternatively, and in certain other embodiments, as when utilized as part of assays such as those described hereinbelow, "functionally equivalent" can refer to peptides or other molecules capable of interacting with other cellular or extracellular molecules in a manner substantially similar to the way in which the corresponding portion of the endogenous Or83b gene product would. Functionally equivalent gene products can therefore include naturally occurring Or83b gene products present in the same or different species. Functionally equivalent Or83b gene products also include gene products that retain at least one of the biological activities of an Or83b gene product described above (e.g., which is capable of being bound by an antibody that also binds to a polypeptide defined by an amino acid sequence selected from the group consisting of SEQ ID NO:2, SEQ ID NO:4, SEQ ID NO:6, and SEQ ID NO:8; which is capable of modulating G protein activity; or which is capable of binding ligand). Thus, the functionally equivalent Or83b gene products of the invention also include gene products which are recognized by and bind to antibodies (polyclonal or monoclonal) directed against one or more of Or83b gene products described above (e.g., which are encoded by the coding sequences depicted herein in FIGS. 2, 4, 6, 8, and 10).

Further, and as those skilled in the art readily appreciate, an amino acid sequence encoded by a given nucleic acid sequence may also be encoded by a number of "degenerate" nucleic acid sequence which are apparent to those skilled in the art. Thus, the Or83b gene sequences of the present invention also include degenerate variants of the sequences described in (a) through (e), above.

The Or83b gene nucleotide sequences of the invention also encompass: (a) nucleotides that encode an insect Or83b gene product; (b) nucleotides that encode portions of an Or83b gene product that corresponds to one or more of its functional domains including, but not limited to, a signal sequence domain, one or more extracellular domains (ECD), one or more transmembrane domains (TM), one or more cytoplasmic domains (CD) one or more intracellular domains (ID), and one or more odorant-binding domains; (c) nucleotide sequences that encode one or more splice variants of an Or83b gene product including, for example, sequences that encode a splice variant of an Or83b gene product; and (d) nucleotide sequences that encode mutants of an Or83b gene product in which all or part of one of its domains is deleted or altered including, but not limited to, mutants which encode soluble forms of the Or83b gene product in which all or a portion of the TM domain is deleted, and nonfunctional receptors in which all or a portion of a CD is deleted. In yet another embodiment, nucleotides encoding a portion of an Or83b protein characterized as having two or more regions of hydrophobicity with a distribution similar to at least two consecutive hydrophobic peaks as shown in FIG. 8A, FIG. 8C, FIG. 8E or FIG. 8G are provided.

The Or83b gene nucleotide sequences of the invention still further include nucleotide sequences that encode fusion proteins, such as fusion proteins containing any one or more of the Or83b gene products described in (a)-(e) supra fused to another polypeptide. A fusion protein comprises all or part (preferably biologically active) of a polypeptide encoded by an Or83b nucleotide sequence operably linked to a heterologous polypeptide (i.e., a polypeptide other than the same polypeptide of the invention). An exemplary Or83b fusion protein comprises the amino-terminus of a chaperone protein, such as rhodopsin.

The Or83b gene nucleotide sequences of the invention still further include nucleotide sequences corresponding to the above described Or83b gene nucleotide sequences (i.e., the sequences described in (a)-(e) above and fusion proteins thereof) wherein one or more of the exons or fragments thereof, have been deleted.

Still further, the Or83b gene nucleotide sequences of the invention also include nucleotide sequence that have at least 65%, 70%, 75%, 80%, 85%, 90%, 95%, 98% or more nucleotide sequence identity to one or more of the Or83b gene nucleotide sequences of (a)-(e) above. The Or83b gene nucleotide sequences of the invention also include nucleotide sequences encoding polypeptides that have at least 65%, 70%, 75%, 80%, 85%, 90%, 95%, 98% or more amino acid sequence identity to one or more of the polypeptides encoded by any of the Or83b gene nucleotide sequences of (a)-(e) above.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403-0. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score=50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, gapped BLAST, and PSI-Blast programs, the default parameters of the respective programs (e.g., of XBLAST and NBLAST) can be used. Another preferred, non-limiting example of a mathematical algorithm utilized for the comparison of sequences is the algorithm of Myers and Miller, 1988, CABIOS, 4:11-17. Such an algorithm is incorporated in the ALIGN program (version 2.0) which is part of the GCG sequence alignment package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The methods and compositions of the invention also encompass nucleic acid molecules, preferably DNA molecules, that hybridize to and are therefore the complements of the Or83b gene nucleotide sequences (a) through (e) in the preceding paragraph. Such hybridization conditions can be highly stringent or less highly stringent, as described above. The nucleic acid molecules of the invention that hybridize to the above described DNA sequences include oligodeoxyoligonucleotides ("oligos") which hybridize under highly stringent or stringent conditions to the DNA sequences (a) through (e) in the preceding paragraph. In general, for oligos between 14 and 70 nucleotides in length the melting temperature (Tm) is calculated using the formula: Tm(° C.)=81.5+16.6(log [monovalent cations (molar)]+0.41 (% G+C)−(500/N), where N is the length of the probe. If the hybridization is carried out in a solution containing formamide, the melting temperature may be calculated using the equation: Tm(° C.)=81.5+16.6(log [monovalent cations (molar)])+0.41 (% G+C)−(0.61% formamide)−(500/N) where N is the length of the probe. In general, hybridization is carried out at about 20-25 degrees below Tm (for DNA-DNA hybrids) or about 10-15 degrees below Tm (for RNA-DNA hybrids). Other exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos).

These nucleic acid molecules can be used in the methods or compositions of the invention, e.g., as Or83b gene antisense molecules which are useful, for example, in Or83b gene regulation. The sequences can also be used as antisense primers, e.g., in amplification reactions of an Or83b gene nucleic acid sequence. Further, such complementary sequences can be used as part of ribozyme and/or triple helix sequence, also useful for Or83b gene regulation.

Fragments of the Or83b gene and Or83b gene nucleotide sequences of the invention can be at least 10 nucleotides in length. In alternative embodiments, the fragments can be about 20, 30, 40, 50, 60, 70, 80, 90, 100, 200, 300, 400, 500, 1000, 1500, 2000, 2500, 3000, 3500, 4000, 4500 or more contiguous nucleotides in length. Alternatively, the fragments can comprise sequences that encode at least 10, 20, 30, 40, 50, 100, 150, 200, 250, 300, 350, 400, 450, 500 or more contiguous amino acid residues of the Or83b gene products. Fragments of the Or83b gene nucleic acid molecules of the invention can also refer to exons or introns of the above described nucleic acid molecules, as well as portions of the coding regions of such nucleic acid molecules that encode domains such as extracellular domains (ECD), transmembrane domains (TM) and cytoplasmic domains (CD). In certain specific embodiment, the invention provides purified or isolated nucleic acids consisting of at least 8 nucleotides (e.g., a hybridizable portion) of an Or83b gene sequence; in other embodiments, the nucleic acids consist of at least 12 (continuous) nucleotides, 15 nucleotides, 18 nucleotides, 25 nucleotides, 50 nucleotides, 100 nucleotides, 150 nucleotides, or 200 nucleotides of an Or83b odorant receptor sequence, or a full-length Or83b odorant receptor coding sequence. In other embodiments, the nucleic acids consist of at least 120 (continuous) nucleotides, 160 nucleotides, 250 nucleotides, 420 nucleotides, 550 nucleotides, 625 nucleotides, 750 nucleotides, or 1000 nucleotides of an Or83b sequence. In yet other embodiments, the nucleic acids are smaller than 35, 75, 200, 450, 525, or 610 nucleotides in length. In other embodiments, the nucleic acids are 100-200, 200-400, 400-600, 600-800, or larger than 800 nucleotides in length. Nucleic acids can be single or double stranded. As stated above, the invention also relates to nucleic acids hybridizable to or complementary to the foregoing sequences or their reverse complements. In specific aspects, nucleic acids are provided which comprise a sequence complementary to at least 10, 25, 50, 100, or 200 nucleotides or the entire coding region of an Or83b gene. In specific aspects, nucleic acids are provided which comprise a sequence complementary to at least 75, 125, 250, 500, or 650 nucleotides or the entire coding region of an Or83b gene.

In the above or alternative embodiments, the nucleic acids of the invention consist of a nucleotide sequence of not more than 2, 5, 7, 10, 15, or 20 kilobases.

The methods and compositions of the invention also use, and therefore encompass, (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element, such as a heterologous regulatory element, that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. The invention includes fragments of any of the DNA sequences disclosed herein.

In addition to the gene sequences described above, homologs of these gene sequences and/or full length coding sequences of these genes, as can be present in the same or other species, can be identified and isolated, without undue experimentation, by molecular biological techniques well known in the art.

For example, Or83b gene sequences can be labeled and used to screen a cDNA library constructed from mRNA obtained from a genomic or cDNA library of a different insect.

According to this invention, a "genomic DNA library" is a clone library which contains representative nucleotide sequences from the DNA of a given genome. It is constructed using various techniques that are well known in the art, for instance, by enzymatically or mechanically fragmenting the DNA from an organism, organ, or tissue of interest, linking the fragments to a suitable vector, and introducing the vector into appropriate cells so as to establish the genomic library. A genomic library contains both transcribed DNA fragments as well as nontranscribed DNA fragments.

In comparison, a "cDNA library" is a clone library that differs from a genomic library in that it contains only transcribed DNA sequences and no nontranscribed DNA sequences. It is established using techniques that are well known in the art, i.e., selection of mRNA (e.g., by polyA) making single stranded DNA from a population of cytoplasmic mRNA molecules using the enzyme RNA-dependent DNA polymerase (i.e., reverse transcriptase), converting the single-stranded DNA into double-stranded DNA, cloning the resultant molecules into a vector, and introducing the vector into appropriate cells so as to establish the cDNA library. Alternately, a cDNA library need not be cloned into a vector and/or established in cells, but can be screened using PCR with gene-specific primers, as is well known in the art. Particularly useful types of cDNA libraries for identifying Or83b receptors are insect antennal or maxillary palp cDNA libraries.

Hybridization conditions should be of low to moderate stringency when the cDNA library was derived from an insect that is evolutionary divergent from the insect from which the labeled Or83b sequence was derived. cDNA screening can also identify clones derived from alternatively spliced Or83b transcripts in the same or different insect species. Low and moderate stringency conditions will be well known to those of skill in the art, and will vary predictably depending on the specific insects from which the library and the labeled sequences are derived. For guidance regarding such conditions see, for example, Sambrook et al., 1989, *Molecular Cloning, A Laboratory Manual*, Cold Springs Harbor Press, N.Y.; and Ausubel et al., 1989, *Current Protocols in Molecular Biology* (Green Publishing Associates and Wiley Interscience, N.Y.). For example, low stringency conditions include the following: Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Increasing the stringency can be accomplished by use of washing solution and hybridization conditions (e.g., temperature, ionic strength and % SDS) more stringent that those described above. Exemplary moderate stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C.

Further, a previously unknown Or83b gene sequence can be isolated by performing PCR using two degenerate oligonucleotide primer pools designed on the basis of nucleotide sequences within one or more of the above described known Or83b gene sequences.

A "polymerase chain reaction" ("PCR") is a reaction in which replicate copies are made of a target nucleic acid using one or more primers, and a catalyst of polymerization, such as a reverse transcriptase or a DNA polymerase, and particularly a thermally stable polymerase enzyme. Methods for PCR are taught in U.S. Pat. Nos. 4,683,195 (Mullis) and 4,683,202 (Mullis et al.). All processes of producing replicate copies of the same nucleic acid, such as PCR or gene cloning, are collectively referred to herein as "amplification."

The template for the reaction can be cDNA obtained by reverse transcription of mRNA prepared from insect antennal or maxillary palp tissue, or any cultured tissues or cells that are suspected to express the Or83b gene product. The PCR product can be subcloned and sequenced to ensure that the amplified sequences represent the sequences of an Or83b gene nucleic acid sequence. The design of PCR primer pairs is well known in the art. Primers suitable in the present invention are generally capable of encoding at least five, more preferably six contiguous amino acids of the sequences found in highly conserved motifs of Or83b. Thus, they are, at a minimum, preferably 15 to 18 nucleotides in length. The primer pair is chosen such that the reverse primer is downstream of a forward primer. Preferred oligonucleotides for amplification of a portion of an Or83b gene or cDNA are pairs of degenerate oligonucleotide that serve as forward and reverse primers. Thus in one embodiment, suitable forward primer is one that encodes at least six amino acids of SEQ ID NOs:12, 13 or 14, or its complement, and a suitable reverse primer is one that encodes at least six amino acids of SEQ ID NOs:13, 14 or 18, or its complement. Various commercially available programs for primer design are available, for example, MacVector (Oxford Molecular Ltd.) and Vector NTI Suite (Informax, Inc.). Forward and reverse primers are preferably selected such that amplification of an Or83b sequence results in a product of at least 150 nucleotides. Typically, the reverse primer will be chosen from a motif depicted in SEQ ID NOs:13 14 or 18. Thus, when a forward primer is selected from SEQ ID NO:16, the reverse primer may be from SEQ ID Nos:13, 14 or 18. When a forward primer is selected from SEQ ID NO:13, the reverse primer may be from SEQ ID NO:14 or 18. When the forward primer is selected from SEQ ID NO:14, the reverse primer is selected from SEQ ID NO:18. In a preferred embodiment, the forward primer comprises SEQ ID NO:19; the reverse primer comprises SEQ ID NO:20. Suitable amplification conditions for amplification of an Or83b nucleic acid from insect genomic or cDNA include, but are not limited to, using 1 µlg of cDNA or genomic DNA template and 80 pmol each primer in a 50 µl reaction, cycled between 94° C. for 1 min, 51° C. for 1 min, 72° C. for 1 min for a total of 40 cycles. Under such conditions, using antennal cDNA as a template, a forward primer consisting essentially of SEQ ID NO:19 and a reverse primer consisting essentially of SEQ ID NO:20, a product of approximately 235 base pairs can be obtained.

The PCR fragment can then be used to isolate a full length cDNA clone by a variety of methods. For example, the amplified fragment can be used to screen a bacteriophage cDNA library. Alternatively, the labeled fragment can be used to screen a genomic library.

PCR technology can also be utilized to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of cloning strategies which can be used, see e.g., Sambrook et al., 1989, *Molecular Cloning, A Laboratory Manual*, Cold Springs Harbor Press, N.Y.; and Ausubel et al., 1989, *Current Protocols in Molecular Biology*, (Green Publishing Associates and Wiley Interscience, N.Y.).

As will be appreciated by those skilled in the art, DNA sequence polymorphisms of an Or83b gene identified by the methods of the present invention will typically exist within a population of individual insects (e.g., within a locust or medfly population). Such polymorphisms may exist, for example, among individual insects within a population due to natural allelic variation. Such polymorphisms include ones that lead to changes in amino acid sequence. An allele is one of a group of genes which occurs alternatively at a given genetic locus. Accordingly, as used herein, an "allelic variant" refers to a nucleotide sequence which occurs at a given locus or to a gene product encoded by the nucleotide sequence. Natural allelic variations can typically result in 1-5% variance in the nucleotide sequence of a given gene. Certain allelic variations in the nucleotide sequence of a gene may be silent variations, i.e., do not encode a variant protein.

Alternative alleles or allelic variants can be identified by sequencing the gene of interest in a number of different insects of the same species. This can be readily carried out by using PCR amplification of Or83b gene products from genomic DNA from individual insects.

As used herein, the terms "gene" and "recombinant gene" refer to nucleic acid molecules comprising an open reading frame encoding a polypeptide of the invention. The term can further include nucleic acid molecules comprising upstream and/or exon/intron sequences and structure.

With respect to allelic variants of the Or83b genes and gene products of the present invention, any and all nucleotide variations and/or amino acid polymorphisms or variations that are the result of natural allelic variation of the Or83b genes and/or gene products are intended to be within the scope of the present invention. Such allelic variants include, but are not limited to, ones that do not alter the functional activity of the Or83b gene products of the invention. Variants also include, but are not limited to "mutant alleles." As used herein, a "mutant allele" of an Or83b gene or gene product of the invention is an allelic variant which does alter the functional activity of the Or83b gene product. A cDNA of a mutant Or83b gene can be isolated, for example, by using PCR, or by screening a genomic or cDNA library prepared from a population of insects that have the mutant allele. The normal Or83b gene or any suitable fragment thereof can then be labeled and used as a probed to identify the corresponding mutant allele in the library. The clone containing this mutant Or83b gene can then be purified through methods routinely practiced in the art, and subjected to sequence analysis.

Other allelic variants and/or mutant variants of the Or83b genes of the invention include single nucleotide polymorphisms (SNPs), including biallelic SNPs or biallelic markers which have two alleles, both of which are present at a fairly high frequency in a population of organisms. Conventional techniques for detecting SNPs include, e.g., conventional dot blot analysis, single stranded conformational polymorphism (SSCP) analysis (see, e.g., Orita et al., 1989, Proc. Natl. Acad. Sci. USA 86:2766-2770), denaturing gradient gel electrophoresis (DGGE), heteroduplex analysis, mismatch cleavage detection, and other routine techniques well known in the art (see, e.g., Sheffield et al., 1989, Proc. Natl. Acad. Sci. 86:5855-5892; Grompe, 1993, Nature Genetics 5:111-117). Alternative, preferred methods of detecting and mapping SNPs involve microsequencing techniques wherein an SNP site in a target DNA is detected by a single nucleotide primer extension reaction (see, e.g., Goelet et al., PCT Publication No. WO 92/15712; Mundy, U.S. Pat. No. 4,656,127; Vary and Diamond, U.S. Pat. No. 4,851,331; Cohen et al., PCT Publication No. WO 91/02087; Chee et al., PCT Publication No. Wo 95/11995; Landegren et al., 1988, Science 241:1077-1080; Nicerson et al., 1990, Proc. Natl. Acad. Sci. U.S.A. 87:9823-8927; Pastinen et al., 1997, Genome Res. 7:606-614; Pastinen et al., 1996, Clin. Chem. 42:1391-1397; Jalanko et al., 1992, Clin. Chem 38:39-43; Shumaker et al., 1996, Hum. Mutation 7:346-354; Caskey et al., PCT Publication No. 95/00669).

Fragments of Or83b nucleic acids comprising regions conserved between (e.g., with homology to) other Or83b nucleic acids of different insect species, are also provided. Sequence alignment of the amino acid sequences of Or83b genes showed regions of high conservation. In particular, four regions or motifs of at least 11 amino acid residues were found in every insect species tested. These motifs are depicted in SEQ ID NOs:12, 13, 14, and 18. For one motif (SEQ ID NO:14), the flanking regions were found to be highly conserved, with only single amino acid substitutions and are included. In a preferred embodiment, fragments of Or83b nucleic acids comprising regions conserved other Or83b nucleic acids contain at least 15, 20, 30 or 50 contiguous nucleotides corresponding to a highly conserved motif of Or83b, such as those encoding all or portions of the amino acid motifs of SEQ ID NOs:12, 13, 14 and 18. In certain preferred embodiments, the fragment is not found in *D. melanogaster*.

In a specific embodiment, a novel Or83b odorant receptor gene may be identified using a program such as the TBLASTN program (Altschul et al., 1997, Nuc. Acids Res. 25:3389-3402) to query the a database of interest with an Or83b odorant receptor gene sequence in order to identify a contiguous sequence of interest. Individual EST sequences contributing to the contiguous sequence of interest may be identified and a RACE strategy (rapid amplification of cDNA ends) may be used to extend the available sequence to obtain the complete coding region encoded by the novel Or83b gene.

The above-described methods are not meant to be limiting with respect to the methods by which clones of odorant receptor genes may be obtained.

5.2. Expression of insect Or83b Odorant Receptor Genes

The nucleotide sequence coding for an Or83b odorant receptor protein or a functionally active analog or fragment or other derivative thereof can be inserted into an appropriate expression vector, e.g., a vector which contains the necessary elements for the transcription and translation of the inserted protein-coding sequence. The necessary transcriptional and translational signals can also be supplied by the native odorant receptor gene and/or its flanking regions. Thus, the nucleotide sequence is operatively linked to a promoter. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In yet another embodiment, a fragment of an Or83b odorant receptor protein comprising one or more motifs of the Or83b odorant receptor protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding an Or83b odorant receptor protein or peptide fragment may be regulated by a second nucleic acid sequence so that the Or83b odorant receptor polypeptide is expressed in a host transformed with the recombinant DNA molecule. For example, expression of an Or83b odorant receptor protein may be controlled by any promoter/enhancer element known in the art. A promoter/enhancer may be homologous (e.g., native) or heterologous (e.g., not native). Promoters which may be used to control Or83b odorant receptor gene expression include, but are not limited to, the SV40 early promoter region (Benoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the regulatory sequence of the human cytomegalovirus for expression in any tissues (Foecking, M. and Hofstetter, H., 1986, Gene 45:101-105; U.S. Pat. No. 5,168,062), prokaryotic expression vectors such as the β-lactamase promoter (Villa-Kamaroff et al., 1978, Proc. Natl. Acad. Sci. U.S.A. 75:3727-3731), or the lac promoter (DeBoeref et al., 1983, Proc. Natl. Acad. Sci. U.S.A. 80:21-25; Scientific American, 1980, 242:74-94), plant expression vectors comprising the nopaline synthetase promoter region (Herrera-Estrella et al., Nature 303:209-213), the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120), promoter elements from yeast or other fungi such as the Gal4-responsive promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); a gene control region which is active in pancreatic beta cells (Hanahan, 1985, Nature 315:115-122), an immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to an Or83b odorant receptor gene nucleic acid, one or more origins of replication, and, optionally, one or more selectable markers (e.g., an antibiotic resistance gene).

In a specific embodiment, an expression construct is made by subcloning an Or83b odorant receptor coding sequence into the EcoRI restriction site of each of the three pGEX vectors (Glutathione S-Transferase expression vectors; Smith and Johnson, 1988, Gene 7:31-40). This allows for the expression of the odorant receptor protein product from the subclone in the correct reading frame.

In another specific embodiment, the promoter that is operably linked to the insect Or83b odorant receptor gene is not the native insect Or83b odorant receptor gene promoter (e.g., it is a heterologous promoter).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors {e.g., lambda phage), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered odorant receptor protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce a non-glycosylated core protein product. Expression in yeast will produce a glycosylated product. Expression in animal cells, including insect and mammalian cells and Xenopus oocytes, can be used to ensure "native" glycosylation of an Or83b protein.

In other specific embodiments, the Or83b odorant receptor protein, fragment, analog, or derivative may be expressed as a fusion, or chimeric protein product (comprising the protein, fragment, analog, or derivative joined via a peptide bond to a heterologous protein sequence (of a different protein)). A chimeric protein may include fusion of the Or83b odorant receptor protein, fragment, analog, or derivative to a second protein or at least a portion thereof, wherein a portion is one (preferably 10, 15, 20, 30, or 50) or more amino acids of said second protein. The second protein, or one or more amino acid portion thereof, may be from a different insect odorant receptor protein or may be from a protein that is not an insect odorant receptor protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

5.3. Insect Or83b Gene Products

In particular aspects, the invention provides amino acid sequences of Or83b proteins and fragments and derivatives thereof which comprise an antigenic determinant (e.g., can be recognized by an antibody) or which are otherwise functionally active, as well as nucleic acid sequences encoding the foregoing. "Functionally active" odorant receptor material as used herein refers to that material displaying one or more functional activities associated with a full-length (wild-type) odorant receptor protein, e.g., binding to an Or83b associated protein or binding to a specific nucleotide or DNA sequence antigenicity (binding to an anti-odorant receptor protein antibody), immunogenicity, modulating the activity of a G protein, and/or binding to an Or83b ligand.

The present invention further provides polypeptides having amino sequences encoded by any of the nucleic acid sequences.

In specific embodiments, the invention provides fragments of an Or83b odorant receptor protein consisting of at least 10 amino acids, 20 amino acids, 50 amino acids, or of at least 75 amino acids. In other specific embodiments, the invention provides fragments of an Or83b odorant receptor protein consisting of at least 100 amino acids, 150 amino acids, 200 amino acids, 250 amino acids, or of at least 300 amino acids. In other specific embodiments, the invention provides fragments of an Or83b protein consisting of at least 85 amino acids, 175 amino acids, 275 amino acids, 310 amino acids, or of at least 325 amino acids. Fragments, or proteins comprising fragments, lacking some or all of the foregoing regions of an Or83b protein are also provided. Nucleic acids encoding the foregoing are provided. In specific embodiments, the nucleic acids are less than 5 or 10 kilobases. In specific embodiments, the foregoing proteins or fragments are not more than 25, 50, 100, or 200 contiguous amino acids.

Once a recombinant which expresses the Or83b odorant receptor gene sequence is identified, the gene product can be analyzed. This is achieved by assays based on the physical or functional properties of the product, including radioactive labeling of the product followed by analysis by gel electrophoresis, immunoassay, etc.

Once the Or83b odorant receptor protein is identified, it may be isolated and purified by standard methods including chromatography (e.g., ion exchange, affinity, and sizing column chromatography), centrifugation, differential solubility, or by any other standard technique for the purification of proteins.

Alternatively, once an Or83b odorant receptor protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller et al., 1984, Nature 310:105-111).

In another alternate embodiment, native Or83b odorant receptor proteins can be purified from natural sources, by standard methods such as those described above (e.g., immunoaffinity purification).

In a specific embodiment of the present invention, such Or83b odorant receptor proteins, whether produced by recombinant DNA techniques or by chemical synthetic methods or by purification of native proteins, include but are not limited to those containing, as a primary amino acid sequence, all or part of the amino acid sequence substantially as set forth in SEQ ID NO:2, SEQ ID NO:4, SEQ ID NO:6, or SEQ ID NO:8, as well as fragments and other derivatives, and analogs thereof, including proteins homologous thereto.

The invention further relates to odorant receptor proteins, derivatives (including but not limited to fragments), analogs, and molecules of odorant receptor proteins. As used herein, a molecule defined by a particular SEQ ID NO, shall be construed to mean that the sequence of that molecule consists of that SEQ ID NO. Nucleic acids encoding Or83b odorant receptor protein derivatives and protein analogs are also provided. In one embodiment, the Or83b odorant receptor proteins are encoded by the Or83b odorant receptor nucleic acids described in Section 5.1 above. In particular aspects, the proteins, derivatives, or analogs are of Or83b odorant receptor proteins encoded by the sequence set forth in SEQ ID NO:1, SEQ ID NO:3, SEQ ID NO:5, or SEQ ID NO:7.

The production and use of derivatives and analogs related to an Or83b odorant receptor protein are within the scope of the present invention. In a specific embodiment, the derivative or analog is functionally active, e.g., capable of exhibiting one or more functional activities associated with a full-length, wild-type Or83b odorant receptor protein. As one example, such derivatives or analogs which have the desired immunogenicity or antigenicity can be used in immunoassays, for immunization, for inhibition of Or83b odorant receptor activity, etc. As yet another example, such derivatives or analogs which have the desired binding activity can be used for binding to an Or83b odorant ligand (see e.g., Levine, A., et al., 1997, Cell 88:323-331). Derivatives or analogs that retain, or alternatively lack or inhibit, a desired Or83b odorant receptor protein property-of-interest (e.g., binding to an Or83b protein binding partner), can be used as inducers, or inhibitors, respectively, of such property and its physiological correlates. A specific embodiment relates to an Or83b odorant receptor protein fragment that can be bound by an anti-Or83b odorant receptor protein antibody. Derivatives or analogs of an Or83b odorant receptor protein can be tested for the desired activity by procedures known in the art, including but not limited to the assays described below.

In particular, Or83b odorant receptor derivatives can be made by altering odorant receptor sequences by substitutions, additions (e.g., insertions) or deletions that provide for functionally equivalent molecules. Due to the degeneracy of nucleotide coding sequences, other DNA sequences which encode substantially the same amino acid sequence as an Or83b odorant receptor gene may be used in the practice of the present invention. These include but are not limited to nucleotide sequences comprising all or portions of an Or83b gene which is altered by the substitution of different codons that encode a functionally equivalent amino acid residue within the sequence, thus producing a silent change. Likewise, the Or83b odorant receptor derivatives of the invention include, but are not limited to, those containing, as a primary amino acid sequence, all or part of the amino acid sequence of an Or83b protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins consisting of or comprising a fragment of an Or83b odorant receptor protein consisting of at least 10 (continuous) amino acids of the Or83b odorant receptor protein is provided. In other embodiments, the fragment consists of at least 20 or at least 30 or at least 50 amino acids of the odorant receptor protein. In specific embodiments, such fragments are not larger than 35, 100 or 200 amino acids. In specific embodiments, such fragments are 30-50, 50-100, 100-220, or 200-390 amino acids. Derivatives or analogs of Or83b odorant receptor proteins include but are not limited to those molecules comprising regions that are substantially homologous to an Or83b protein or fragment thereof (e.g., in various embodiments, at least 60% or 70% or 80% or 90% or 95% identity over an amino acid sequence of identical size without any insertions or deletions or when compared to an aligned sequence in which the alignment is done by a computer homology program known in the art) or whose encoding nucleic acid is capable of hybridizing to a coding odorant receptor gene sequence, under high stringency, moderate stringency, or low stringency conditions. In preferred embodiments, the fragment is not found in *D. melanogaster* or is not the Or83b polypeptide of *D. melanogaster*.

Based on the sequence alignment, Or83b genes are expected to encode proteins with a high degree of conservation in the C-terminus. Preferred Or83b polypeptides and polypeptide fragments have at least 10 contiguous amino acids from the motifs identified in FIG. 7, including the motifs of SEQ ID NOs:12, 13, 14 and 18. Motifs of at least 15 or 20 contiguous amino acids are also contemplated. Preferably, the Or83b genes encode proteins that have more than one highly conserved motif. More preferably, they contain three or all four highly conserved motifs.

The Or83b odorant receptor derivatives and analogs of the invention can be produced by various methods known in the art. The manipulations which result in their production can occur at the gene or protein level. For example, a cloned Or83b odorant receptor gene sequence can be modified by any of numerous strategies known in the art (Sambrook et al., 1989, *Molecular Cloning, A Laboratory Manual*, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified gene encoding a derivative or analog of an Or83b protein, care should be taken to ensure that the modified gene remains within the same translational reading frame as the native protein, uninterrupted by translational stop signals, in the gene region where the desired odorant receptor protein activity is encoded.

Additionally, an Or83b odorant receptor nucleic acid sequence can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253: 6551), use of TAB® linkers (Pharmacia), PCR with primers containing a mutation, etc.

Manipulations of an Or83b odorant receptor protein sequence may also be made at the protein level. Included within the scope of the invention are odorant receptor protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In addition, analogs and derivatives of an Or83b odorant receptor protein can be chemically synthesized. For example, a peptide corresponding to a portion of an Or83b protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the odorant receptor sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, an Or83b odorant receptor protein derivative is a chimeric or fusion protein comprising an Or83b odorant receptor protein or fragment thereof (preferably consisting of at least a domain or motif of the odorant receptor protein, or at least 10 amino acids of the Or83b odorant receptor protein) joined at its amino- or carboxy-terminus via a peptide bond to an amino acid sequence of a different protein. In specific embodiments, the amino acid sequence of the different protein is at least 6, 10, 20 or 30 continuous amino acids of the different proteins or a portion of the different protein that is functionally active. In specific embodiments, the amino acid sequence of the different protein is at least 50, 75, 100, or 150 continuous amino acids of the different proteins or a portion of the different protein that is functionally active. In one embodiment, such a chimeric protein is produced by recombinant expression of a nucleic acid encoding the protein (comprising an Or83b odorant receptor-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of an Or83b odorant receptor gene fused to any heterologous protein-encoding sequences may be constructed. A specific embodiment relates to a chimeric protein comprising a fragment of an Qr83b odorant receptor protein of at least six amino acids, or a fragment that displays one or more functional activities of the odorant receptor protein.

In another specific embodiment, the Or83b odorant receptor derivative is a molecule comprising a region of homology with an Or83b odorant receptor protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region without any insertions or deletions or when compared to an aligned sequence of the second region that has been aligned by a computer homology program known in the art. For example, a molecule can comprise one or more regions homologous to an Or83b odorant receptor domain or a portion thereof.

In a specific embodiment, the invention relates to Or83b odorant receptor derivatives and analogs, in particular Or83b odorant receptor fragments and derivatives of such fragments, that comprise, or alternatively consist of, one or more domains of an Or83b odorant receptor protein.

In another specific embodiment, a molecule is provided that comprises one or more domains (or functional portion thereof) of an Or83b odorant receptor protein but that also lacks one or more domains (or functional portion thereof) of an Or83b odorant receptor protein. By way of example, such a protein may retain such domains separated by a spacer. In another embodiment, a molecule is provided that comprises one or more domains (or functional portion(s) thereof) of an Or83b odorant receptor protein, and that has one or more mutant (e.g., due to deletion or point mutation(s)) domains of an Or83b odorant receptor protein (e.g., such that the mutant domain has decreased or increased function compared to wild type).

5.4. Structure of Insect Or83b Odorant Receptor Genes and Proteins

The structure of Or83b odorant receptor genes and proteins of the invention can be analyzed by various methods known in the art. Some examples of such methods are described below.

5.4.1. Genetic Analysis

The cloned DNA or cDNA corresponding to an Or83b odorant receptor gene can be analyzed by methods including but not limited to Southern hybridization (Southern, 1975, J. Mol. Biol. 98:503-517), Northern hybridization (see e.g., Freeman et al., 1983, Proc. Natl. Acad. Sci. U.S.A. 80:4094-4098), restriction endonuclease mapping (Maniatis, 1982, *Molecular Cloning, A Laboratory Manual*, Cold Spring Harbor Laboratory Press, Cold Spring Harbor, N.Y.), and DNA sequence analysis. Accordingly, this invention provides nucleic acid probes recognizing an Or83b odorant receptor gene. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85:7652-7656; Ochman et al., 1988, Genetics 120:621-623; Loh et al., 1989, Science 243:217-220) followed by Southern hybridization with an Or83b odorant receptor gene-specific probe can allow the detection of an Or83b odorant receptor gene in DNA from various cell types, such as olfactory neurons in antennae and maxillary palps. Methods of amplification other than PCR are commonly known and can also be employed. In one embodiment, Southern hybridization can be used to determine the genetic linkage of an Or83b odorant receptor gene. Northern hybridization analysis can be used to determine the expression of an Or83b odorant receptor gene. The stringency of the hybridization conditions for both Southern and Northern hybridization can be manipulated to ensure detection of nucleic acids with the desired degree of relatedness to the specific Or83b odorant receptor gene probe used. Modifications of these methods and other methods commonly known in the art can be used.

In a preferred specific embodiment of the invention, Northern hybridization is performed using different poly(A)+ mRNA preparations (e.g., cells treated or untreated with DNA damaging agents) which were fractionated on an agarose gel along with size standards and blotted to a nylon membrane. A DNA fragment containing an Or83b coding region is excised from a clone digested with an appropriate restriction endonuclease, separated by electrophoresis in an agarose gel, extracted from the gel, and $^{32}$P-labeled by random-priming using the Rediprime labeling system (Amersham). Hybridization of the labeled probe to the mRNA blot is performed overnight. The blot is washed at high stringency (0.2×SSC/0.1% SDS at 65° C.) and mRNA species that specifically hybridized to the probe are detected by autoradiography using X-ray film.

Restriction endonuclease mapping can be used to roughly determine the genetic structure of an Or83b odorant receptor gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499-560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. Protein Analysis

The amino acid sequence of an Or83b odorant receptor protein can be derived by deduction from the DNA sequence, or alternatively, by direct sequencing of the protein, e.g., with an automated amino acid sequencer.

An Or83b odorant receptor protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of the Or83b odorant receptor protein and the corresponding regions of the gene sequence which encode such regions.

Structural prediction analysis (Chou and Fasman, 1974, Biochemistry 13:222) can also be done, to identify regions of an Or83b protein that assume specific secondary structures.

Manipulation, translation, and secondary structure prediction, open reading frame prediction and plotting, as well as determination of sequence homologies, can also be accomplished using computer software programs available in the art (see Section 5.2).

Other methods of structural analysis can also be employed. These include but are not limited to X-ray crystallography (Engstom, 1974, Biochem. Exp. Biol. 11:7-13), nuclear magnetic resonance spectroscopy (Clore and Gonenborn, 1989, CRC Grit. Rev. Biochem. 24:479-564) and computer modeling (Fletterick and Zoller, 1986, Computer Graphics and Molecular Modeling, in *Current Communications in Molecular Biology*, Cold Spring Harbor Laboratory Press, Cold Spring Harbor, N.Y.).

5.5. Assays of Or83b Protein Derivatives

The functional activity of Or83b odorant receptor proteins, derivatives and analogs can be assayed by various methods known to one skilled in the art.

For example, in one embodiment, where one is assaying for the ability to bind to or compete with a wild-type Or83b odorant receptor protein for binding to an anti-Or83b antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. In another embodiment, where an Or83b odorant receptor-binding protein is identified, the binding can be assayed, e.g., by means well-known in the art.

In another embodiment, genetic studies can be done to study the phenotypic effect of an Or83b gene mutant that is a derivative or analog of a wild-type odorant receptor gene. Other such methods will be readily apparent to the skilled artisan and are within the scope of the invention.

In yet other embodiments, assays of Or83b derivatives and fragments can be assayed for their ability to modulate G protein activity, or to bind ligand, as described in the screening assays in Section 5.8, infra.

5.6. Antibodies

According to the invention, an Or83b protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and a Fab expression library. In another embodiment, antibodies to a domain of an Or83b odorant receptor protein are produced. In a specific embodiment, fragments of an Or83b odorant receptor protein identified as hydrophilic are used as immunogens for antibody production.

Various procedures known in the art may be used for the production of polyclonal antibodies to an Or83b odorant receptor protein or derivative or analog. In a particular embodiment, rabbit polyclonal antibodies to an epitope of an Or83b protein consisting of the sequence as set forth in SEQ ID NO:2, SEQ ID NO:4, SEQ ID NO:6, or SEQ ID NO:8, or a subsequence thereof, can be obtained. For the production of antibody, various host animals can be immunized by injection with the native odorant receptor protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed to an Or83b odorant receptor protein sequence or analog thereof, any technique which provides for the production of antibody molecules by continuous cell lines in culture may be used. For example, the hybridoma technique originally developed by Kohler and Milstein (Kohler and Milstein 1975, Nature 256: 495-497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77-96). In an additional embodiment of the invention, monoclonal antibodies can be produced in germ-free animals (see e.g., PCT/US90/022548). According to the invention, human antibodies may be used and can be obtained by using human hybridomas (Cole et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for an Or83b protein together with genes from a human antibody molecule of appropriate biological activity can be used; such antibodies are within the scope of this invention. In another embodiment, "humanized" antibodies are also provided by the invention (U.S. Pat. No. 5,225,539)

According to the invention, techniques described for the production of single chain antibodies (U.S. Pat. No. 4,946,778) can be adapted to produce Or83b odorant receptor-specific single chain antibodies. An additional embodiment of the invention utilizes the techniques described for the construction of Fab' expression libraries (Huse et al., 1989, Science 246:1275-1281) to allow rapid and easy identification of monoclonal Fab fragments with the desired specificity for Or83b odorant receptor proteins, derivatives, or analogs.

Antibody fragments which contain the idiotype of the molecule can be generated by known techniques. For example, such fragments include but are not limited to, the $F(ab')_2$ fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art (e.g., enzyme-linked immunosorbent assay or ELISA). For example, to select antibodies which recognize a specific domain of an Or83b odorant receptor protein, one may assay generated hybridomas for a product which binds to an Or83b odorant receptor fragment containing such domain. For selection of an antibody that specifically binds a first Or83b odorant receptor homolog but which does not specifically bind a different Or83b odorant receptor homolog, one can select on the basis of positive binding to the first odorant receptor homolog and a lack of binding to the second odorant receptor homolog.

Antibodies specific to a domain of an Or83b odorant receptor protein are also provided. Antibodies specific to an epitope of an Or83b odorant receptor protein are also provided.

5.7. Identification of Compounds that Bind to Or83b Proteins

This invention provides screening methodologies useful in the identification of proteins and other compounds which bind to, or otherwise directly interact with, the Or83b odorant receptor genes and proteins. Such compounds will include molecules that agonize or antagonize Or83b function.

Screening methodologies are well known in the art (see e.g., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the Or83b odorant receptor genes and proteins.

Alternatively, any of a variety of exogenous compounds, both naturally occurring and/or synthetic {e.g., libraries of small molecules or peptides), may be screened for binding capacity. Binding compounds can include, but are not limited to, other cellular proteins. Binding compounds can also include, but are not limited to, peptides such as, for example, soluble peptides, including, but not limited to, Ig-tailed fusion peptides (see, e.g., Lam et al., 1991, Nature 354:82-84; Houghten et al., 1991, Nature 354:84-86), antibodies (including, but not limited to polyclonal, monoclonal, human, humanized, anti-idiotypic, chimeric or single chain antibodies, and FAb, F(ab')$_2$ and FAb expression library fragments, and epitope-binding fragments thereof), and small organic or inorganic molecules. Such compounds can include organic molecules (e.g., peptidomimetics) that bind to the ECD and either mimic the activity triggered by the natural odorant ligand (i.e., agonists); as well as peptides, antibodies or fragments thereof, and other organic compounds that mimic the ECD (or a portion thereof) and bind to and "neutralize" natural odorant ligand. Such compounds identified in a screen for binding to Or83b can be assayed for their effects on Or83b signaling, as described in Section 5.8, infra.

Computer modeling and searching technologies permit identification of compounds that can modulate Or83b activity. Having identified such a compound or composition, the active sites or regions are preferably identified. Such active sites might typically be odorant ligand binding sites, such as the interaction domains of odorant ligands with Or83b polypeptides. The active site can be identified using methods known in the art including, for example, from the amino acid sequences of peptides, from the nucleotide sequences of nucleic acids, or from study of complexes of Or83b polypeptides with their natural ligands. In the latter case, chemical or X-ray crystallographic methods can be used to find the active site by finding where on the Or83b polypeptides the complexed odorant ligand is found.

The three dimensional geometric structure of the active site can also be determined. This can be done by known methods, including X-ray crystallography, which can determine a complete molecular structure. Solid or liquid phase NMR can also be used to determine certain intra-molecular distances within the active site and/or in the odorant ligand/Or83b complex. Any other experimental method of structure determination can be used to obtain partial or complete geometric structures. The geometric structures may be measured with a complexed odorant ligand, natural or artificial, which may increase the accuracy of the active site structure determined.

Methods of computer based numerical modeling can be used to complete the structure (e.g., in embodiments wherein an incomplete or insufficiently accurate structure is determined) or to improve its accuracy. Any art recognized modeling method may be used, including, but not limited to, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. Exemplary forcefields that are known in the art and can be used in such methods include, but are not limited to, the Constant Valence Force Field (CVFF), the AMBER force field and the CHARM force field. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential target or pathway polypeptide modulating compounds found from this search are potential target or pathway polypeptide modulating compounds.

Alternatively, these methods can be used to identify improved modulating compounds from an already known modulating compound or odorant ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified binding compounds or odorant ligands of improved specificity or activity.

Examples of molecular modeling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, Jun. 16, 1988, New Scientist 54-57; McKinaly and Rossmann, 1989, Annu. Rev. Pharmacol. Toxiciol. 29:111-122; Perry and Davies, OSAR: Quantitative Structure-Activity Relationships in Drug Design pp. 189-193 (Alan R. Liss, Inc. 1989); and Lewis and Dean, 1989, Proc. R. Soc. Lond. 236: 125-140 and 1-162. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario).

Although generally described above with reference to design and generation of compounds which could alter binding, one could also screen libraries of known compounds, including natural products or synthetic chemicals, and biologically active materials, including proteins, for compounds which bind to Or83b polypeptides.

Assays for identifying additional compounds as well as for testing the effectiveness of compounds, identified by, for example, techniques, such as those described in Section 5.8, are discussed, below, in Section 5.8. As will be apparent to one of ordinary skill in the art, there are numerous other methods of screening individual proteins or other compounds, as well as large libraries of proteins or other compounds (e.g., phage display libraries) to identify molecules which bind to Or83b odorant receptor proteins. All of these methods comprise the step of mixing an Or83b odorant receptor protein, fragment or mutant, or a composition comprising said Or83b odorant receptor protein, fragment or mutant, including but not limited to a cultured cell, with test compounds, allowing time for any binding to occur, and assaying for any bound complexes, as described in further detail below.

5.7.1. Screening for Small Molecules that Bind to Or83b In Vivo

In particular, methods are provided for identifying a molecule that binds to an Or83b receptor protein. In one embodiment, the method comprises contacting a cell that expresses the Or83b receptor with a test molecule, or plurality of test molecules, under conditions conducive to binding between the receptor and the test molecule, and determining whether the test molecule binds to the cell. A molecule that binds to an Or83b receptor, but not to a counterpart cell that does not express an Or83b receptor, can be identified thereby.

In an alternative embodiment, a molecule that binds to an Or83b receptor from a first species but not from a second species is identified. This method comprises contacting two different species of cells that both express an Or83b receptor with a test molecule under conditions conducive to binding of the receptor and the test molecule. The binding of the test molecule to the cells is tested. Test molecules that bind to Or83b receptor on the first cell but not the second cell are identified.

In an alternative embodiment, a method is provided for identifying a molecule that binds to first insect olfactory receptor but not a second insect olfactory receptor. The method comprises contacting a first cell that expresses the Or83b receptor and a first olfactory receptor and a second cell that expresses the Or83b receptor and a second olfactory receptor, with a test molecule, or plurality of test molecules, under conditions conducive to binding between the receptor and the test molecule, and determining whether the test molecule binds to the cells. A molecule that binds to the first cell, and therefore first olfactory receptor, but not the second cell and second insect olfactory receptor can be identified thereby.

In an alternative embodiment, a method is provided for identifying a molecule that binds to an insect Or83b receptor but not an insect gustatory receptor. The method comprises contacting a first cell that expresses the Or83b receptor and a second cell that expresses an insect gustatory receptor, with a test molecule, or plurality of test molecules, under conditions conducive to binding between the receptor and the test molecule, and determining whether the test molecule binds to the cells. A molecule that binds to the first cell, and therefore an Or83b receptor, but not the second cell and insect gustatory receptor can be identified thereby.

5.7.2. Screening for Small Molecules that Bind to Or83b In Vitro

In vitro systems can be designed to identify compounds capable of binding the Or83b polypeptides of the invention. Compounds identified can be useful, for example, in modulating the activity of wild type Or83b, and thereby modulating insect behavior.

The principle of the assays used to identify compounds that bind to the Or83b polypeptide involves preparing a reaction mixture of an Or83b polypeptide and a test compound under conditions and for a time sufficient to allow the two components to interact and bind, thus forming a complex which can be removed and/or detected in the reaction mixture. These assays can be conducted in a variety of ways. For example, one method to conduct such an assay involves anchoring Or83b polypeptide or the test substance onto a solid phase and detecting Or83b polypeptide/test compound complexes anchored on the solid phase at the end of the reaction. In one embodiment of such a method, the Or83b polypeptide can be anchored onto a solid surface, and the test compound, which is not anchored, can be labeled, either directly or indirectly.

In practice, microtiter plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the Or83b polypeptide or the test compound to anchor any complexes formed in solution, and a labeled antibody specific for the other component of the possible complex to detect anchored complexes.

As an example, and not by way of limitation, techniques such as those described in this section can be utilized to identify compounds which bind to the Or83b polypeptide. For example, an Or83b polypeptide can be contacted with a compound for a time sufficient to form an Or83b polypeptide/compound complex and then such a complex can be detected. Alternatively, the compound can be contacted with the Or83b polypeptide in a reaction mixture for a time sufficient to form an Or83b polypeptide/compound complex, and then such a complex can be separated from the reaction mixture.

5.8. Screening for Molecules that Modulate Or83b Activity

Particularly useful molecules that bind to or modulate Or83b protein activity are small molecules, most preferably volatile small molecules, that function as odorant. The term "odorant" as employed herein refers to a molecule that has the potential to bind to an olfactory receptor. Equivalent terms employed herein include "odorant ligand", "odorant molecule" and "odorant compound". The term "binding" or "interaction" as used herein with respect to odorant ligands refers to the interaction of ligands with the receptor polypeptide where the ligands may serve as either agonists and/or antagonists of a given receptor or receptor function. This effect may not be direct, but merely by altering the binding of an odorant receptor to another ligand. An odorant ligand may thus directly cause a perception of odor (an agonist), or may block the perception of odor (an antagonist). An odorant ligand may include, but is not limited to, molecules which interact with polypeptides involved in olfactory sensation. Odorant ligands and molecules which interact with olfactory receptors are generally small, approximately 1 kD, more preferably approximately 0.75 kD, more preferably approximately 0.5 kD, or even more preferably approximately 0.3 kD, hydrophobic molecules with a variety of functional groups. Small changes in structure can induce profound changes in odorant ligand binding and hence in the odor perceived by an individual. In a specific embodiment, the odorant ligand is an Or83b ligand, i.e., a ligand that binds to an Or83b receptor alone or an Or83b receptor in conjunction with a classical odorant receptor.

Thus, the present invention provides methods for screening for molecules, more preferably small molecules, most preferably volatile molecules, that modulate Or83b receptor activity. Methods for screening odorant compounds using odorant receptors in neuronal cells are known in the art (Firestein et al., WO 98/50081; Duchamp-Viret et al., 1999, Science 284:2171-2174; Sato et al., 1994, J. Neurophys. 72:2980-2989; Malnic et al., 1999, Cell 96:713-723; Zhao et al., 1998, Science 279:237-242). There are also methods which can be employed to screen odorant compounds which do not require neuronal cells and are known in the art (Kauvar et al., U.S. Pat. No. 5,798,275; Kiefer et al., 1996, Biochemistry 35:16077-16084; Krautwurst et al., 1998, Cell 95:917-926).

In a particular embodiment, a method is provided for identifying a modulator of an Or83b receptor protein. The method comprises contacting a first cell that expresses the Or83b receptor with a test molecule, or plurality of test molecules, under conditions conducive to binding between the receptor and the test molecule, and determining whether the test molecule modulates G-protein activity in the first cell but not in a second cell which does not express the Or83b receptor. A molecule that modulates an Or83b receptor can be identified thereby.

In an alternative embodiment, a molecule that modulates an Or83b receptor from a first species but not from a second species is identified. This method comprises contacting two different species of cells that both express an Or83b receptor with a test molecule under conditions conducive to binding of the receptor and the test molecule. The G-protein activity in the cells is measured. Test molecules that modulate G-protein activity of the Or83b receptor on the first cell but not the second cell are identified.

In an alternative embodiment, a method is provided for identifying an odorant that modulates the activity of first insect olfactory receptor but not a second insect olfactory receptor. The method comprises contacting a first cell that expresses the Or83b receptor and a first olfactory receptor and a second cell that expresses the Or83b receptor and a second olfactory receptor, with a test molecule, or plurality of test molecules, under conditions conducive to binding between the receptor and the test molecule, and determining whether the test molecule binds to the cells. A molecule that modulates the first cell, and therefore first olfactory receptor, but not the second cell and second insect olfactory receptor can be identified thereby.

In an alternative embodiment, a method is provided for identifying a molecule that modulates an insect Or83b receptor but not an insect gustatory receptor. The method comprises contacting a first cell that expresses the Or83b receptor and a second cell that expresses an insect gustatory receptor, with a test molecule, or plurality of test molecules, under conditions conducive to binding between the receptor and the test molecule, and determining whether the test molecule modulates G-protein activity in the cells. A molecule that modulates G-protein activity in the first cell, and therefore an Or83b receptor, but not the second cell and insect gustatory receptor can be identified thereby.

Several methods of measuring G-protein activity are known to those of skill in the art and can be used in conjunction with the methods of the present invention, including but not limited to measuring calcium ion or cyclic AMP concentration in the cells. Such methods are described in Howard et al., 2001, Trends Pharmacol Sci. 22 (3):132-40; Krautwurst et al., 1999, Cell 95:917-926; Chandrashekar et al., 2000, Cell. 100 (6):703-11; and Oda et al., 2000, J Biol Chem. 275 (47):36781-6, which are incorporated by reference herein in their entireties.

In certain specific embodiments, intracellular calcium concentration is measured in the screening assays of the instant application by using a Fluorometric Imaging Plate Reader ("FLIPR") system (Molecular Devices, Inc.), which provides the advantages automated, high-throughput screening, see also Sullivan et al., 1999, "Measurement of $[Ca^{2+}]i$ using the fluorometric imaging plate reader (FLIPR)," In Calcium Signaling Protocols, ed Lambert, D. G., pp. 125-136 (New Jersey: Humana Press); or as described by Offermanns and Simon, 1995, J. Biol. Chem. 270 (25):15175-80; Ungrin et al., 1999, Anal Biochem. 272 (1):34-42; or in U.S. Pat. No. 6,004,808, which employs Fura-PE3 (Molecular Probes, Inc., Eugene, Oreg.) as a stain of calcium ions. Calcium ion concentration is proportional to Or83b G protein activity.

In another specific embodiment, cAMP concentration is measured in the screening assays of the instant application by the method of Fitzgerald et al., Anal. Biochem. 275 (1):54-61. cAMP concentration is proportional to Or83b receptor activity.

5.8.1. Proteins which Interact with Or83b Polypeptides

The present invention further provides methods of identifying or screening for proteins which interact with Or83b odorant receptor proteins, or derivatives, fragments, mutants or analogs thereof.

Any method suitable for detecting protein-protein interactions can be employed for identifying novel Or83b protein-cellular protein interactions. Among the traditional methods which can be employed are co-immunoprecipitation, crosslinking and co-purification through gradients or chromatographic columns. Utilizing procedures such as these allows for the identification of proteins that interact with an Or83b polypeptide. Once identified, such proteins can be used, for example, to disrupt Or83b signaling through the endogenous cellular counterpart of the protein, thereby antagonizing Or83b-induced behaviors. Once identified, such proteins that interact with an Or83b polypeptide can also be used, in conjunction with standard techniques, to identify the corresponding gene that encodes the protein which interacts with the Or83b polypeptide. For example, at least a portion of the amino acid sequence of the polypeptide can be ascertained using techniques well known to those of skill in the art, such as via the Edman degradation technique (see, e.g., Creighton, 1983, *Proteins: Structures and Molecular Principles*, W.H. Freeman & Co., N.Y., pp. 34-49). The amino acid sequence obtained can be used as a guide for the generation of oligonucleotide mixtures that can be used to screen for gene sequences. Screening can be accomplished, for example, by standard hybridization or PCR techniques. Techniques for the generation of oligonucleotide mixtures and for screening are well-known. (See, e.g., Ausubel, supra., and PCR Protocols: A Guide to Methods and Applications, 1990, Innis, M. et al., eds. Academic Press, Inc., New York).

Additionally, methods can be employed which result in the simultaneous identification of genes which encode proteins interacting with an Or83b polypeptide. These methods include, for example, probing expression libraries with labeled Or83b polypeptide, using this protein in a manner similar to the well known technique of antibody probing of λgt11 libraries.

One method which detects protein interactions in vivo, the two-hybrid system, is described in detail for illustration purposes only and not by way of limitation. One version of this system has been described (Chien et al., 1991, Proc. Natl. Aca. Sci. U.S.A. 88:9578-9582) and is commercially available from Clontech (Palo Alto, Calif.).

Briefly, utilizing such, a system, plasmids are constructed that encode two hybrid proteins: one consists of the DNA-binding domain of a transcription activator protein fused to a known protein, in this case, an Or83b polypeptide, and the other consists of the activator protein's activation domain fused to an unknown protein that is encoded by a cDNA, preferably an insect antennal or maxillary palp cDNA, which has been recombined into this plasmid as part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene, the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter polypeptide.

The two-hybrid system or related methodology can be used to screen activation domain libraries for proteins that interact with a known "bait" polypeptide. By way of example, and not by way of limitation, Or83b polypeptides can be used as the bait polypeptides. Total genomic or cDNA sequences are fused to the DNA encoding an activation domain. This library and a plasmid encoding a hybrid of the bait polypeptide fused to the DNA-binding domain are cotransformed into a yeast reporter strain, and the resulting transformants are screened for those that express the reporter gene. For example, and not by way of limitation, the bait (e.g., Or83b) gene can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait (e.g., Or83b) polypeptide are to be detected can be made using methods routinely practiced in the art. According to the particular system described herein, for example, the cDNA fragments can be inserted into a vector such that they are translationally fused to the activation domain of GAL4 This library can be co-transformed along with the bait gene-GAL4 fusion plasmid into a yeast strain which contains a lacZ gene driven by a promoter which contains GAL4 activation sequence. A cDNA encoded protein, fused to GAL4 activation domain, that interacts with bait polypeptide will reconstitute an active GAL4 protein and thereby drive expression of the lacZ gene. Colonies which express lacZ can be detected by their blue color in the presence of X-gal. The cDNA can then be purified from these strains, and used to produce and isolate the bait gene-interacting protein using techniques routinely practiced in the art.

5.8.2. Assays for Compounds that Interfere with Or83b Signaling

The Or83b polypeptides of the invention can, in vivo, interact with one or more cellular macromolecules, such as proteins, including but not limited to G proteins. Such macromolecules can include, but are not limited to those proteins identified via methods such as those described, above, in Section 5.8. Compounds that disrupt such interactions can be useful in regulating the activity of an Or83b polypeptide, thereby modulating insect behavior. Such compounds can include, but are not limited to molecules such as antibodies, peptides, and the like.

The basic principle of the assay systems used to identify compounds that interfere with the interaction between an Or83b polypeptide and its cellular binding partner or partners involves preparing a reaction mixture containing the Or83b polypeptide and the binding partner under conditions and for a time sufficient to allow the two to interact and bind, thus forming a complex. In order to test a compound for inhibitory activity, the reaction mixture is prepared in the presence and absence of the test compound. The test compound can be initially included in the reaction mixture, or can be added at a time subsequent to the addition of an Or83b polypeptide and its cellular binding partner. Control reaction mixtures are incubated without the test compound or with a placebo. The formation of any complexes between the Or83b polypeptide and the cellular binding partner is then detected. The formation of a complex in the control reaction, but not in the reaction mixture containing the test compound, indicates that the compound interferes with the interaction of the Or83b polypeptide and the interactive binding partner.

The assay for compounds that interfere with the interaction of the Or83b polypeptides and binding partners can be conducted in a heterogeneous or homogeneous format. Heterogeneous assays involve anchoring either the Or83b polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the Or83b polypeptides and the binding partners, e.g., by competition, can be identified by conducting the reaction in the presence of the test substance; i.e., by adding the test substance to the reaction mixture prior to or simultaneously with the Or83b polypeptide and interactive cellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the Or83b polypeptide or the interactive cellular binding partner, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with a solution of the Or83b polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the Or83b polypeptide and the interactive cellular binding partner is prepared in which either the Gr83b polypeptide or its binding partner is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt Or83b polypeptide/cellular binding partner interaction can be identified.

In a particular embodiment, the target polypeptide can be prepared for immobilization using recombinant DNA techniques. For example, the Or83b coding region can be fused to a glutathione-S-transferase (GST) gene using a fusion vector, such as pGEX-5X-1, in such a manner that its binding activity is maintained in the resulting fusion protein. The interactive cellular binding partner can be purified and used to raise a monoclonal antibody, using methods routinely practiced in the art and described above, in Section 5.6. This antibody can be labeled with the radioactive isotope $^{125}$I, for example, by methods routinely practiced in the art. In a heterogeneous assay, e.g., the GST-Or83b fusion protein can be anchored to glutathione-agarose beads. The interactive cellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the Or83b polypeptide and the interactive cellular binding partner can be detected by measuring the amount of radioactivity that remains associated with the glutathione-agarose beads. A successful inhibition of the interaction by the test compound will result in a decrease in measured radioactivity.

Alternatively, the GST-Or83b fusion protein and the interactive cellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the Or83b polypeptide/binding partner interaction can be detected by adding the labeled antibody and measuring the radioactivity associated with the beads.

In another embodiment of the invention, these same techniques can be employed using peptide fragments that correspond to the binding domains of the Or83b polypeptide and/or the interactive cellular binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular binding partner is obtained, short gene segments can be engineered to express peptide fragments of the protein, which can then be tested for binding activity and purified or synthesized.

For example, and not by way of limitation, an Or83b polypeptide can be anchored to a solid material as described, above, in this Section, by making a GST-Or83b fusion protein and allowing it to bind to glutathione agarose beads. The interactive cellular binding partner can be labeled with a radioactive isotope, such as $^{35}$S, and cleaved with a proteolytic enzyme such as trypsin. Cleavage products can then be added to the anchored GST-Or83b fusion protein and allowed to bind. After washing away unbound peptides, labeled bound material, representing the cellular binding partner binding domain, can be eluted, purified, and analyzed for amino acid sequence by well known methods. Peptides so identified can be produced synthetically or fused to appropriate facilitative proteins using well known recombinant DNA technology.

5.9. Uses of Or83b Modulators

In another embodiment of the invention, insect odorant receptor genes may be used in controlling agriculturally important pest species. For example, Or83b modulators, including but not limited to small molecules, proteins and nucleic acids, can have activity in modifying the behavior growth, feeding and/or reproduction of crop-damaging insects, or insect pests of farm animals or of other animals. Additionally, In general, effective pest control agents exert a disabling activity on the target pest such as attractions (for example into a bait or trap), repulsion, paralysis, blocked development, or cessation of feeding. Pest control agents may be classified as pesticides, repellants or attractants. Such pests include but are not limited to egg, larval, juvenile and adult forms of flies, locusts, mosquitoes, fleas, moths, beetles, cicadas, grasshoppers, and crickets.

Agonistic or antagonistic recombinant or synthetic Or83b proteins, analogs, or derivatives, or nucleic acids encoding such agonistic or antagonistic recombinant or synthetic Or83b proteins, analogs, or derivatives, can be assayed for insect attractant or repellent activity. Laboratory and field assays of insect attraction and repulsion are well known in the art, and those that may be used to test molecules that bind to or modulate Or83b receptors include but are not limited to those described by Foster et al., 1997, Annu. Rev. Entomol. 42:123-46; "Insect Olfaction," B. S. Hansson, Ed., Springer Verlag, Berlin, Heidelberg, N.Y.; Birkett et al., 2000, Proc. Nat'l Acad. Sci. USA. 97 (16):9329-34; De Moraes et al., 2001, Nature. 410 (6828):577-80; Kline et al., 1990, Med Vet Entomol. 4 (4):383-91; Phelan, 1987, J. Econ. Entomol. 80:779-783; and Leskey et al., 2001, J Chem Ecol. 27 (1): 1-17.

In one embodiment, Or83b genes encoding dominant negative forms of Or83b proteins can be tested as insect control agents in the form of recombinant viruses that direct the expression of a dominant negative Or83b odorant receptor gene in the target pest. Suitable recombinant virus systems for expression of proteins in infected insect cells include but are not limited to recombinant Semliki Forest virus (DiCiommo and Bremner, 1998, J. Biol. Chem. 273:18060-66), recombinant sindbis virus (Higgs et al., 1995, Insect Mol. Biol 4:97-103; Seabaugh et al., 1998, Virology 243:99-112), recombinant pantropic retrovirus (Matsubara et al., 1996, Proc. Natl. Acad. Sci. USA 93:6181-85; Jordan et al., 1998, Insect Mol. Biol. 7:215-22), and most preferably recombinant baculovirus. Use of recombinant baculoviruses as a means to engineer expression of proteins in insects, and as insect control agents, is well known in the art. This approach has a number of specific advantages including host specificity, environmental safety, the availability of easily manipulable vector systems, and the potential use of the recombinant virus directly as a pest control agent without the need for purification or formulation of the Or83b protein (Cory and Bishop, 1997, Mol. Biotechnol. 7 (3):303-13; U.S. Pat. No. 5,470,735; U.S. Pat. No. 5,352,451; U.S. Pat. No. 5,770,192; U.S. Pat. No. 5,759,809; U.S. Pat. No. 5,665,349; U.S. Pat. No. 5,554,592). Thus, recombinant baculoviruses that direct the expression of Or83b odorant receptor genes can be used for both testing the pest control activity of the Or83b proteins under controlled laboratory conditions, and as insect control agents in the field. Alternatively, for testing the dominant negative activity of Or83b receptor genes, transgenic insects can be made as taught by Handler, 2001, Insect Biochem Mol Biol. 31 (2): 111-28, or by Atkinson et al., 2001, Annu. Rev. Entomol. 46:317-46.

Insect Or83b proteins, nucleic acids, and most preferably ligands, such as those agonists and antagonists identified by the methods described in Section 5.7.1, supra, may be formulated with any carrier suitable for agricultural use, such as water, organic solvents and/or inorganic solvents. The pest control agent composition may be in the form of a solid or liquid composition and may be prepared by fundamental formulation processes including but not limited to dissolving, mixing, milling, granulating, and dispersing.

The present invention encompasses compositions containing an insect Or83b odorant receptor protein or gene or ligand in a mixture with agriculturally acceptable excipients known in the art, including but not limited to vehicles, carriers, binders, UV blockers, adhesives, hemecants, thickeners, dispersing agents, preservatives and insect attractants. Thus the compositions of the invention may, for example, be formulated as a solid comprising the active agent and a finely divided solid carrier. Alternatively, the active agent may be contained in liquid compositions including dispersions, emulsions and suspensions thereof. Any suitable final formulation may be used, including for example, granules, powder, bait pellets (a solid composition containing the active agent and an insect attractant or food substance), microcapsules, water dispersible granules, emulsions and emulsified concentrates.

Examples of solid carriers suitable for use with the present invention include but are not limited to starch, active carbon, soybean powder, wheat powder, wood powder, fish powder, powdered milk, talc, kaolin, bentonite, calcium carbonate, zeolite, diatomaceous earth, fine silica powder, clay, alumina, pyrophyllite, kieselguhr chalk, lime, fuller's earth, cottonseed hulls, pumice, tripoli, walnut shell flour, redwood flour, and lignin.

Examples of liquid carriers suitable for use with the present invention include but are not limited to water, isopropyl alcohol, ethylene glycol, cyclohexanone, methyl ethyl ketone, dioxane, tetrahydrofuran, kerosene, light oil, xylene, trimethylbenzene, tetramethylbenzene, methylnaphthalene, solvent naphtha, chlorobenzene, dimethylacetamide, a glycerin ester, an acetonitrile, or dimethylsulfoxide.

Insect repellent formulations for a non-human animal may be in the form of a pour-on formulation, a spot-on formulation, a spray, a shampoo, a dusting powder, an impregnated strip, a soap, an ear or tail tag or a gel. Insect repellent formulations for humans can be in the form of a powder, an ointment, a lotion, a wipe, a cream, a soap, an erodible stick or a clothes patch. The formulation may include antioxidants and UV absorbers. Creams and lotions are of particular interest and may be adapted for application to the skin.

For agricultural uses, formulations containing the attractants of the invention using lures, baits or traps. Formulations containing repellants can be applied to the trees, plants or areas to be treated in the form of sprays, droplets, microfilms, microcapsules, or thin defined layers by using conventional devices known to those skilled in the art. Such formulations may be formulated for controlled release. The repellant formulation may be in the form of dispersion coating, film coating, spray coating, microencapsulated products, polymer slow release drops, globs, blocks, such as paraffin blocks, monoliths, puffers, and any such other similar form as known in the art. Various controlled-release systems are described in Controlled Delivery of Crop-Protection Agents, Taylor and Francis, New York, (1990), Editor R. M. Wilkins, especially chapters 3 and 9 and in Insect Suppression with Controlled Release Pheromone Systems, Vol. I and II, CRC Press, Boca Raton, Fla. (1982).

The following examples are provided merely as illustrative of various aspects of the invention and shall not be construed to limit the invention in any way.

6. EXAMPLE

Identification and Sequence Analysis of cDNAs of Insect Or83b Genes

Using low stringency hybridization, genes related to *Drosophila melanogaster* Or83b have been identified in the Mediterranean fruit fly (medfly), *Ceratitis capitata*, an extremely destructive agricultural pest; from *Anopheles gambiae*, a mosquito carrier of malaria; *Helicoverpa zea* (corn earworm, cotton bollworm), and from *Schistocerca americana*, a common locust.

6.1. Identification of an Or83b Gene in *C. capitata*

The *D. melanogaster* Or83b gene, depicted in FIG. 1, was used to screen a *C. capitata* genomic DNA library under low stringency hybridization conditions. Several overlapping clones were purified and mapped. Genomic DNA fragments that hybridized to the *D. melanogaster* probe were subcloned and sequenced.

GENSCAN analysis and sequence comparison to the *Drosophila* Or83b gene was used to predict intron-exon structure. RT-PCR with *C. capitata* adult antennal mRNA was used to amplify a fragment representing the entire open reading frame of the Or83b gene, and these results confirmed the predicted intron-exon structure. The sequence of the *C. capitata* Or83b cDNA is shown in FIG. 2. The *C. capitata* and *D. melanogaster* predicted polypeptides display 88% identity and 92% similarity.

6.2. Identification of an Or83b Gene in *Helicoverpa zea*

A cDNA library prepared from adult *Helicoverpa zea* (corn earworm) antennae was screened at low stringency, using the *D. melanogaster* Or83b gene as a probe. Several hybridizing clones were purified and analyzed. Sequence analysis of the longest of these identified cDNA clones, shown in FIG. 3, reveals a high degree of sequence similarity to *D. melanogaster* Or83b. Overall, the *H. zea* and *D. melanogaster* Or83b polypeptides show 64% identity and 76% similarity.

6.3. Identification of an Or83b Gene in *Anopheles gambiae*

Recently, a large-scale effort has been initiated to determine the complete genome sequence of *Anopheles gambiae*, the principal mosquito vector responsible for the transmission of malaria. Researchers at Genoscope and the Institut Pasteur, France have made public a database consisting of 17,000 random sequences from the *Anopheles* genome. This database represents 12,000,000 base pairs, or roughly 5% of the total mosquito genome. A BLAST search of this *Anopheles* database was performed with the *D. melanogaster* Or83b gene, identifying two independent sequences that display high sequence similarity to two different regions of *Drosophila* Or83b. The two sequence fragments were thought to represent two adjacent portions of a single Or83b gene in the *Anopheles* genome. This idea was confirmed using PCR to amplify a 3 kb fragment spanning these two sequences. This fragment was then used to screen an *Anopheles* genomic DNA library and hybridizing clones were subcloned and sequenced.

GENSCAN analysis and sequence comparison to the *Drosophila* Or83b gene was used to predict intron-exon structure. RT-PCR with *Anopheles* adult head mRNA was used to amplify a fragment representing the entire open reading of the Or83b gene, and these results confirmed the predicted intron-exon structure. The *A. gambiae* and *D. melanogaster* Or83b predicted polypeptides show 77% identity and 84% similarity. The sequence of the identified *A. gambiae* Or83b gene is shown in FIG. 4.

6.4. Identification of an Or83b Gene in *Schistocerca americana*

A degenerate PCR approach was used to identify an Or83b gene from the locust *Schistocerca americana*. Briefly, degenerate oligonucleotide primers [forward primer: A45 1.1 (AAR TAY TGG GTI GAR MGI CA), SEQ ID NO:19, corresponding the amino acid sequence KYWERH; reverse primer: A45 2.2 (API CKR TTI CGR AAD ATR CA), SEQ ID NO:20, corresponding to the sequence CIFGNRL] were used to amplify a 235-bp fragment from *S. americana* adult antennal cDNA. This fragment was then used to screen a *S. americana* antennal cDNA library and several clones were isolated and analyzed. The sequence of the open reading frame and the corresponding amino acid sequence of this *S. americana* Or83b gene is shown in FIG. 5. The *S. americana* and *D. melanogaster* Or83b amino acid sequences show 59% identity and 72% similarity.

6.5. Sequence Analysis of Insect Or83b Genes

A ClustalW alignment of the predicted amino acid sequences of the identified Or83b homologs is shown in FIG. 6. This analysis indicates that the C-terminal half of the protein displays a significant degree of conservation across insect species. Analysis of predicted transmembrane domains in the deduced amino acid sequences reveals the number of these domains and their relative positions within the protein sequence are also conserved in comparison to *Drosophila melanogaster* Or83b. The regions of strong sequence conservation represent an amino acid "signature" motif than can be used to isolated and recognize putative homologs of Or83b in diverse insect species, such as, for example: RSAIKYWERHKHVVR (amino acids 322-337 of SEQ ID NO: 2); FCIFGN(RorS)L (amino acids 395-402 of SEQ ID NO: 2 or amino acids 1-8 of SEQ ID NO: 17); WYDGSEEAK (amino acids 431-439 of SEQ ID NO: 10); FASVLGAVVTYFMVLVQLK (amino acids 470-486 of SEQ ID NO: 10).

6.6. Expression of Insect Or83b Genes

RNA in situ hybridization was used to determine the spatial pattern of expression of these identified Or83b genes in insect olfactory tissues. In insects, olfactory neurons are restricted to the antenna and maxillary palp. In flies such as *Drosophila*, olfactory neurons are located in a single antennal segment. In mosquitoes, lepidoptera and orthoptera, in contrast, the antenna is a long, multi-segmented organ and olfactory neurons are found in repeated antennal segments. The expression of the *Ceratitis* and *Anopheles* Or83b genes in was examined longitudinal sections of adult antennae (FIGS. 7B and 7C, respectively). Expression of both genes was detected in multiple antennal cells. The position of these cells beneath sensory hairs on the surface of the antenna, as well as their morphology, is consistent with their identity as olfactory neurons (FIG. 7A).

The spatial pattern of expression of the *Helicoverpa* Or83b gene was examined in longitudinal sections of the adult female antenna by in situ hybridization (FIG. 7D). Again, expression of this gene was detected in numerous cells in each of the antennal segments, and their position and morphology strongly suggested their identity as olfactory neurons.

Expression of the *Schistocerca* Or83b gene was detected in clusters of olfactory neurons in longitudinal sections of adult locust antenna (FIG. 7E).

Thus, these data provide evidence that in these other insect species, as in *Drosophila*, Or83b is expressed by a large number of olfactory neurons, consistent with a conserved and essential role for this putative GPCR in odor recognition in insects.

7. DEPOSIT OF MICROORGANISMS

The following plasmids were deposited with the American Type Culture Collection (ATCC), Manassas, Va., on Jul. 30, 2001, and have been assigned the indicated Accession numbers:

| Microorganism | ATCC Accession No. |
| --- | --- |
| Cc83b-2 | PTA-3573 |
| Hz-8.1A10 | PTA-3574 |
| Ag83b-1 | PTA-3575 |
| Sa83b | PTA-3576 |

Cc83b-2 is the *Certatitis capitata* Or83b cDNA in the pGEM-T-Easy vector; Hz-8.1A10 is the *Helicoverpa zea* Or83b cDNA in pBluescript SK-; Ag83b-1 is the *Anopheles gambiae* Or83b cDNA in the pGEM-T-Easy vector; and Sa83b is the *Schistocerca americana* Or83b cDNA in pBluescript SK-.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, including patent applications, patents, and publications, the disclosures of which are hereby incorporated by reference in their entireties.

What is claimed is:

1. An isolated nucleic acid molecule comprising a nucleotide sequence which encodes a polypeptide molecule comprising the amino acid sequence of SEQ ID NO: 11, or a fragment thereof of at least 20 amino acids in length, wherein said polypeptide molecule has at least one property of an insect Or83b polypeptide with the proviso that the amino acid sequence of said polypeptide is not found in SEQ ID NO: 10.

2. The isolated nucleic acid molecule of claim 1, which further comprises an origin of replication.

3. The isolated nucleic acid molecule of claim 1, in which the nucleotide sequence is operatively linked to a promoter.

4. A host cell transformed with the nucleic acid molecule of claim 2.

* * * * *